(12) United States Patent
Shapiro et al.

(10) Patent No.: US 10,301,621 B2
(45) Date of Patent: *May 28, 2019

(54) MULTIFUNCTIONAL RNA NANOPARTICLES AND METHODS OF USE

(71) Applicant: The United States of America, as represented by the Secretary, Department of Health & Human Services, Washington, DC (US)

(72) Inventors: Bruce A. Shapiro, Gaithersburg, MD (US); Kirill A. Afonin, Charlotte, NC (US); Mathias D. Viard, Frederick, MD (US); Angelica N. Martins, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/022,530

(22) PCT Filed: Sep. 17, 2014

(86) PCT No.: PCT/US2014/056007
§ 371 (c)(1),
(2) Date: Mar. 16, 2016

(87) PCT Pub. No.: WO2015/042101
PCT Pub. Date: Mar. 26, 2015

(65) Prior Publication Data
US 2017/0121708 A1    May 4, 2017

Related U.S. Application Data

(60) Provisional application No. 61/878,758, filed on Sep. 17, 2013.

(51) Int. Cl.
| | | |
|---|---|---|
| *C07H 21/04* | (2006.01) | |
| *C12N 15/113* | (2010.01) | |
| *C12N 15/11* | (2006.01) | |
| *C12N 15/87* | (2006.01) | |
| *A61K 31/713* | (2006.01) | |
| *A61K 47/54* | (2017.01) | |
| *A61K 47/69* | (2017.01) | |
| *B82Y 5/00* | (2011.01) | |

(52) U.S. Cl.
CPC .......... *C12N 15/113* (2013.01); *A61K 31/713* (2013.01); *A61K 47/549* (2017.08); *A61K 47/6929* (2017.08); *C12N 15/111* (2013.01); *C12N 15/1132* (2013.01); *C12N 15/87* (2013.01); *B82Y 5/00* (2013.01); *C12N 2310/14* (2013.01); *C12N 2310/351* (2013.01); *C12N 2310/3519* (2013.01); *C12N 2310/51* (2013.01); *C12N 2310/52* (2013.01); *C12N 2320/32* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 5,466,586 A | 11/1995 | Davey et al. | |
| 5,580,737 A | 12/1996 | Polisky et al. | |
| 6,261,783 B1 | 7/2001 | Jayasena et al. | |
| 6,469,158 B1 | 10/2002 | Usman et al. | |
| 6,787,305 B1 | 9/2004 | Li et al. | |
| 2002/0161219 A1 | 10/2002 | Kanavarioti et al. | |
| 2004/0197804 A1 | 10/2004 | Keefe et al. | |
| 2004/0253679 A1 | 12/2004 | Epstein et al. | |
| 2005/0037394 A1 | 2/2005 | Keefe et al. | |
| 2017/0175122 A1 | 6/2017 | Guo et al. | |

FOREIGN PATENT DOCUMENTS

| | | |
|---|---|---|
| WO | WO-2008039254 A2 | 4/2008 |
| WO | WO-2010148085 A1 | 12/2010 |
| WO | WO-2012125987 A2 | 9/2012 |
| WO | WO-2013/075140 A1 | 5/2013 |
| WO | WO-2013075132 A1 | 5/2013 |
| WO | WO-2014039809 A2 | 3/2014 |
| WO | WO-2015042101 A1 | 3/2015 |
| WO | WO-2015171827 A1 | 11/2015 |
| WO | WO-2017139758 A1 | 8/2017 |
| WO | WO-2017197009 A1 | 11/2017 |

OTHER PUBLICATIONS

Shu et al. (Methods 54 (2011) 204-214).*
Office Action dated Nov. 15, 2017 in corresponding European Patent Application No. 14780963.6.
Aafonin, et al., ACS Nano, 2016 vol. 16, pp. 1746-1753.
Aafonin, et al., Nano. Lett., 2014, vol. 14, pp. 5662-5671.
Aafonin, et al., Nucleic Acids Research, 2014, vol. 42(3), pp. 2085-2097.
Aafonin, et al., Nanotechnology, 2013, pp. 1-15.
Halman et al., Nucleic Acids Research, 2017, vol. 45(4), pp. 2210-2220.
Wang, et al., J Control Release, 2016, vol. 233, pp. 126-135.
Y. Shu et al: "Fabrication of 14 different RNA nanoparticles for specific tumor targeting without accumulation ion normal organs", RNA, vol. 19, No. 6, Apr. 19, 2013 (Apr. 19, 2013), pp. 767-777.
Kirill A. Afonin et al: "Activation of different split functionalities on re-association of RNA-DNA hybrids", Nature Nanotechnology, vol. 8, No. 4, Mar. 31, 2013 (Mar. 31, 2013), pp. 296-304.
Wade W Grabow et al: "Self-assembling RNA nanorings based on RNAI/II inverse kissing complexes", Nano Letters, American Chemical Society, US, vol. 11, No. 2, Feb. 9, 2011 (Feb. 9, 2011), pp. 878-887.

(Continued)

*Primary Examiner* — Kimberly Chong
(74) *Attorney, Agent, or Firm* — Leydig, Voit & Mayer, Ltd.

(57) ABSTRACT

The instant invention provides RNA nanoparticles and R/DNA chimeric nanoparticles comprising one or more functionalities. The multifunctional RNA nanoparticles are suitable for therapeutic or diagnostic use in a number of diseases or disorders.

19 Claims, 43 Drawing Sheets

Specification includes a Sequence Listing.

(56) References Cited

OTHER PUBLICATIONS

Afonin Kirill A et al: "Design and self-assembly of siRNA-functionalized RNA nanoparticles for use in automated nanomedicine", Nature Protocols, Nature Publishing Group, GB, vol. 6, No. 12, Dec. 1, 2011 (Dec. 1, 2011), pp. 2022-2034.

Afonin K A et al: "Co-transcriptional assembly of chemically modified RNA nanoparticles functionalized with siRNAs", Nano Letters, American Chemical Society, US, vol. 12, No. 10, Oct. 10, 2012 (Oct. 10, 2012), pp. 5192-5195.

Peixuan Guo: "RNA nanotechnology: engineering, assembly and applications in detection, gene delivery and therapy", Journal of Nanoscience and Nanotechnology, American Scientific Publishers, US, vol. 5, Jan. 1, 2005 (Jan. 1, 2005), pp. 1964-1982.

Zhang David Yu et al: "Dynamic DNA nanotechnology using strand-displacement reactions", Nature Chemistry, Nature Publishing Group, GB, vol. 3, No. 2, Feb. 2011 (Feb. 1, 2011), pp. 103-113.

Kirill A. Afonin et al: "Multifunctional RNA Nanoparticles", Nano Letters, vol. 14, No. 10, Sep. 30, 2014 (Sep. 30, 2014), pp. 5662-5671.

Kirill A. Afonin et al: "Triggering of RNA Interference with RNA-RNA, RNA-DNA, and DNA-RNA Nanoparticles", ACS Nano, Dec. 18, 2014 (Dec. 18, 2014).

Bujold, et al., Sequence-responsive unzipping DNA cubes with tunable cellular uptake profiles:, Chem. Sci., vol. 5, pp. 2449-2455 (2014) (reference submitted on Feb. 21, 2018).

Righetti, et al., "Temperature-responsive in vitro RNA structurome of Yersinia pseudotuberculosis", Proc. Natl. Acad. Sci. USA, vol. 113, pp. 7273-7242 (Jun. 28, 2016) (reference submitted on Feb. 21, 2018).

Afonin et al., "In Silico Design and Enzymatic Synthesis of Functional RNA Nanoparticles", Acc.Chem. Res., 2014, 47 (6) pp. 1731-1741 (dx.doi.org/10.1021/ar400329z).

Guo, P., "The Emerging Field of RNA Nanotechnology", *Nat Nanotechnol* 2010, 5, (12), 833-42.

Jaeger, L.; Chworos, A., "The architectonics of programmable RNA and DNA nanostructures", Curr Opin Struct Biol 2006, 16, (4), 531-43.

Khisamutdinov et al., "Physicochemically Tunable Polyfunctionalized RNA Square Architecture with Fluorogenic and Ribozymatic Properties", vol. 8, No. 8, pp. 7620-7629; ASCNano 2014.

Shapiro B et al., "Protocols for the in silico Design of RNA Nanostructures. In: Nanostructure Design Methods and Protocols", Totowa, NJ: Humana Press; 2008. p. 93-115 [Book Chapter].

Yingling YG et al., "Computational Design of an RNA Hexagonal Nanoring and an RNA Nanotube", Nano Lett. 7(8): 2328-2334, 2007.

* cited by examiner siRNAs attached through toeholds

DNAs with 3' toeholds

Side View   Front View 10 nm 10 nm

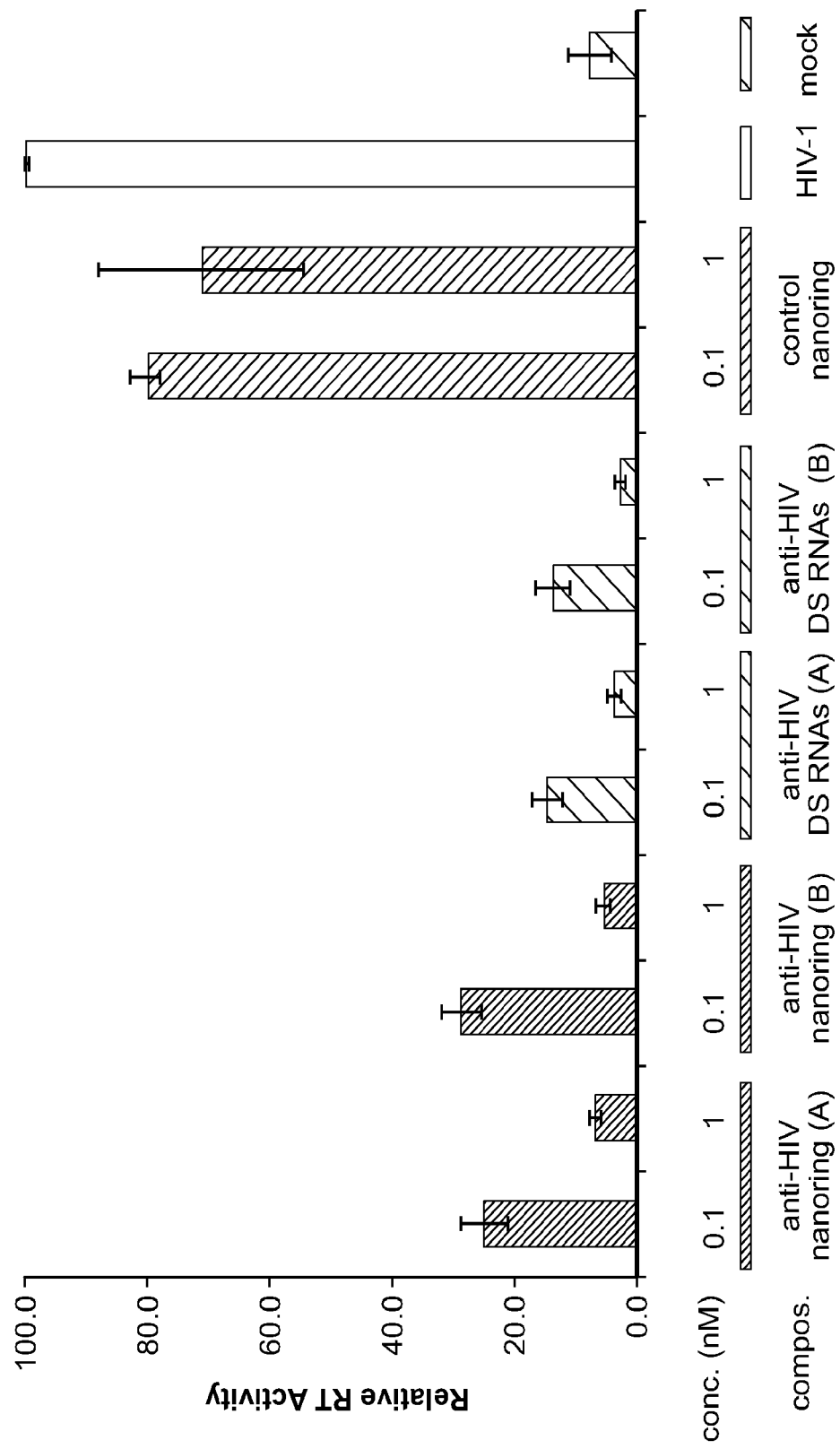

— MDA-MB-231/eGFP cells
---- cells transfected with nanoring with six DS RNAs
—— cells transfected with six DS RNAs 30000 cells per sample

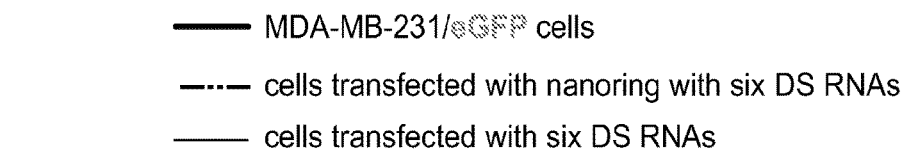
FIG. 12C
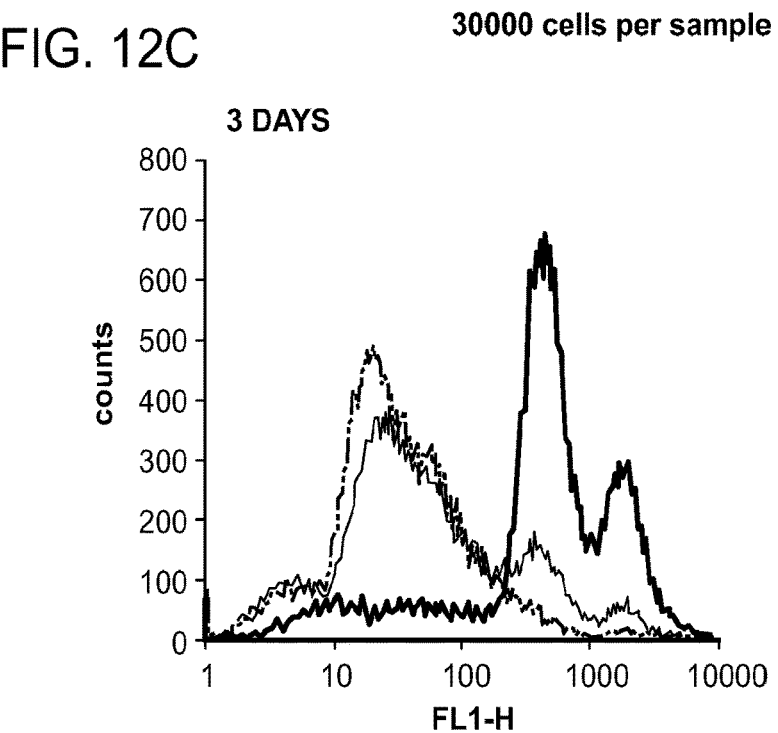
FIG. 12D
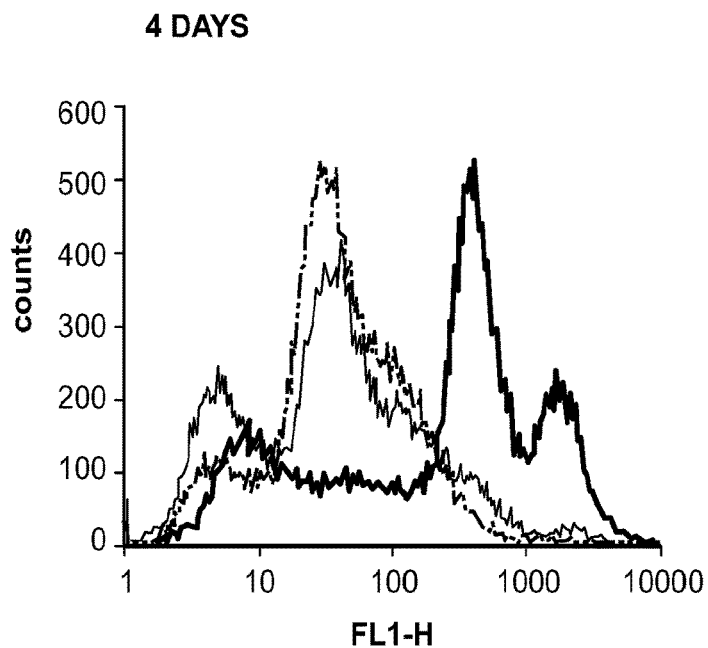

—— MDA-MB-231/eGFP cells
--- cells transfected with nanoring with six DS RNAs
—— cells transfected with six DS RNAs 30000 cells per sample

5 DAYS

6 DAYS

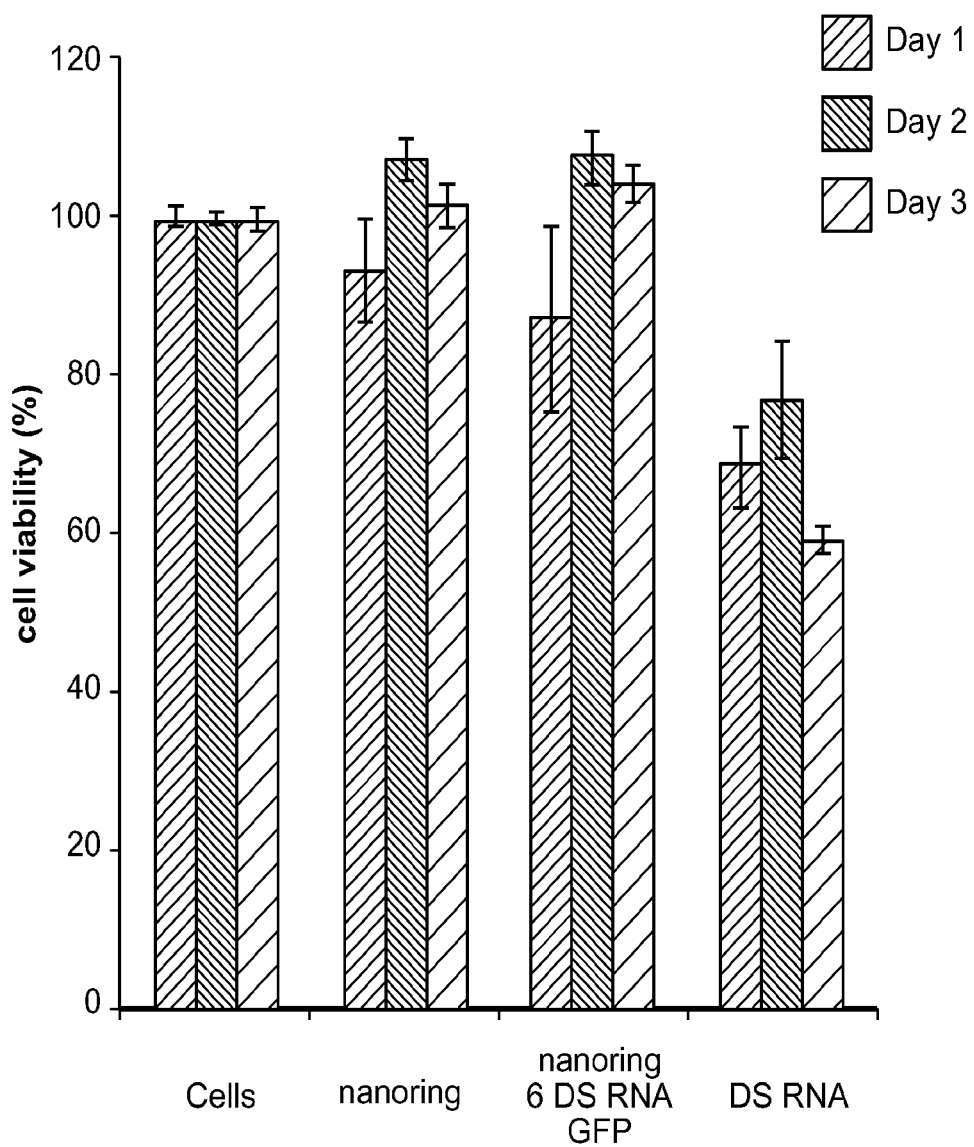

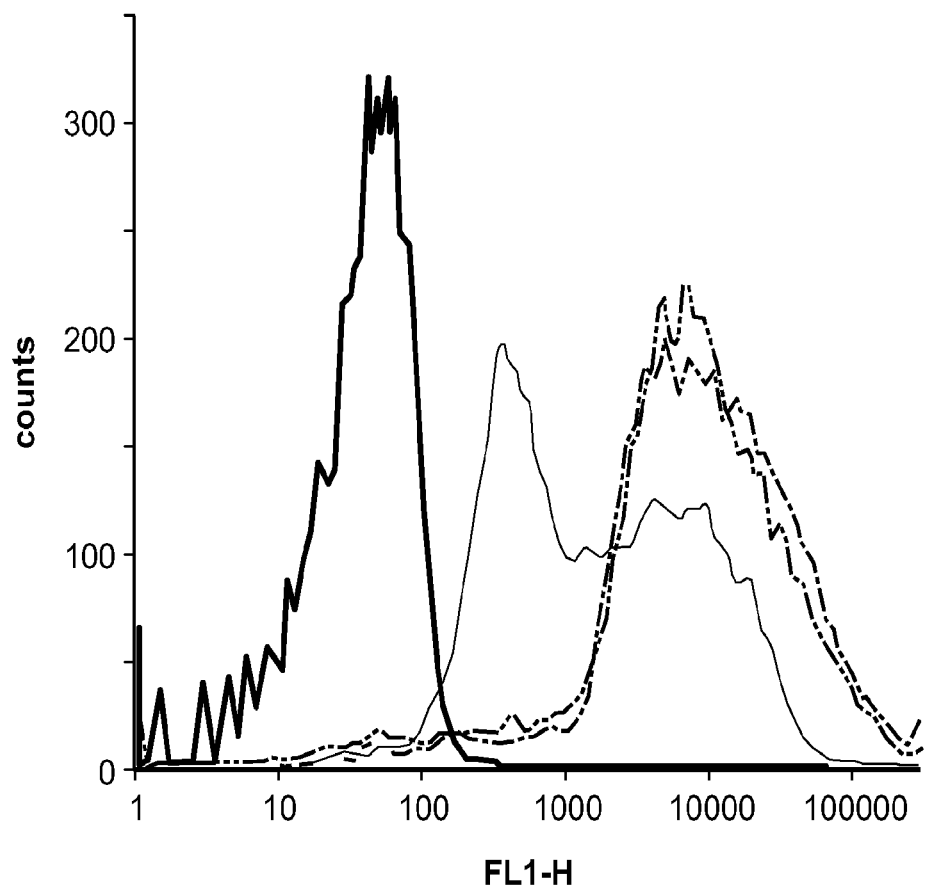

ring with six toeholds (R6t)

DS RNAs ring with six toeholds and six DS RNAs (R6t6Ds)

native PAGE

MULTIFUNCTIONAL RNA NANOPARTICLES AND METHODS OF USE

CROSS-REFERENCE TO RELATED APPLICATIONS

The present application is a national stage patent application filed under 35 U.S.C. § 371 based on International Application No. PCT/US2014/056007, filed Sep. 17, 2014, which claims priority to, and the benefit under 35 U.S.C. § 119(e) of, U.S. provisional patent application No. 61/878,758, filed Sep. 17, 2013, entitled "Multifunctional RNA Nanoparticles and Methods of Use". The entire teachings of this application are incorporated herein by reference.

GOVERNMENT FUNDING

Research supporting this application was carried out by the United States of America as represented by the Secretary, Department of Health and Human Services.

SEQUENCE LISTING

The instant application contains a Sequence Listing which has been submitted electronically in ASCII format and is hereby incorporated by reference in its entirety. Said ASCII copy, created on Sep. 8, 2016, is named 1420378_422US9_SL.txt and is 16,376 bytes in size.

BACKGROUND OF THE INVENTION

While RNA interference (RNAi) continues to hold incredible potential, numerous challenges associated with the application of RNAi technology must be addressed before it can be made into a viable therapy. The most prominent include transporting, targeting, and stabilizing short interfering RNAs (siRNAs) into tumor cells after injection into a patient's bloodstream. One of the most promising set of solutions to date includes the use of various types of nanoparticles (NPs) (see, e.g., Whitehead et al 2009 or Oh and Park 2009).

The rapidly expanding field of nanobiology opens up the possibilities for the development of new methods and compositions that can be used for the diagnosis, prognosis, and treatment of a multitude of diseases and conditions. However, while an increasing number of novel drugs and therapeutic agents are being discovered, the problem of delivering them specifically to the desired site or cell has not been solved. RNA nanoparticles have been shown to be able to carry multiple components, including molecules for specific cell recognition, image detection, and therapeutic treatment. The use of such protein-free nanoparticles holds the promise for the repeated long-term treatment of chronic diseases with low immune response and should avoid the problems of short retention time of small molecules and the difficulty of delivery of particles larger than 100 nanometers.

For example, NPs can provide several distinct advantages toward the advancement of RNAi therapeutics. For instance, they have been shown to produce a nanoparticle effect that improves cellular uptake. Moreover, NPs offer an increased degree of protection against ribonuclease degradation while also accommodating additional functional groups like aptamers to aid cellular targeting.

While a broad range of materials have been used in RNAi nanotechnology, including some exotic synthetic materials, unmodified RNA nucleotides that serve as both the therapeutic and the structural core of NPs are thought to provide unique advantages. For example the use of natural RNA nucleotides—in addition to its biocompatibility—takes advantage of RNA's inherent ability to self-assemble and spatially arrange multiple siRNAs, RNA or DNA aptamers, fluorescent dyes, small molecules, RNA-DNA hybrids with split functionalities, and proteins. Furthermore, NPs made of unmodified nucleotides can be synthesized directly via run-off transcription, making their ease of synthesis and cost of production attractive for scaled-up production.

Accordingly, there remains a need in the art for the development of siRNA nanoscaffolds to address several present challenges associated with NP-based siRNA delivery including cell-targeting, ease of synthesis, and triggered activation of therapeutic functionalities, and to provide a safe and efficient nanoparticle needs for the delivery of effective therapeutic and diagnostic siRNAs.

SUMMARY OF THE INVENTION

Formation of functional RNA NPs takes place either with one-pot assembly or directly with T7 RNA polymerase transcription reactions when equimolar amounts of DNA templates encoding specifically designed RNAs that are part of the composition of the functional RNA NPs (see, e.g. PCT/US2013/058492, incorporated by reference in its entirety herein). The resulting high yield functional RNA NPs are endotoxin free and can be used for a wide range of biomedical applications. RNA NPs can provide several distinct advantages toward the advancement of RNAi therapeutics. For instance, they have been shown to produce a nanoparticle effect that improves cellular uptake and specific gene silencing at low concentrations in cells and in vivo. Moreover, NPs offer an increased degree of protection against ribonuclease degradation while also accommodating additional functional groups like aptamers to aid cellular targeting. The use of natural RNA nanoscaffolds, in addition to its biocompatibility, takes advantage of RNA's inherent ability to self-assemble and simultaneously spatially arrange multiple functionalities such as siRNAs, RNA or DNA aptamers, fluorescent dyes, small molecules, RNA-DNA hybrids with split functionalities and proteins.

As presented herein, besides functionalization with multiple short interfering RNAs for combinatorial RNA interference, these nanoscaffolds also allow simultaneous embedment of assorted RNA aptamers, fluorescent dyes, proteins, as well as recently developed auto-recognizing RNA-DNA hybrids used to conditionally activate multiple split functionalities.

Accordingly, in a first aspect, the present invention features an RNA nanoparticle (RNA NP) comprising one or more functionalities.

In another aspect, the invention features an R/DNA chimeric nanoparticle (R/DNA NP) comprising one or more functionalities.

Another aspect of the invention provides an R/DNA chimeric nanoparticle (R/DNA NP) having a nanoring structure and having one or more functionalities.

In one embodiment, the R/DNA NP possesses one or more RNA-DNA hybrid arm extensions. Optionally, one or more of the RNA-DNA hybrid arm extensions is capable of triggered release, formation and/or activation of a dsRNA.

In one embodiment, the functionalities comprise one or more agents. In another embodiments, the agents are selected from one or more of the group consisting of: inhibitory nucleic acids, fluorescent dyes, small molecules, RNA-DNA hybrids with split functionalities, split lipase, split GFP, proteins, therapeutic agents and imaging agents.

In a related embodiment, the inhibitory nucleic acids are selected from the group consisting of: siRNAs, RNA or DNA aptamers and ribozymes.

In one embodiment, the one or more agents the same. In another embodiment, the one or more agents are different.

In one embodiment, the R/DNA nanoparticle comprises at least two chimeric nanoparticles. In another embodiment, the first chimeric nanoparticle comprises a first DNA oligonucleotide and a complementary first RNA oligonucleotide comprising the one or more functionalities, and the second chimeric nanoparticle comprises a second DNA oligonucleotide and a complementary second RNA oligonucleotide comprising the one or more functionalities. In a further embodiment, the first DNA oligonucleotide comprises a 5' toehold sequence and the second DNA oligonucleotide comprises a 3' toehold sequence.

In another embodiment, the first RNA is complementary to the second RNA and when duplexed forms an siRNA.

In another embodiment, the siRNA inhibits a target RNA. In a further embodiment, the target RNA is one which produces a therapeutically beneficial result when inhibited. In another further embodiment, the target RNA comprises an RNA that encodes a protein involved in a disease process or a portion thereof. In a further related embodiment of any one of the above aspects, the target RNA encodes an apoptosis inhibitor protein. In another further related embodiment of any one of the above aspects, the target RNA is a pathogenic RNA genome, an RNA transcript derived from the genome of the pathogenic agent, or a portion thereof. In one embodiment, the pathogenic agent is a virus, a bacteria, a fungus, or a parasite. In another embodiment, the target RNA is a viral RNA genome or a portion thereof.

The invention also features a composition comprising an RNA NP or R/DNA NP of any one of the above aspects.

The invention also features a pharmaceutical composition comprising an RNA NP or R/DNA NP of any one of the above aspects.

In one embodiment, the pharmaceutical composition further comprises a pharmaceutically acceptable excipient, carrier, or diluent.

In another embodiment, the pharmaceutical composition is formulated for the treatment of a disease. In still another embodiment, the pharmaceutical composition of claim 20 or 21, wherein the pharmaceutical composition is formulated for the treatment of an infection by a pathogenic agent. In another related embodiment, the pathogenic agent is a virus, a bacteria, a fungus, or a parasite.

In another embodiment of any of the above aspects or embodiments, the pharmaceutical composition further comprises a second agent that treats or reduces the symptoms associated with infection by the pathogenic agent.

In one embodiment, the second agent is an anti-viral agent.

In another embodiment, the pharmaceutical composition is formulated for the treatment of a neoplasia.

In another further embodiment, the second agent is an anti-cancer agent.

The invention also features a method of inhibiting or reducing the expression of a target gene in a cell comprising contacting the cell with a therapeutically effective amount of the RNA NP or R/DNA NP of any of the above aspects or embodiments, or the composition of any one of the above aspects or embodiments.

The invention also features a method of killing a pathogen infected cell comprising contacting the cell with a therapeutically effective amount of the RNA NP or R/DNA NP of any one of the above aspects or embodiments or the composition of any one of the above aspects or embodiments.

The invention also features a method of inhibiting replication of a pathogen in a cell comprising contacting the cell with a therapeutically effective amount of the RNA NP or R/DNA NP of any one of the above aspects or embodiments or the composition of any one of the above aspects or embodiments.

In one embodiment, the cell is in a subject.

The invention also features a method of reducing pathogenic burden in a subject comprising administering a therapeutically effective amount of the RNA NP or R/DNA NP of any one of the above aspects or embodiments or the composition of any one of the above aspects or embodiments In one embodiment, the subject is at risk of developing a pathogenic infection.

In another embodiment, the subject is diagnosed with having a pathogenic infection.

The invention also features a method of treating or preventing a pathogenic infection in a subject comprising administering a therapeutically effective amount of the RNA NP or R/DNA NP of any one of the above aspects or embodiments or the composition of any one of the above aspects or embodiments.

In one embodiment, the method reduces the pathogenic burden, thereby treating or preventing the pathogenic infection. In another embodiment, the method induces death in infected cell, thereby treating or preventing the pathogenic infection.

In one embodiment, the subject is a mammal. In another embodiment, the subject is a human.

In one embodiment, the pathogen is a virus, bacteria, fungus, or parasite.

In another embodiment of any one of the above aspects or embodiments, the method further comprises contacting the cell with a therapeutically effective amount of a second therapeutic agent or administering a therapeutically effective amount of the second therapeutic agent to the subject.

In one embodiment, the second therapeutic agent treats the pathogenic infection or the symptoms associated with the pathogenic infection.

The invention also features a method of killing a neoplastic cell comprising contacting the cancer cell with a therapeutically effective amount of the of the RNA NP or R/DNA NP of any one of the above aspects or embodiments or the composition of any one of the above aspects or embodiments, thereby killing the neoplastic cell.

The invention also features a method of treating a subject having a neoplasia, the method comprising administering to a subject a therapeutically effective amount of the RNA NP or R/DNA NP of any one of the above aspects or embodiments or the composition of any one of the above aspects or embodiments, thereby treating the subject.

In one embodiment, the neoplastic cell is a cancer cell which is present in a solid tumor.

In another embodiment, the method further comprises contacting the cell with a therapeutically effective amount of a second therapeutic agent or administering a therapeutically effective amount of the second therapeutic agent to the subject.

In one embodiment, the second therapeutic agent is an anti-cancer agent.

The invention also features a kit comprising the RNA NP or R/DNA NP of any one of the above aspects or embodiments or the composition of any one of the above aspects or embodiments.

In one aspect, the kit further comprises a second therapeutic agent.

Other aspects of the invention are described in, or are obvious from, the following disclosure, and are within the ambit of the invention.

Figure 9A:
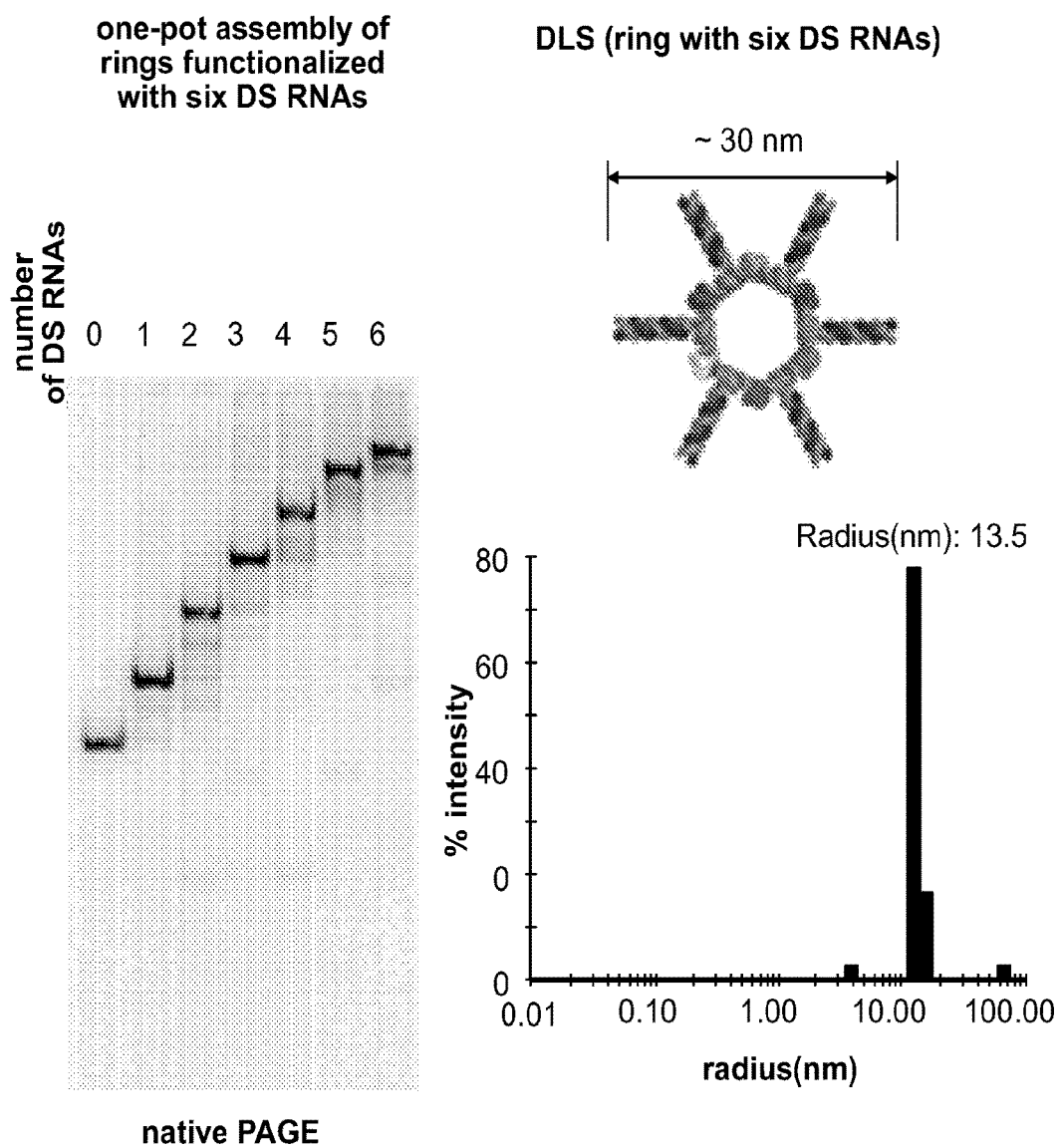
Figure 9B:
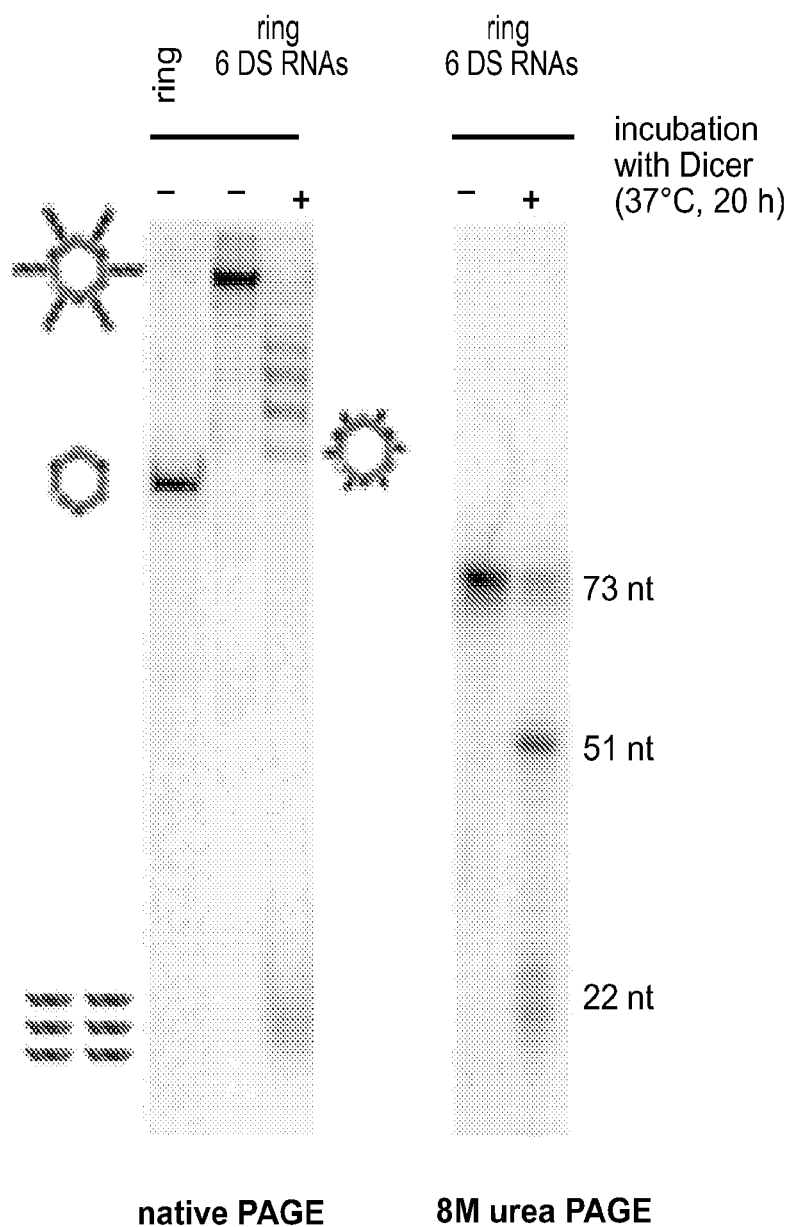
Figure 9C:
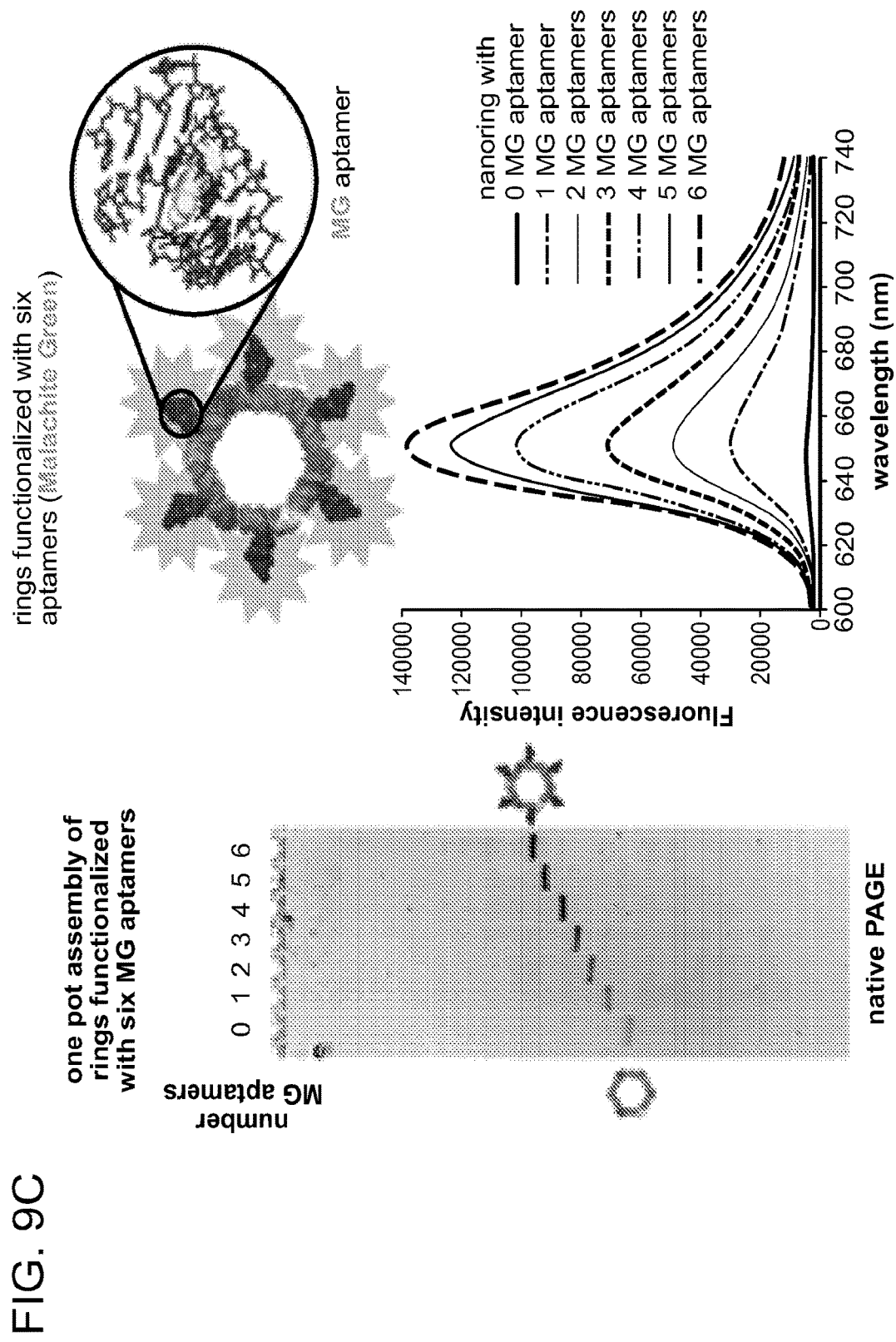
Figure 9D:
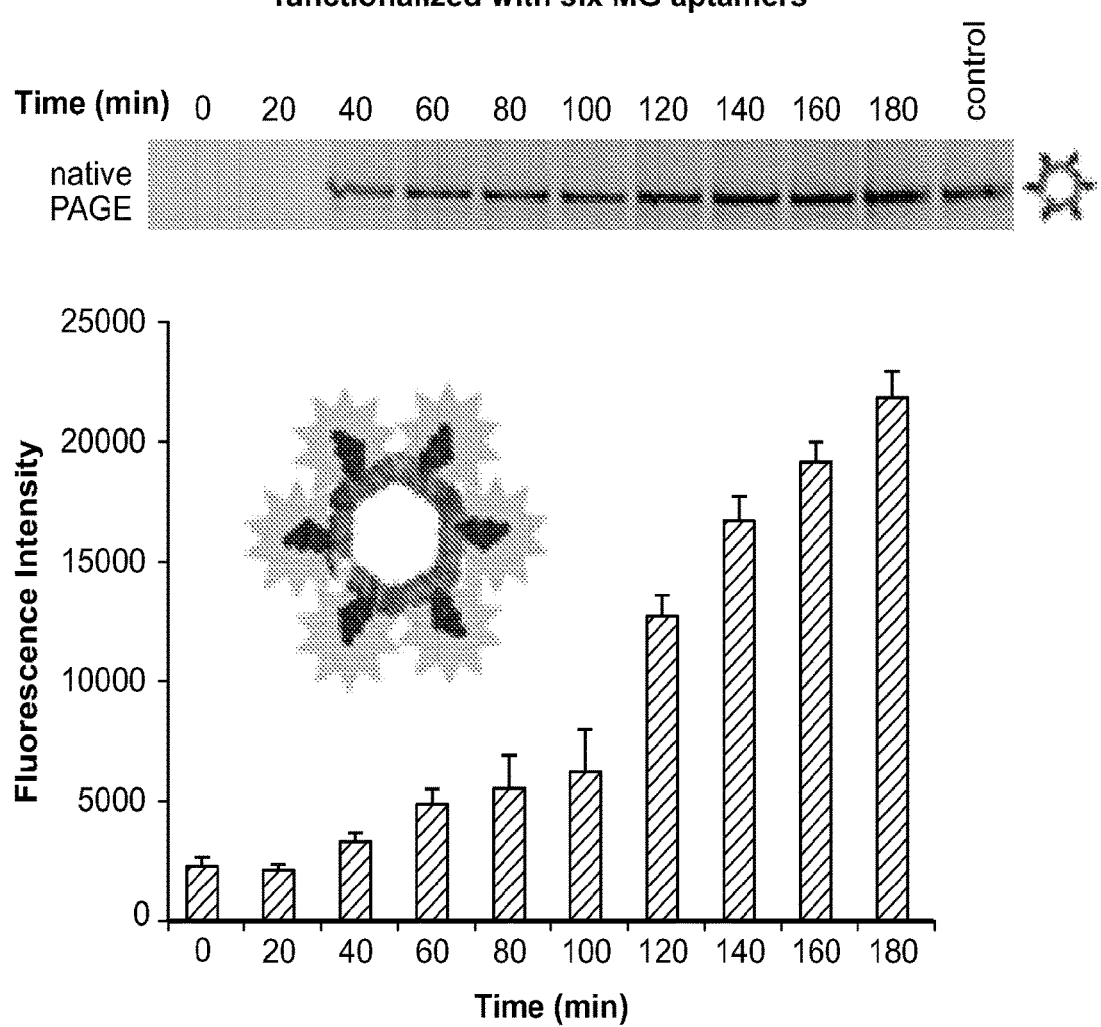

FIGS. 9a to 9d show assemblies of nanorings functionalized with DS RNAs or MG aptamers. FIG. 9a shows native-PAGE results representing assemblies leading to the formation of RNA nanorings functionalized with different numbers of DS RNAs (0-6). Dynamic light scattering (DLS) confirms assembly result and denotes nanoring radius. FIG. 9b shows in vitro dicing experiments (Afonin et al. *Nat Protoc* 2011, 6, 2022-34). RNA nanorings functionalized with six siRNAs were incubated with human recombinant Dicer enzyme. Constructs treated with Dicer were analyzed using native-PAGE (left) and denaturing 8M urea PAGE (right) and show successful siRNA cleavage. Non-functionalized RNA nanoring was used as a control. FIGS. 9c and 9d show one-pot (c) and co-transcriptional (d) assemblies of nanorings functionalized with up to six Malachite Green (MG) aptamers. Assemblies of RNA nanorings functionalized with different numbers (0-6) of a Malachite Green (MG)-specific aptamer (PDB: 1F1T (Baugh et al. *J Mol Biol* 2000, 301, 117-28)) demonstrate the sequential increase in the fluorescence of MG dye. (d) Co-transcriptional assemblies of RNA nanorings (verified by native-PAGE, on top; Afonin et al. *Nano Lett* 2012, 12, 5192-5) functionalized with six MG aptamers visualized through the increase in the fluorescence of MG dye over the transcription time (bottom graph).

Figure 10:
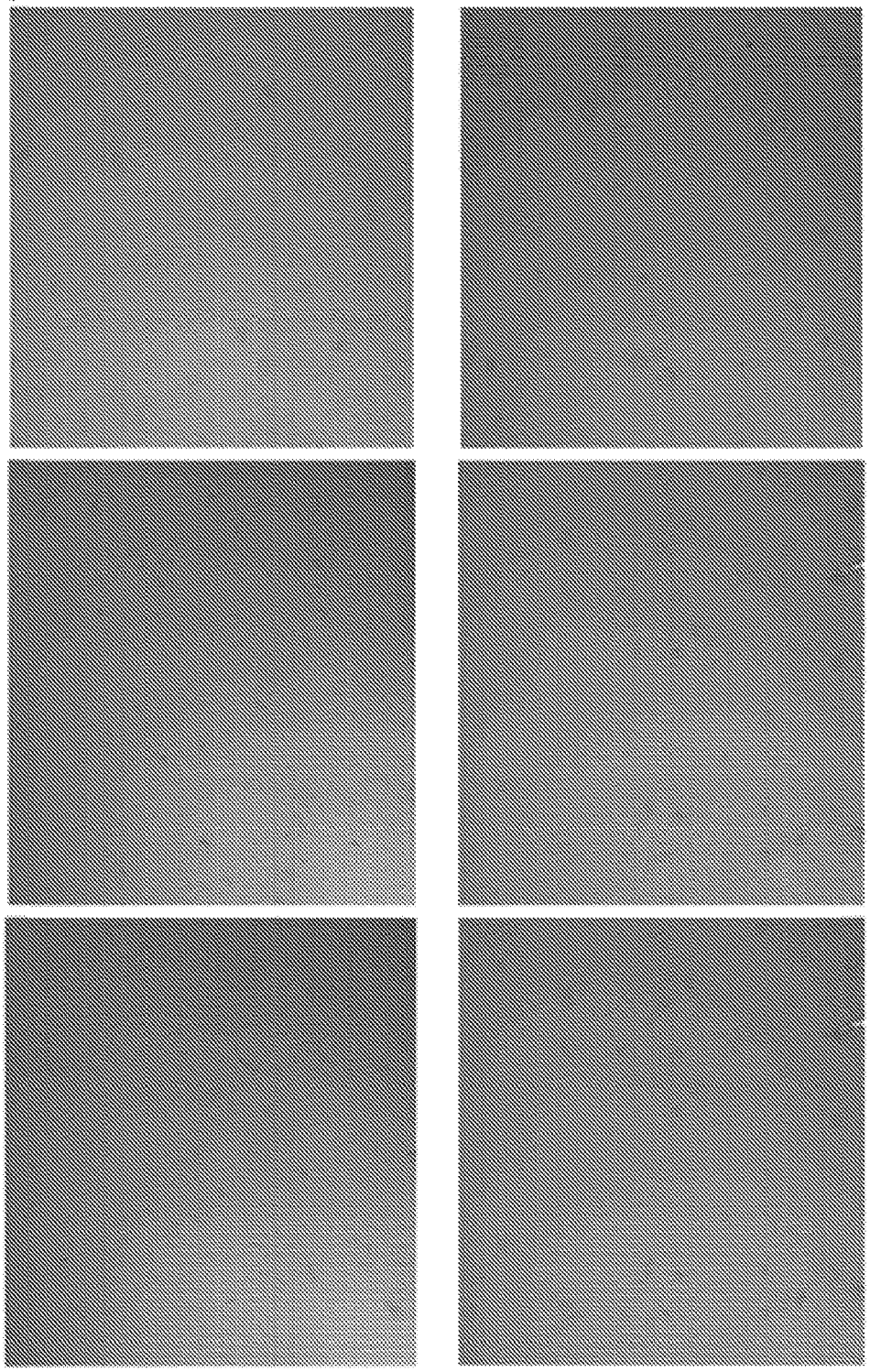

FIG. 10 shows relative transfection efficiencies for DS RNAs and nanorings functionalized with six DS RNAs. On the next day after the transfection of cells (~90% confluence) with DS RNAs and nanorings functionalized with six DS RNAs labeled with Alexa546, the efficiencies were analyzed by confocal fluorescence microscopy.

Figure 11:
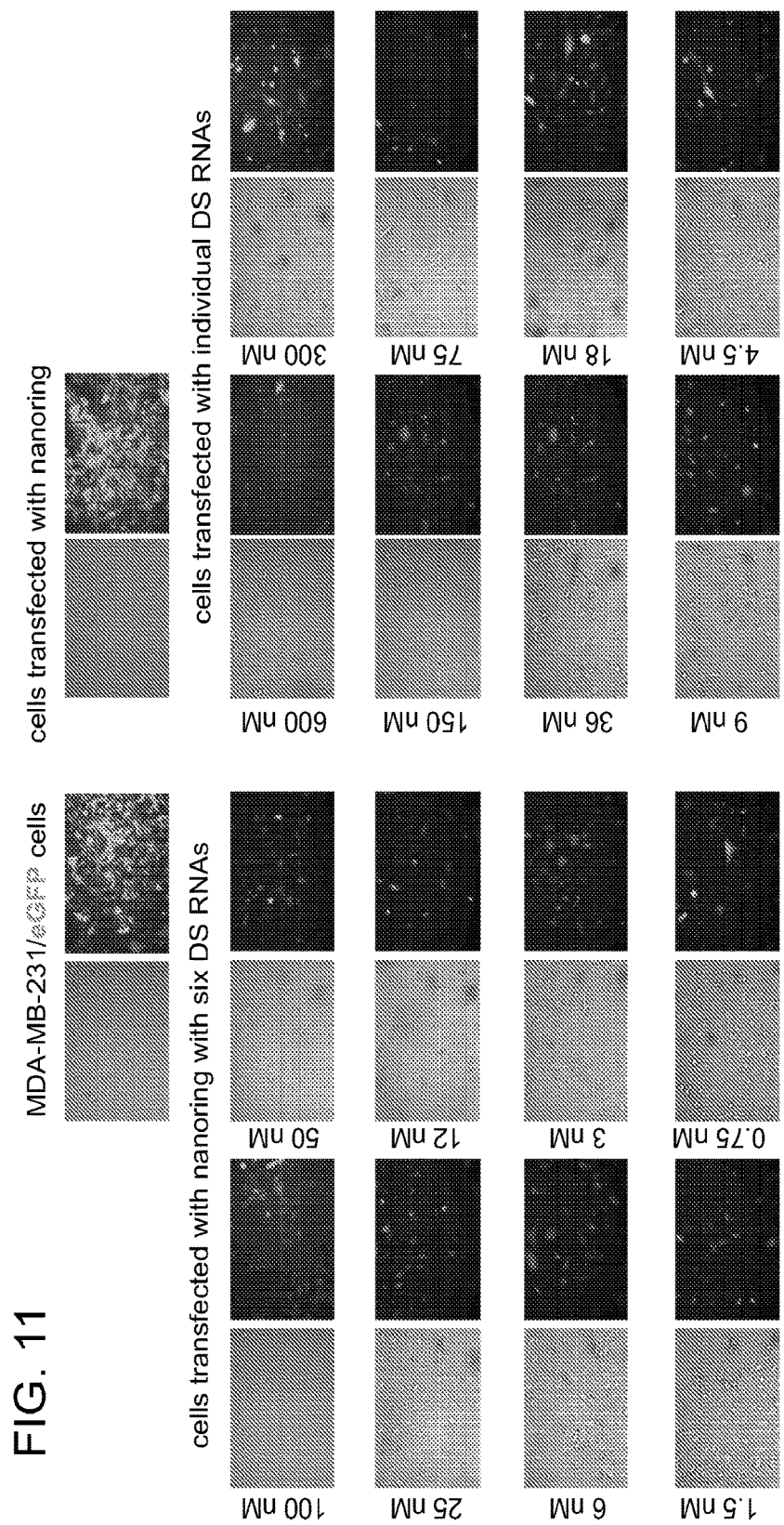
Figure 12A:
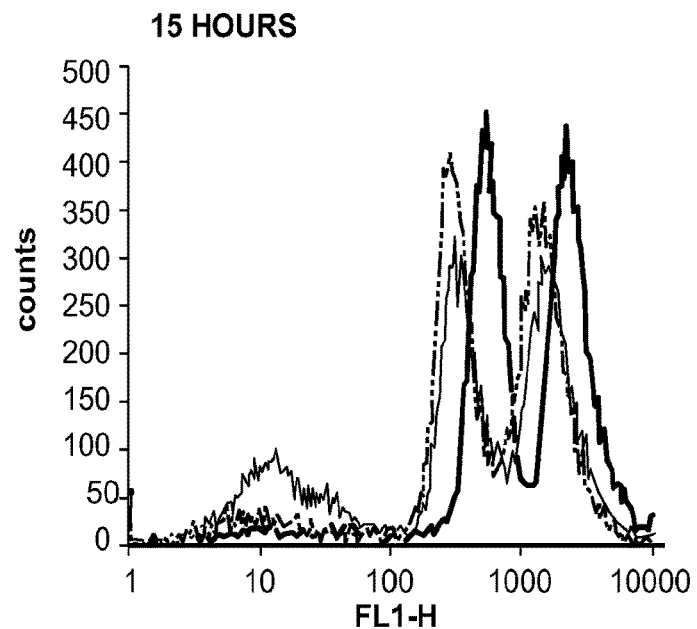
Figure 12B:
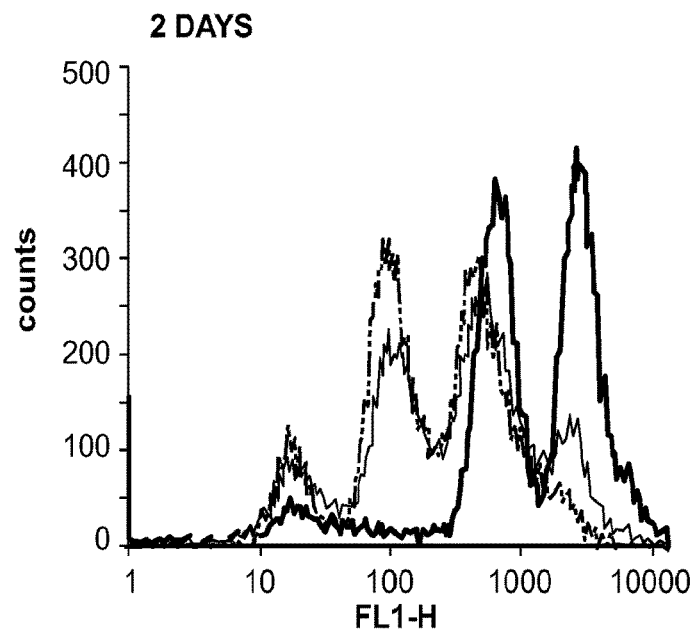
Figure 12E:
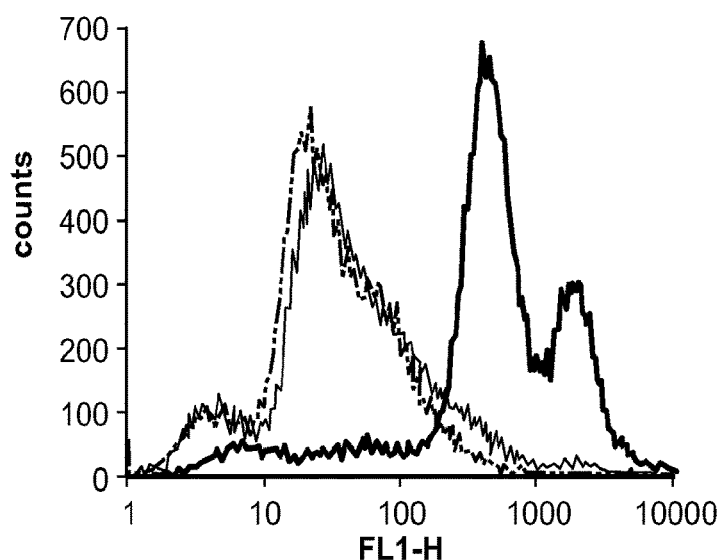
Figure 12F:
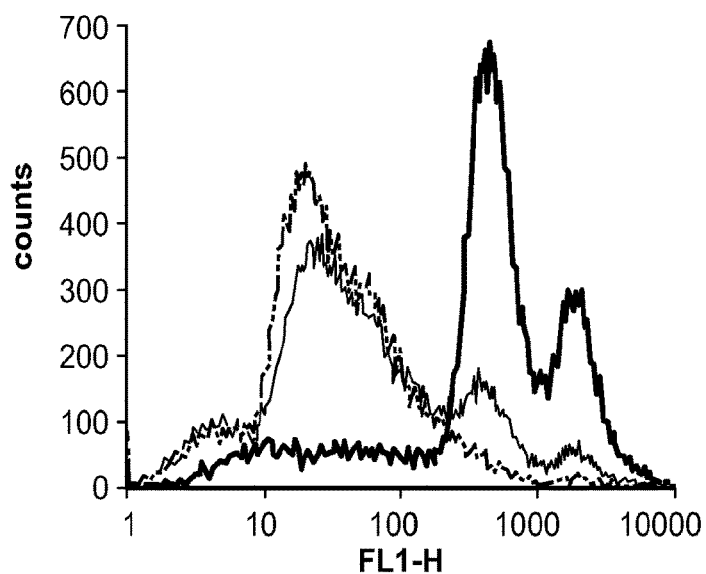
Figure 12G:
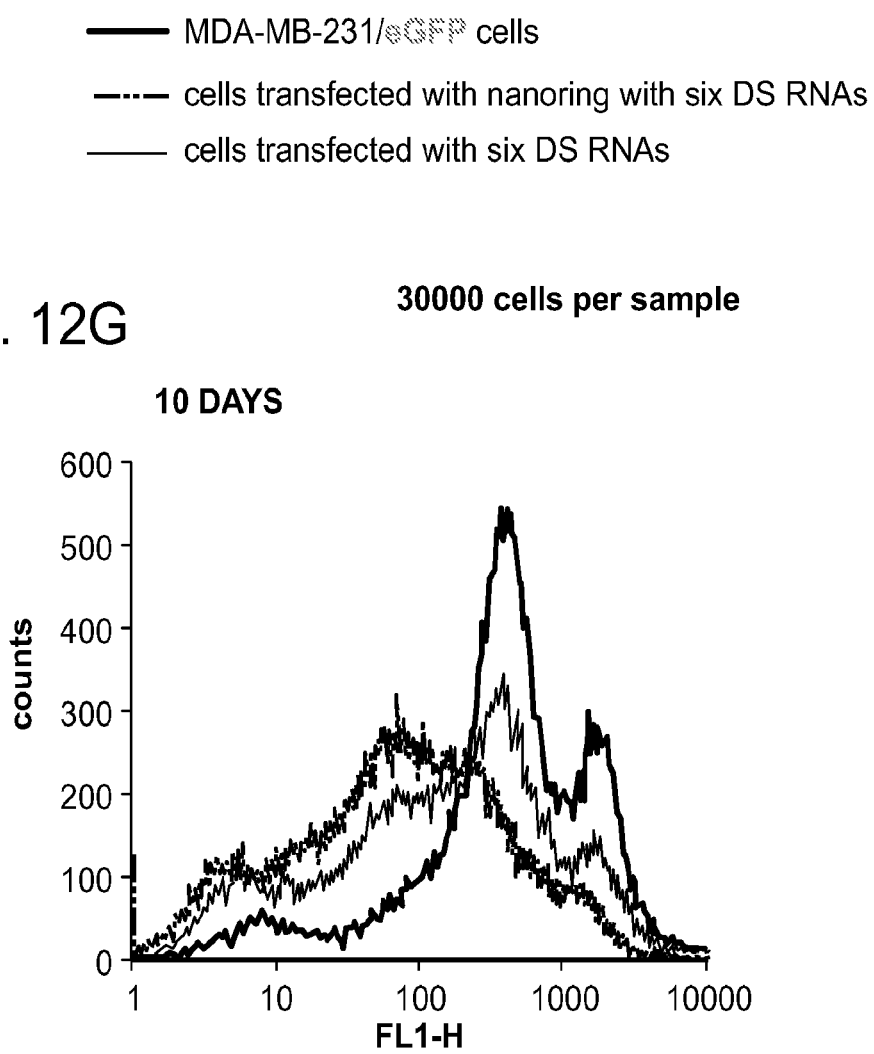

FIG. 11 shows GFP knockdown visualization assays for human breast cancer cells (MDA-MB-231) which stably express enhanced GFP (eGFP) transfected with different concentrations of nanorings functionalized with six DS RNAs (at 100, 50, 25, 12, 6, 3, 1.5, and 0.75 nM final) and DS RNA duplexes (at 600, 300, 150, 75, 30, 15, 9, and 4.5 nM final). Please note that due to the use of one-type of siRNA against eGFP, siRNA duplexes were transfected at six-fold higher concentrations compared to the corresponding functionalized nanorings. The relative levels of eGFP expression were visually analyzed for silencing of GFP expression with fluorescent microscopy three days post transfection. Please note that the total number of cells per randomly selected field may vary from sample to sample.

FIG. 12 shows GFP knockdown assays for human breast cancer cells (MDA-MB-231/GFP) which stably express enhanced GFP (eGFP) transfected with DS RNAs (at 6 nM final) and nanorings functionalized with six DS RNAs (at 1 nM final). The relative levels of eGFP expression were statistically (30000 cells) analyzed with flow cytometry experiments 15 hours, 2 days, 3 days, 4 days, 5 days, 6 days and 10 days post transfection.

FIGS. 13a to 13d show histograms and a FACs data plot for GFP knockdown experiments (a) GFP knockdown assays for human breast cancer cells (MDA-MB-231/GFP) which stably express enhanced GFP (eGFP) transfected with nanorings, nanorings functionalized with six DS RNAs against GFP and nanorings functionalized with six DS RNAs against GSTP1 at 100 nM each. (b) Cell viability assay conducted at different time points. Error bars denote SD, N=3. (c) GFP knockdown assays recorded at different time points for DS RNAs (at 6 nM) and nanorings functionalized with six DS RNAs (at 1 nM). The relative levels of eGFP expression were statistically (30000 cells) analyzed with flow cytometry experiments 1 day, 2 days, 5 days, 6 days, 7 days, 8 days and 9 days post transfection. (d) FACS data for corresponding non-normalized control cells at different time points. In (a) and (c), gMFI corresponds to the geometric mean fluorescence intensity. Error bars denote SEM.

FIGS. 14a to 14d show nanorings functionalized with J18 aptamers that bind specifically to target EGFR on A431 cells. (a) 3D model representing nanorings labeled with phycoerythrin (PE) and containing five J18 aptamers selected to specifically bind EGFR expressed on A431 cells. (b) Binding of NPs is mediated by RNA aptamers since the treatment with RNases resulted in a loss of the fluorescence signal. (c) The binding of monoclonal antibodies against EGFR. Simultaneous treatment using mAb against EGFR and RNases does not lead to loss of detection of EGFR, which confirms that loss of signal upon treatment with RNases is due to the degradation of RNA aptamers and not their target. (d) Competition of NP binding using rEGF resulted in a decrease of the signal as shown for a NP with one J18 aptamer. Also, the decrease of fluorescence was not caused by nonspecific degradation of RNA by the recombinant protein, because treatment with rIgG did not change the signal.

FIG. 15 shows functionalization of nanorings through toeholds interaction. (a) Schematic representation of assemblies leading to the formation of RNA nanorings functionalized with six DS RNAs via toehold interactions. (b) Native-PAGE results representing assemblies leading to the formations of RNA nanorings functionalized with six ssRNA toeholds and six DS RNAs. (c) GFP knockdown assays in human breast cancer cells (MDA-MB-231/GFP) which stably express enhanced GFP (eGFP). Statistical analysis (30000 cells per sample) of flow cytometry experiments of eGFP expression three days after the transfection of cells with nanorings carrying six toeholds and nanorings functionalized via toehold interactions with six DS RNAs against eGFP.

Figure 16:
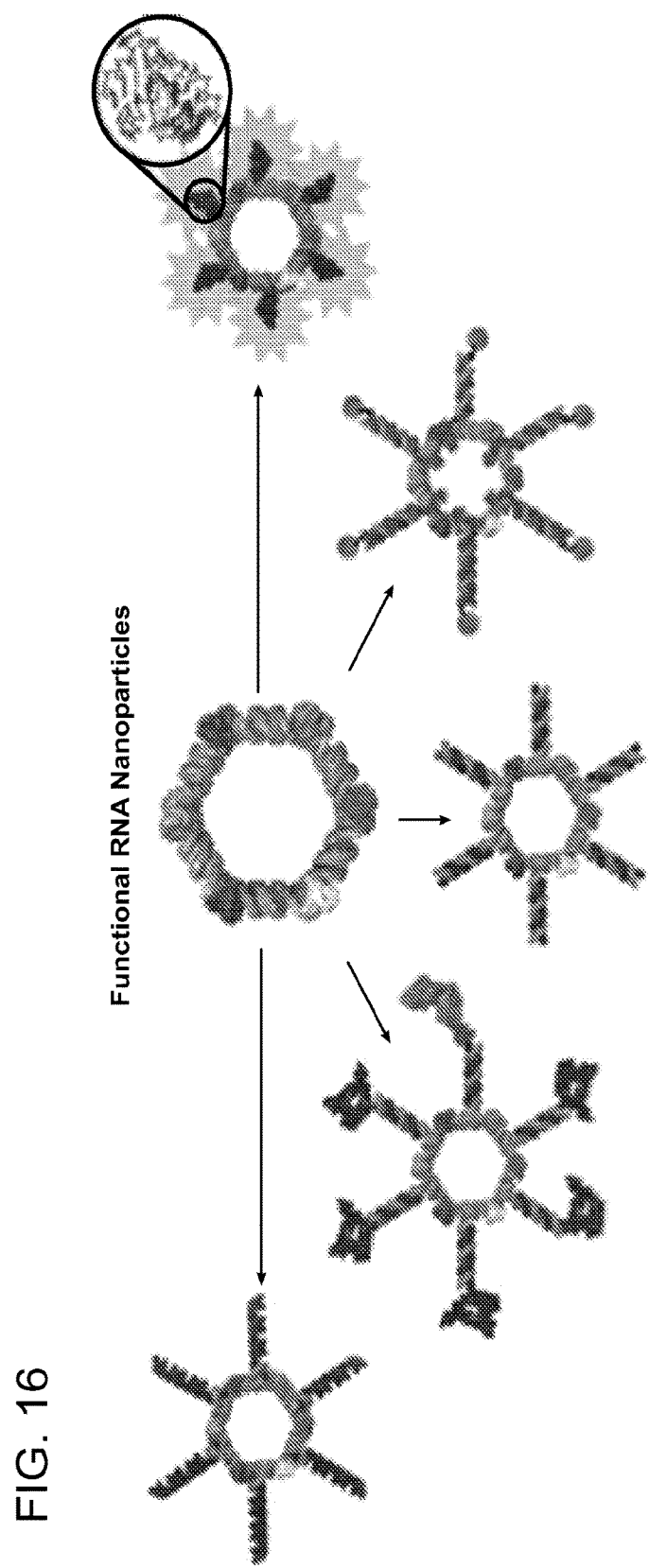

FIG. 16 is an additional image showing a range of functional RNA nanoparticles of the invention.

Figure 17A:
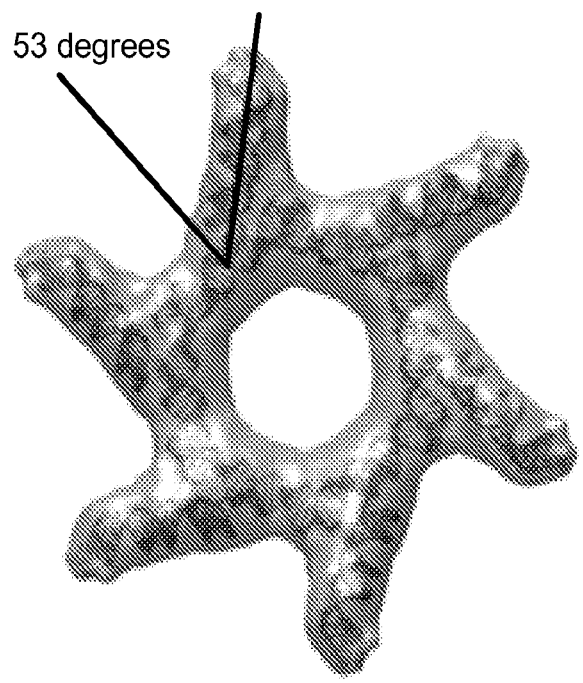
Figure 17B:
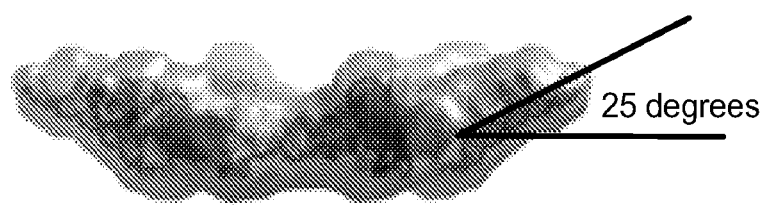
Figure 17C:
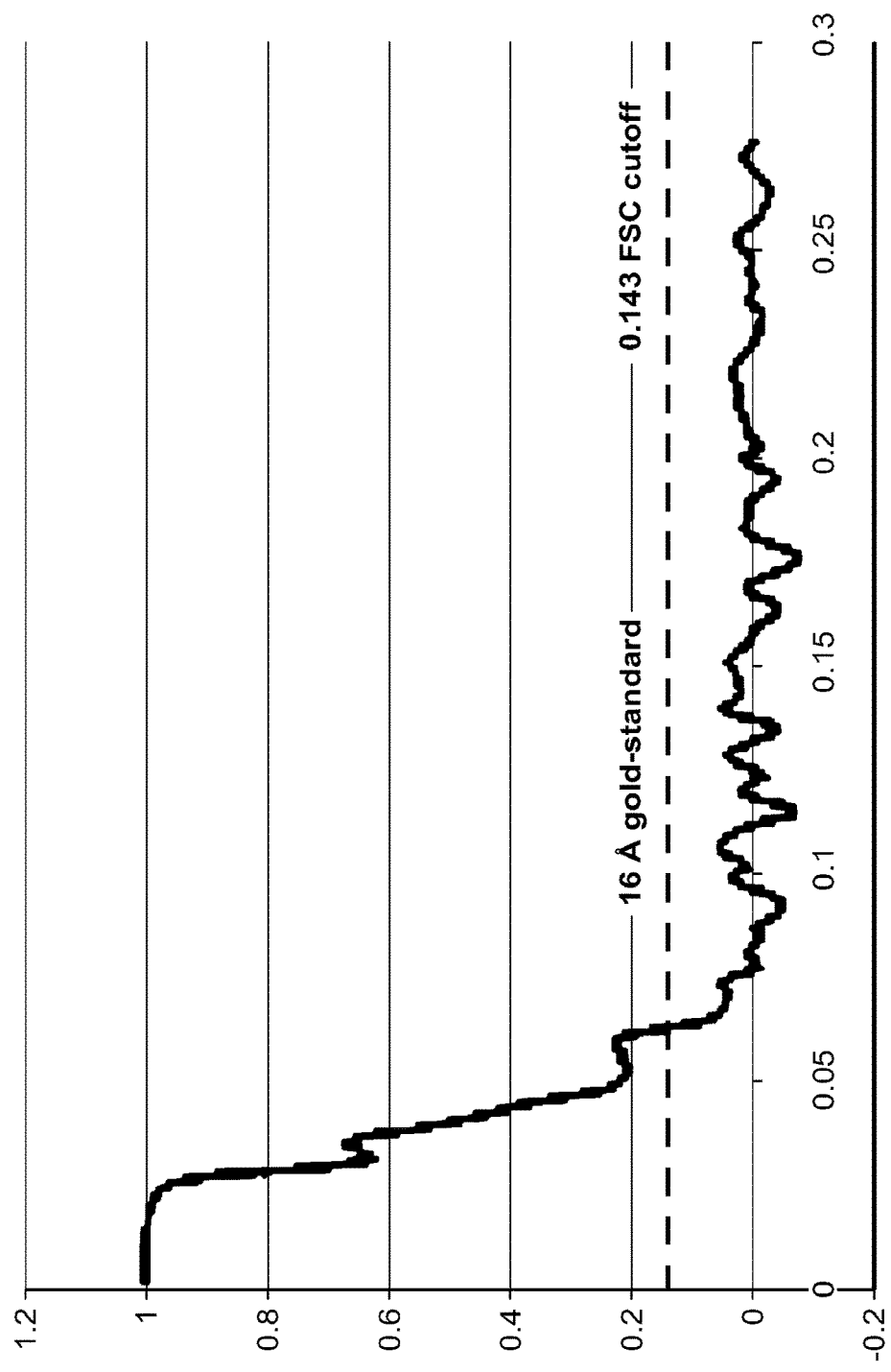

FIGS. 17a to 17c show Cryo-EM reconstruction, which demonstrated that the arms in the siRNA ring did not point straight out. (a) Looking from the top, the DS RNA arms were positioned in a pinwheel fashion around the ring. The six DS RNA arms pointed about 53 degrees clockwise compared to the arms in the FIG. 1 model. (b) Looking from the side, siRNA arms pointed about 25 degrees upward, thus creating a crown shape of the hexagonal molecule. (c) The resolution of the Cryo-EM density map was assessed to be 16 Å using the gold-standard criterion of Fourier Shell Correlation (FSC) cutoff at 0.143 from two independent half-sets of data.

Figure 18:
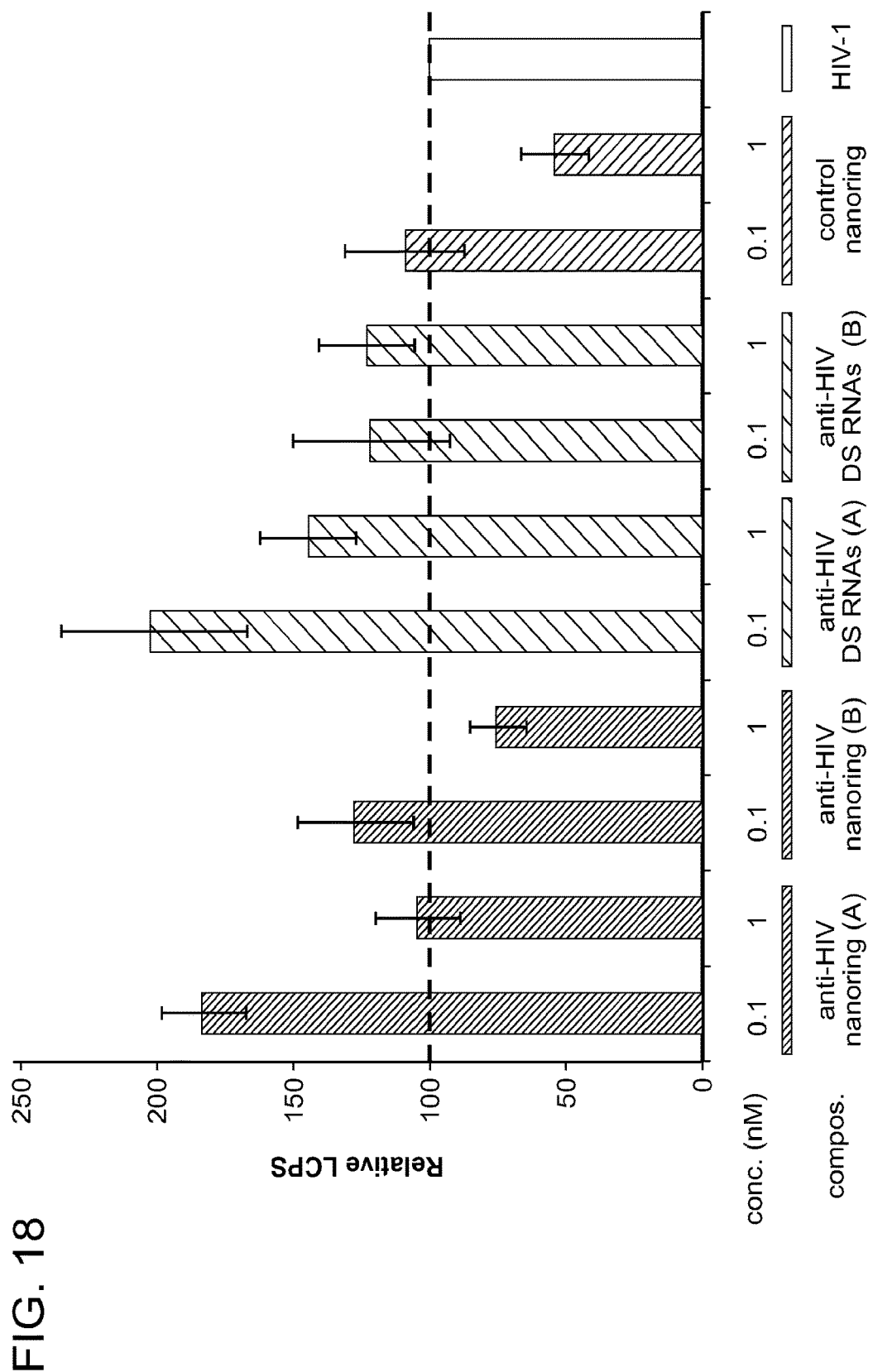

FIG. 18 shows an additional histogram demonstrating cytotoxicity of functional anti-HIV nanoring constructs A and B and controls (LCPS=luciferase counts per second) in HIV-1-expressing HeLa cells. Cytotoxicity was minimal at 1 nM of nanoring (B). Cells were co-transfected with pNL4-3 (HIV-1 molecular clone) and psiCHECK™-1 (Renilla Luciferase vector, Promega), with and without nanorings or dicer substrate (DS) RNAs. At 48 h post-transfection, cells were lysed and Renilla luciferase was measured. Data are shown normalized to virus controls (HIV-1). Anti-HIV DS RNAs (A and B), mixture of 6 different DS RNAs were used as positive control. Nanoring control had 6 copies of GSTP1 DS RNAs, and it was used as a negative control. HIV-1, Virus control. Error bars denote +/−SEM; N=4.

DETAILED DESCRIPTION OF THE INVENTION

The present invention is directed, at least in part, to the continued development of siRNA nanoscaffolds using nanorings to illustrate how this system can be designed to address several present challenges associated with NP-based siRNA delivery including cell-targeting, ease of synthesis, and triggered activation of therapeutic functionalities. The instant invention provides polyvalent RNA nanoparticles comprising one or more functionalities. These functionalized polyvalent RNA nanoparticles are suitable for therapeutic or diagnostic use in a number of diseases or disorders.

The RNA nanoparticles described herein have the ability to assemble, e.g., self-assemble, into higher order structures, e.g., a ring, a cage, or a nanotube. Methods and compositions of RNA nanoparticles that have the ability to assemble are described in US Publication US2012 0263648. The nanorings can be further designed to assemble into nanoarrays, nanocages and nanotubes via their dangling sticky tails. They can also be generated as polyvalent, multifunctional nanoparticles that can respond to environmental cues for biological and biomedical applications.

Advantageously, the nanoparticles of the instant invention provide a number of improvements over nanoparticles currently available. For example, the RNA nanoparticles of the invention may not induce a significant immune response like the protein nanoparticles currently used. Moreover, the nanoparticles of the invention are smaller than many currently available nanoparticles and therefore allow for increased efficiency of administration. The nanoparticles described herein comprise multiple RNA subunits each of which has the ability to bind an agent. Moreover, multiple different agents can be present within a single nanoparticle. Previous studies have shown that RNA nanostructures are effective drug delivery vehicles (see, for example, Khaled et al. (2005) Nano Letters 5:1797-1808).

The present invention exemplifies how the nanoring design can achieve cell-targeting properties through incorporation of RNA aptamers specific for the human Epidermal Growth Factor Receptor (EGFR). The incorporation of RNA functionalities such aptamers or Dicer substrate (DS) RNAs into the nanoscaffolds presents difficulties in terms of solid state chemical synthesis as RNA components generally cannot exceed 60 nucleotides in length. The present invention addresses this problem by annealing both RNA aptamers and dicer substrate RNAs to the nanoscaffolds using single-stranded toehold recognition sites. This system of attachment allows for the multi-functional use of a single nanoscaffold since different nucleic acid functionalities can be joined as long as it bears the cognate toehold complementary to the one found in the nanoscaffold. The present invention also demonstrates how the therapeutic functionality of the nanoring can be triggered through incorporation of RNA/DNA hybrids. This newly developed technique involves splitting the RNA-based functionality of interest, in this case the dicer-substrate RNAs, between a RNA/DNA nanoring and RNA/DNA hybrid. The DNA strands contain complementary toeholds, which when in close proximity, bind to one another allowing for reassociation of the DS RNAs within the nanoring along with DNA duplexes as the byproduct. Only when the dicer-substrate RNAs have formed will gene silencing occur, which allows for an additional degree of control over when the therapeutic becomes active. The enhancements to the RNA nanoring system described herein are meant to address several of the challenges remaining in using this technology for a clinical application.

Definitions

The instant invention provides polyvalent RNA nanoparticles comprising RNA motifs as building blocks. The polyvalent RNA nanoparticles described herein can further comprise therapeutic, diagnostic and/or delivery agents. Further, the polyvalent RNA nanoparticles described herein can be used as drug delivery compositions to treat various diseases or conditions.

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, the term "functionalities" refers to substances which are capable of being contained in, or attached, to the nanoparticle. In exemplary embodiments, a functionality is an agent. Exemplary agents include, for example, prodrugs, diagnostic agents, imaging agents, therapeutic agents, chemotherapeutic agents, pharmaceutical agents, drugs, synthetic organic molecules, proteins, peptides, vitamins, and steroids, siRNAs, RNA or DNA aptamers, fluorescent dyes, small molecules, RNA-DNA hybrids with split functionalities, split lipase, split GFP and proteins.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or a by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

As used herein, the term "therapeutic agent" is meant to refer to an agent that is capable of exerting an effect on a target, in vitro or in vivo.

As used herein, the term "chemotherapeutic agent" is meant to include a compound or molecule that can be used to treat or prevent a cancer. A "chemotherapeutic agent" is meant to include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

As used herein, the term "effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with a particular disease or disorder. A physician or veterinarian of ordinary skill can readily determine and prescribe the effective amount of the bioactive agent required to treat and/or prevent the progress of the condition.

As used herein, the term "cancer" is used to mean a condition in which a cell in a subject's body undergoes abnormal, uncontrolled proliferation. Thus, "cancer" is a cell-proliferative disorder. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The terms "cancer," "neoplasm," and "tumor," are used interchangeably and in either the singular or plural form, refer to cells that have undergone a malignant transformation that makes them pathological to the host organism. By "neoplastic cell" is meant a cell that is a component of a neoplasia.

As used herein, a "composition" refers to the combination of an active agent (e.g., a polyvalent RNA nanoparticle). The composition additionally can comprise a pharmaceutically acceptable carrier or excipient and/or one or more therapeutic agents for use in vitro or in vivo.

As used herein, the term "conjugated" is understood as attached, linked, or otherwise present on a nanoparticle.

As used herein, "disease" is meant to refer to any condition or disorder that damages or interferes with the normal function of a cell, tissue, or organ.

As used herein, "effective amount" is meant to refer to the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

As used herein, "inhibits neoplasia" is meant decreases the propensity of a cell to develop into neoplasia or slows, decreases, or stabilizes the growth or proliferation of a neoplasia.

As used herein, "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

As used herein, "kits" are understood to contain at least the non-standard laboratory reagents of the invention and one or more non-standard laboratory reagents for use in the methods of the invention.

As used herein, the term "nanoparticle" is meant to refer to a particle between 10 nm and 200 nm in size. A nanoparticle according to the invention comprises a ribonucleic acid (RNA). The RNA can be obtained from any source, for example bacteriophages phi 29, HIV, Drosophila, the ribosome, or be a synthetic RNA.

The term "obtaining" is understood herein as manufacturing, purchasing, or otherwise coming into possession of.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Oligionucleotides can have inhibitory activity or stimulatory activity.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

The term "toehold" refers to nucleation site of a domain comprising a nucleic acid sequence designed to initiate hybridization of the domain with a complementary nucleic acid sequence.

As used herein, the term "therapeutic agent" includes a drug and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, devices, diagnostics and contraceptives, including preparations useful in clinical screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes. Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a growth factor, e.g., NGF or GNDF, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

As used herein, the term "treated," "treating" or "treatment" includes the diminishment or alleviation of at least one symptom associated or caused by the state, disorder or disease being treated. A subject that has been treated can exhibit a partial or total alleviation of symptoms (for example, tumor load), or symptoms can remain static following treatment according to the invention. The term "treatment" is intended to encompass prophylaxis, therapy and cure.

As used here, the phrase "5' or 3' sticky ends" is meant to refer to the 3' and/or 5' protruding ends of DNA or RNA that will bond with complementary sequences of bases. In certain embodiments, the RNA motifs have 5' or 3' sticky ends. In certain embodiments, the 5' or 3' sticky ends are located in the middle of a helix. According to the invention, the 5' and 3' sticky ends can be engineered to be used for self-assembly of the nanorings into an RNA nanotube.

Other definitions appear in context throughout the disclosure.

RNA and Nanostructure Design

RNA has a number of advantages for nanostructure design. Nanoparticle structures provide a size range that is large enough to avoid the problem of expulsion from the cell, but are small enough to avoid the problems of cell delivery often encountered with larger particles. RNA is the only biopolymer that can carry genetic information and has catalytic properties. RNA can naturally fold into complex motifs, and RNA motifs are capable of self-assembly. RNA has a natural functionality, for instance RNA can function as ribozymes or riboswitches. Further, RNA is advantageous in eliciting a very low immune response. Moreover, the construction of RNA into ordered, patterned superstructures has a number of desirable characteristics, including the ability to self-assemble in precisely defined ways, the ability to undergo editing and replication, the ability to undergo controlled disassembly. RNA has versatility in function and structure. Functionally, RNA is the only biopolymer that can carry genetic information and that possesses catalytic properties. Structurally, RNA has predictable intra and intermolecular interactions with well-known structural geometry. The RNA strands that consist of adenine (A), guanine (G), cytosine (C), and uridine (U) can naturally, or can be programmed, to self-assemble via complementary base pairing. The helical region of RNA has a well-known nanometer scale structural geometry of 2.86 nm per helical turn with 11 base pairs and a 2.3 nm diameter. The self-assembly of RNA into complex structures can be facilitated via complementary base pairing or inter- and intra-molecular interactions of the different single stranded regions in the RNA, including internal bulges and loop motifs, and single-stranded overhangs or "sticky-ends". In addition to Watson-Crick base pairing, A, G, C and T can also pair with other, unconventional bases (i.e. non-canonical base-pairing).

The methods of the invention can be used to assemble RNA NPs composed of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123, 124, 125 or more distinct RNA strands RNA Synthesis RNA molecules used to make the nanoparticles of the invention can be produced recombinantly or synthetically by methods that are routine for one of skill in the art. For example, synthetic RNA molecules can be made as described in US Patent Application Publication No.: 20020161219, or U.S. Pat. Nos. 6,469,158, 5,466,586, 5,281,781, or 6,787,305.

RNA Self-Assembly

Small RNA structural motifs can code the precise topology of large molecular architectures. It has been shown that RNA structural motifs participate in a predictable manner to stabilize, position and pack RNA helices without the need of proteins (Chworos A et al., Science 306:2068-2072.2004). RNAI and RNAII are loop structures that interact in what is called a 'kiss' or 'kissing' complex (Lee et al., Structure 6:993-1005.1998). This contact facilitates the pairing of the RNAI and RNAII loops, until the two RNAs form a duplex. As such, the "kissing" interaction between RNAI and RNAII is one means of self-assembly between the RNA building blocks. The interaction between the RNAIi/RNAIIi complex involves all the bases in the base pairing, and dissociates nearly 7000 times more slowly than the wild-type complex.

The self-assembly of nanoparticles from RNA involves cooperative interaction of individual RNA molecules that spontaneously assemble in a predefined manner to form a larger two- or three-dimensional structure. Within the realm of self-assembly two main categories have been described: template and non-template (Lee et al. J Nanosci Nanotechnol. 2005 December; 5(12):1964-82). Template assembly involves interaction of RNA molecules under the influence of specific external sequence, forces, or spatial constraints such as RNA transcription, hybridization, replication, annealing, molding, or replicas. In contrast, non-template assembly involves formation of a larger structure by individual components without the influence of external forces. Examples of non-template assembly are ligation, chemical conjugation, covalent linkage, and loop/loop interaction of RNA, especially the formation of RNA multimeric complexes (Lee et al. 2005, as above).

Previously, RNA has been demonstrated to assemble into nanoparticles of various shapes and sizes. The first RNA nanoparticles were generated using loop-receptor interfaces to form dimeric nanoparticles. The assembly of this H-shaped nanoparticle was mediated by GAAA/Hnt receptor interaction, which is a highly recurrent motif found in group I and group II introns and other ribozymes and riboswitches. This interaction was further used to generate oriented filaments by combining multiple loop-receptor interactions with a four-way junction motif. One of the first examples of RNA nanoparticles that incorporate multiple RNA motifs within its context is the tectosquare, which is composed of four artificial RNA building blocks called tectoRNAs that self-assemble through specific, non-covalent loop-loop interactions called kissing loops (KL) found at the end of each stem. These tectoRNAs were further programmed to self-assemble into complex arrays via 3' sticky tails with controllable topology, directionality and geometry. The first example of a therapeutic RNA nanoparticle was designed from phi-29-encoded packaging motor (pRNA), a natural RNA motif found in bacteriophages. The pRNA dimers were reengineered for targeted delivery of ribozymes to attack the hepatitis B virus by specifically cleaving the virus's poly-A signal. In a subsequent study, the pRNA trimers were functionalized with cell receptor-binding RNA aptamers and were used to deliver siRNAs that target a specific gene for silencing and thus enabling apoptosis in cancer cells.

In certain embodiments the RNA building blocks of the invention can self-assemble in buffer conditions suitable for RNA, and that can be determined by one of skill in the art. In other certain embodiments, the nanostructures of the invention can be formed in a cell. In certain examples, the RNA sequence will be expressed in the cell and formation of the nanoparticle will be observed via electron microscope tomography (EMT). To satisfy the EMT resolution requirements the minimal size of the nanoparticle will be between 15 nm, 20 nm, 25 nm, 30, nm, 35 nm, 40 nm, 45 nm or more. In preferred embodiments, the minimal size of the nanoparticle will be 25 nm. Moreover, in preferred embodiments, the nanoparticle can further assemble into bundles, such as nanotubes, sheets, or clusters.

RNA Nanoparticles

Using natural or artificially selected RNA motifs and modules, RNA molecules can be programmed to form a wide variety of compact and stable artificial three-dimensional nanostructures (called RNA NPs; Afonin et al. Accounts of Chemical Research 2014, dx.doi.org/10.1021/ar400329z; Afonin et al. Nat Nanotechnol 2010, 5, (9), 676-82; Severcan et al. Nat Chem 2010, 2, (9), 772-9; Grabow et al. Nano Lett 2011, 11, (2), 878-87; Guo et al., M. Mol Cell 1998, 2, (1), 149-55) suitable for the broad range of clinical and nanotechnological applications (Afonin et al. Accounts of Chemical Research 2014, dx.doi.org/10.1021/ar400329z; Afonin et al. *Nat Protoc* 2011, 6, (12), 2022-34; Guo, P. *Nat Nanotechnol* 2010, 5, (12), 833-42; Shukla et al. *ACS Nano* 2011, 5, (5), 3405-3418; Shu et al. *Rna* 2013, 19, (6), 767-77; Koyfman et al. *J Am Chem Soc* 2005, 127, (34), 11886-7; Shu et al. *Adv Drug Deliv Rev* 2014, 66C, 74-89; Khisamutdinov et al. *ACS Nano* 2014; Hao et al. *Nat Commun* 2014, 5, 3890; Ohno et al. *Nat Nanotechnol* 2011, 6, (2), 116-20; Osada et al. *ACS Nano* 2014; Haque et al. *Nano Today* 2012, 7, (4), 245-257; Tarapore et al. *Mol Ther* 2011, 19, (2), 386-94). Therapeutic nucleic acids, proteins, or small molecules can be individually attached using different techniques (Shu et al. *Adv Drug Deliv Rev* 2014, 66C, 74-89) to programmable RNA monomers entering the composition of RNA NP. The assembly of the monomers will bring the desired functionalities together, thus providing precise control over their topology, composition, and modularity. The use of functional RNA NP in vivo will guarantee higher concentration and desired stoichiometry of therapeutic moieties locally.

Herein, new multifunctional RNA NPs built based on previously designed RNA nanorings (Grabow et al. *Nano Lett* 2011, 11, (2), 878-87; Yingling and Shapiro. *Nano Lett* 2007, 7, (8), 2328-34) were identified, with the inventions illustrating how this system can be used to address several present challenges associated with RNA NPs including functionalization with different classes of molecules such as multiple siRNAs (FIG. 1a), aptamers (FIG. 1e), proteins (FIG. 1f), and small molecules (FIG. 1h). Detailed characterization of the resulting functional RNA NPs in vitro (by native-PAGE, DLS, cryo-EM, and fluorescent studies), in various cell cultures and in vivo was demonstrated.

How the nanoring design can achieve cell-targeting properties through incorporation of RNA aptamers specific for the human Epidermal Growth Factor Receptor, EGFR (FIG. 1f) has also been disclosed herein. EGFR is highly overexpressed on the surface of a number of cancer cell types, which has made it an ideal candidate for targeting through aptamer-mediated delivery of cancer therapeutics (Li et al. *J Proteome Res* 2009, 8, (5), 2438-48). DNA nanostructures (Koyfman et al. *Langmuir* 2009, 25, (2), 1091-6) were previously targeted to cancer cell lines and specifically attached through antibodies to EGF Receptors to bridge multiple cells and create cellular assemblies (Koyfman et al. *J Am Chem Soc* 2009, 131, (40), 14237-9).

The incorporation of RNA functionalities such as Dicer Substrate (DS) RNAs (Rose et al. *Nucleic Acids Res* 2005, 33, (13), 4140-56) into the nanoscaffolds presented difficulties in terms of solid state chemical synthesis as RNA components generally cannot exceed ~60 nucleotides in length. This problem was addressed by annealing DS RNAs to the nanoscaffolds using single-stranded toehold recognition sites (FIG. 1g).

Lastly, it has been established herein how the therapeutic functionality of the nanoring can be triggered through the incorporation of RNA-DNA hybrids (FIG. 1h). This newly developed technique (Afonin et al. *Nat Nanotechnol* 2013, 8, (4), 296-304; Afonin et al. *Acc Chem Res* 2014) involves splitting the different functionalities between a RNA-DNA nanoring and cognate RNA-DNA hybrids with further conditional intracellular activation of these functionalities.

RNA has been demonstrated to be an efficient nanoparticle (Afonin et al. RNA Nanotechnology. 1: 1-15, 2013; Kasprzak et al. In: RNA Nanotechnology and Therapeutics. Florida: CRC Press; 2013. p. 139-158; Grabow et al., Recent Advances in Nanoscience and Nanotechnology). Volume 1. New Jersey: Apple Academic Press; 2012. p. 208-220; Shukla et al. ACS Nano. 5: 3405-3418, 2011; Afonin et al. Nat Nanotechnol. 5: 676-82, 2010). A bacteriophage phi29-encoded RNA (pRNA) has been reengineered to form dimmers, trimers, rods, hexamers, and 3D arrays several microns in size through interactions of interlocking loops (Shu, D.; Moll, W.-D.; Deng, Z.; Mao, C.; Guo, P. *Nano Letters* 2004, 4, (9), 1717-1723; Guo, P. *J Nanosci Nanotechnol* 2005, 5, (12), 1964-82). A nanoparticle, containing a pRNA trimer as a delivery vehicle was used to deliver siRNAs and receptor-binding aptamers, and has been demonstrated to block cancer development both in vitro in cell culture, and in vivo in mice (Khaled, A.; Guo, S.; Li, F.; Guo, P. *Nano Lett* 2005, 5, (9), 1797-808; Guo, S.; Huang, F.; Guo, P. *Gene Ther* 2006, 13, (10), 814-20). An H-shaped RNA molecular unit built from a portion of group I intron domain has been shown to form oriented filaments (Hansma, H. G.; Oroudjev, E.; Baudrey, S.; Jaeger, L. *J Microsc* 2003, 212, (Pt 3), 273-9; Nasalean, L.; Baudrey, S.; Leontis, N. B.; Jaeger, L. *Nucleic Acids Res* 2006, 34, (5), 1381-92). Further, specific RNA nano-arrangements based on HIV dimerization initiation site stem-loops were shown to be capable of thermal isomerization to alternative structures (Horiya, S.; Li, X.; Kawai, G.; Saito, R.; Katoh, A.; Kobayashi, K.; Harada, K. *Nucleic Acids Res Suppl* 2002, (2), 41-2; Horiya, S.; Li, X.; Kawai, G.; Saito, R.; Katoh, A.; Kobayashi, K.; Harada, K. *Chem Biol* 2003, 10, (7), 645-54; Li, X.; Horiya, S.; Harada, K. *J Am Chem Soc* 2006, 128, (12), 4035-40). Small structural fragments found in the ribosome and HIV have been used in the design of artificial RNA building blocks, called tectoRNAs (Chworos, A.; Severcan, I.; Koyfman, A. Y.; Weinkam, P.; Oroudjev, E.; Hansma, H. G.; Jaeger, L. *Science* 2004, 306, (5704), 2068-72). Each tectoRNA contains a right angle motif that forms a 90-degree angle between adjacent helices, two interacting hairpin loops at the end of each stem, and a 3' "sticky stem". The hairpin loops direct the formation of the tetramer via formation of specific noncovalent loop-loop interactions, called "kissing loops", and the "sticky stems" further assemble tetramers into complex nanoarrays. In bionanotechnology, RNA-RNA interactions can guide precise deposition of gold nanoparticles (Bates, A. D.; Callen, B. P.; Cooper, J. M.; Cosstick, R.; Geary, C.; Glidle, A.; Jaeger, L.; Pearson, J. L.; Proupin-Perez, M.; Xu, C.; Cumming, D. R. *Nano Lett* 2006, 6, (3), 445-8). Design and self-assembly of siRNA-functionalized RNA nanoparticles for use in automated nanomedicine has been described (Afonin et al. Nat Protoc. 6: 2022-34, 2011). Self-assembling tectoRNA-ladders have been shown to induce a precise linear arrangement of cationic gold nanoparticles, demonstrating that RNA can control regular spacing of gold nanoparticles and can act as a nanocrown scaffold (Koyfman, A. Y.; Braun, G.; Magonov, S.; Chworos, A.; Reich, N. O.; Jaeger, L. *J Am Chem Soc* 2005, 127, (34), 11886-7). Activation of different split functionalities on re-association of RNA-DNA hybrids has been described (Afonin et al. Nat Nanotechnol. 8: 296-304, 2013). In Silico, In Vitro, and In Vivo studies have indicated the potential use of bolaamphiphiles for therapeutic siRNAs Delivery (Kim et al. Mol Ther Nucleic Acids. 2: e80, 2013). A generalized methodology for the one-pot production of chemically modified functional RNA nanoparticles during in vitro transcription with T7 RNA polymerase has been described (Afonin et al. Nano Lett. 12: 5192-5195, 2012). The role of salt concentration and magnesium binding in HIV-1 subtype-A and subtype-B kissing loop monomer structures has been described (Kim et al. J Biomol Struct Dyn. 2013; 31(5):495-510). Self-assembling RNA nanorings based on RNAI/II inverse kissing complexes have been described (Grabow et al. Nano Lett. 11: 878-87, 2011). RNA structure flexibility data has been used in nanostructure modeling (Kasprzak et al. Methods. 54: 239-250, 2011). Coarse-graining RNA nanostructures have been used for molecular dynamics simulations (Paliy et al. Phys Biol. 7(3): 036001, 2010). Characterization of structural features for small regulatory RNAs in *Escherichia coli* genomes have been reported (Le et al. IEEE Conference on Bioinformatics and Biomedicine, BIBM 2010). Computational and experimental RNA nanoparticle design has been reported (Severcan et al. In: Automation in Genomics and Proteomics: An Engineering Case-Based Approach), and a mesoscopic model for molecular dynamics studies of RNA nanostructures has been described (Paliy et al. 8th Annual International Conference on Computational Systems Bioinformatics Volume 8. Aug. 10-12, 2009; Stanford University, Palo Alto, Calif. p. 71-79).

In addition to functionalization with multiple different short interfering RNAs for combinatorial RNA interference (e.g. against multiple HIV-1 genes), nanorings of the invention also allow simultaneous embedment of assorted RNA aptamers, fluorescent dyes, proteins, as well as recently developed RNA-DNA hybrids aimed to conditionally activate multiple split functionalities inside cells.

Improving the quality of life in modern society promotes longer life expectancies of the population. Consequently, the chance of contracting a serious infection or illness increases. Lately, there is considerable hope that nanotechnologies will provide new, revolutionary approaches for the detection and therapy of different life-threatening diseases. Nanotechnology promises to completely change, for example, the way cancer is diagnosed and treated, by substantially increasing the concentrations of drugs delivered to the targets while minimizing their toxicity (Farokhzad and Langer. ACS Nano 2009, 3, (1), 16-20; Petros and DeSimone. Nat Rev Drug Discov 2010, 9, (8), 615-27).

The use of inorganic or synthetic materials to produce nanoparticles (NPs) for diagnostics and treatment is often accompanied by high levels of endotoxin content and sterility issues coming from commercial starting materials or residual manufacturing components (Crist et al. Integr Biol (Camb) 2013, 5, (1), 66-73; Moghimi et al. Annu Rev Pharmacol Toxicol 2012, 52, 481-503). Therefore, these NPs require additional purification or re-manufacturing even before initiating pre-clinical studies. Another problem with some synthetic and inorganic compounds is their bioincompatibility and accumulation in the human body which may cause some health complications later in a patient's life (Petros and DeSimone. Nat Rev Drug Discov 2010, 9, (8), 615-27; Moghimi et al. Annu Rev Pharmacol Toxicol 2012, 52, 481-503). The use of biological materials (such as RNA or DNA) for drug formulation may become the next big step in NP therapy development. Also, over the past few years, the total number of RNA interference (RNAi)-based preclinical and clinical trials has increased significantly (Chen and Xie. J. Int J Nanomedicine 2012, 7, 3971-80). RNAi is a naturally occurring cellular post-transcriptional gene regulation process employing small double-stranded RNAs to direct and trigger homology dependent gene silencing (Fire et al. Nature 1998, 391, (6669), 806-11). The RNAi machinery is increasingly being harnessed for therapeutic gene modulation and treatment of various diseases through the exogenous introduction of short synthetic RNA duplexes called small-interfering RNAs (siRNAs) (Bramsen and Kjems. Front Genet 2012, 3, (154)). Currently, more than 20 different therapeutic siRNAs are in clinical trials (Zhou et al. Pharmaceuticals (Basel) 2013, 6, (1), 85-107). Besides specific siRNAs (or micro-RNAs), several other promising therapeutically potent RNA classes such as antisenses, aptamers, and ribozymes are worthy of consideration. Simultaneous use of multiple different RNA therapeutics is expected to have significant synergistic effects. One of the well-known examples, is combinatorial RNAi used for highly effective simultaneous multiple gene suppression preventing the possibility of mutation-assisted escape from RNAi (e.g. in the case of HIV)(Grimm and Kay. Mol Ther 2007, 15, (5), 878-88).

Design

The general approach used to create RNA nano-particles and nano-materials is to take known RNA structures, cut them into the building blocks, and reengineer single-stranded loops and regions to facilitate the desired self-assembly. The self-assembly of all the above discussed RNA building blocks into nanostructures is mediated by the complementarity of hairpin loops and loop receptors that form non-covalent RNA-RNA interactions. For precise assembly of the RNA building blocks, each of the corresponding complementary loop-loop interactions are uniquely reengineered.

Two main experimental approaches are used for programmable self-assembly of nucleic acids nanostructures (Jaeger, L.; Chworos, A. Curr Opin Struct Biol 2006, 16, (4), 531-43). The first is a single-step assembly, which is commonly used for DNA nanostructures (Chelyapov, N.; Brun, Y.; Gopalkrishnan, M.; Reishus, D.; Shaw, B.; Adleman, L. J Am Chem Soc 2004, 126, (43), 13924-5; Mathieu, F.; Liao, S.; Kopatsch, J.; Wang, T.; Mao, C.; Seeman, N. C. Nano Lett 2005, 5, (4), 661-5.). The second is a stepwise assembly, which has been commonly described for RNA nanostructures (Chworos, A.; Severcan, I.; Koyfman, A. Y.; Weinkam, P.; Oroudjev, E.; Hansma, H. G.; Jaeger, L. Science 2004, 306, (5704), 2068-72). In the single-step assembly approach, all molecules are mixed together followed by the slow cool annealing procedure. This is only possible if the target building block structure is the one that has the highest number of Watson-Crick base pairs and is therefore the most stable. However, it is understood that thermodynamic stability of different shapes of nanoparticles is also an important consideration, at times more so than Watson base pairing. This approach is, thus, based on the preferential folding of the building blocks at higher temperatures followed by the self-assembly of these building blocks through weaker interactions into final nanostructures at lower temperatures. However, usually there are many other possible structures that are only slightly less stable. In this case, the stepwise approach can be used where the building blocks are separately formed in the first step are then mixed together in the presence of high magnesium (Mg++) concentration to form a final nanostructure. This approach is more time consuming and the melting temperatures of the building blocks and the final nanostructure should be well separated.

A number of RNA motifs are available as building blocks, including but not limited to RNA I and/or RNA II motifs, kissing loops, RNA I inverse (RNA Ii) and/or RNA II inverse (RNA IIi) motifs. As used herein, the term "motif" in reference to a nanoparticle is meant to refer to a double-stranded or single-stranded ribonucleic acid or analog thereof. Individual motifs are joined together into larger particles by attachment to each other. Attachment can occur by non-covalent linking. Numerous high-resolution RNA structures determined by NMR or X-ray crystallography can be separated into building blocks for design of new RNA nanoparticles and nanomaterials. U.S. application Ser. No. 13/378,985, incorporated by reference in its entirety herein, describes methods of making RNA nanoparticles.

The RNA NPs comprising one or more functionalities according to the invention can be in the shape of a ring, in the shape of a square or in the shape of a triangle; however it is to be understood that other geometries are possible. In certain embodiments, there is a positive relationship between the stability of RNA assemblies and the complexity of the tertiary structures that define the assembly.

R/DNA Hybrids

In certain embodiments, the present invention splits the functionality of Dicer substrates siRNA duplexes into two R/DNA hybrids, which upon simultaneous presence inside the same diseased cell will recognize each other through toehold interaction and re-associate releasing active siRNAs. This approach will overcome several challenges associated with the clinical delivery of RNAi, such as intravascular degradation (will be reduced for R/DNA hybrids), tissue specificity (DNA chemistry is more parsimonious than RNA and amenable to chemical modifications with different features for targeting or delivery), pharmacodynamics (fluorescent tags can be activated upon R/DNA hybrid re-association assisting in Förster resonance energy transfer (FRET) imaging of delivery and response). Moreover, all these additional functionalities can be introduced through chemical modifications of the DNA strands in the R/DNA hybrids thus, not interfering with the processivity of the released siRNAs. Additionally, the number of these functionalities can be at least as large as twice the number of DNA strands entering into the composition of the duplex hybrids or more complex hybrid nanostructures. R/DNA hybrids are described in PCT/US2012/065945, Filed Nov. 19, 2012, and incorporated by reference in its entirety herein.

Using RNA interference (RNAi) as a therapeutic agent it is routinely possible to knock down the expression of target genes in diseased cells. One of the ways to initiate the RNAi machinery is through the direct exogenous introduction to the cells of small interfering RNA (siRNA) duplexes. In certain embodiments, the invention provides for a strategy based on therapeutic RNA/DNA hybrids which can be generally used for triggering the RNAi pathway as well as other functionalities inside the diseased cells. Individually, each of the hybrids is functionally inactive and the therapeutic siRNA representation can only be activated by the re-association of at least two cognate hybrids simultaneously present in the same cell. The invention features a method for siRNA release where cognate hybrids are co-delivered to the cell either on the same or on two different days. The invention provides for nucleic acids based "smart" nanoparticles for biomedical applications.

In certain embodiments, the design rationale of R/DNA hybrids is the following: functional Dicer substrate siRNAs are split between two R/DNA hybrids preventing them from being diced and thus, making them non-functional. Additionally, it has been shown that substitution of one or both siRNA strands with DNA completely eradicates RNAi. Next, each of the hybrid DNA strands is decorated with a complementary toehold required for hybrid re-association resulting in Dicer substrate siRNA release.

Toehold Interaction

The rates of strand exchange reactions can be increased 106-fold by using toehold-mediated strand displacement (Yurke, et al. Nature 2000, 406, 605; Yurke et al. Genet. Program. Evol. Mach. 2003, 4, 111). Hybridization of the invading strand is initiated at a short single stranded "toehold" domain attached to one end of the substrate, leading to a branch migration reaction that displaces the target strand from the substrate. In the implementation demonstrated by Yurke and co-workers (Yurke et al. 2000; Yurke et al. 2003) and now widely adopted (Dittmer et al. Angew. Chem., Int. Ed. 2004, 43, 3550; Seelig, G. et al. Science 2006, 314, 1585; Qian et al Proceedings of the 14th International Meeting on DNA Computing; Goel et al. Eds.; Springer: Berlin, 2009; Vol. 5347, pp 70-89; Shlyahovsky et al. ACS Nano 2009, 3, 1831), the toehold and displacement domains are adjacent to each other with no intervening spacer: this simple architecture is referred to as "proximal". A proximal toehold functions both as an address tag and as a means to control the strand-displacement rate and equilibrium.

The term "toehold" refers to nucleation site of a domain comprising a nucleic acid sequence designed to initiate hybridization of the domain with a complementary nucleic acid sequence. The secondary structure of a nanoparticle may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part of. When exposed, a toehold is configured such that a complementary nucleic acid sequence can nucleate at the toehold.

A scheme of re-association for the hybrids is described in PCT/US2012/065945, Filed Nov. 19, 2012, and incorporated by reference in its entirety herein. The complementary single-stranded unzipped toeholds in R/DNA hybrids are designed using Mfold (Zuker, M, Nucleic Acids Res 31, 3406-3415 (2003)) to avoid any stable secondary structures. In order to exceed a melting temperature (Tm) of 37° C., the minimal length of the unzipped toeholds with GC content≥60% should be at least 12 nucleotides (nts). The Tm for designed single stranded toeholds is estimated to be ~40° C. using the Wallace rule (Wallace, R. B. et al., Nucleic Acids Res 6, 3543-3557 (1979)).

Conjugation to Nanoparticles

The polyvalent RNA nanoparticles comprising one of more functionalities can be used to deliver agents. For example, the polyvalent RNA nanoparticles comprising one or more functionalities can be used to deliver one or more agents that are selected from one or more of the group consisting of: siRNAs, RNA or DNA aptamers, fluorescent dyes, small molecules, RNA-DNA hybrids with split functionalities, split lipase, split GFP, proteins, therapeutic agents and imaging agents.

The compositions of the present invention have therapeutic uses. Any number of diseases or disorders can be treated by the compositions of the present invention and may be limited, in fact, only by the agent or agents that can be loaded in the inside of the nanoparticle or conjugated to the outside.

For example, RNA NPs can be engineered to carry multiple siRNAs against different disease targets. In one exemplary embodiment, six different siRNAs against different parts of the HIV-1 genome can be used for combinatorial RNAi therapy. The invention is not limited HIV, or to any disease or group of diseases, but is rather defined by the siRNAs that can be used to treat particular diseases. This concept of targeting a specific pathway upon the presence of a particular RNA in the cytoplasm can be applied to cancer (including cancer stem cells) or RNA viruses in general (e.g. Flaviviruses, Alphaviruses). HAART therapy as it currently exists, can successfully suppress virus replication within the human host. With this approach, however, it is currently not possible to eradicate the HIV virus from an infected patient because approved HIV drugs act as virus suppressors and do not kill human cells that are infected by the virus. The present invention can also lead to a novel anti-viral drug that has the unique feature of selectively killing HIV infected cells using appropriate aptamers, for cell targeting, that are associated with RNA NPs containing specific siRNAs or RNA/DNA siRNA hybrids. The guide strands are designed to be an antisense to human apoptosis inhibitor genes (BCL-2, FLIP, STATS, XIAP, SURVIVIN, etc). Thus, the activation of RNAi (RNA interference pathway) will result in apoptosis of the HIV-infected cell. In addition, in a more general sense, the siRNA targets may include cancer related genes, for example, but not limited to, the hypoxia pathway: Hif1alpha, VEGF; DNA repair pathway: PARP; microRNAS: miR21, miR7, mIR128a, mIR210; cancer stem cells: genes in NOTCH, HEDGEHOG, PTEN, WNT, TGFbeta pathways; immune modulation: Interleukin (IL-6, IL-10) and genes in the JAK/STAT, SMAD, TNFalpha. In principle the concept can be expanded to include any genetically related diseases.

Exemplary potential applications of multi-functional nanoparticles of the invention in which 2, 3, 4, or more agents are coupled to a nanoparticle include using one or more agents to target a macromolecular structure or a cell and using the second one to alter the function/properties of the macromolecule or cell, e.g., using a protein to target a cell and using a toxin or cell death protein to kill the targeted cell, using an siRNA to silence genes, or using a fluorescent particle for visualization, or using a chemical or protein to target a protein within a complex and another one to alter the function of a different component of the complex.

In certain embodiments, the nanoparticle comprises one or more agents. In further preferred embodiments, the agent can be conjugated to the nanoparticle. Conjugated can be understood as attached, linked, mixed, or otherwise present on or in a magnetoliposome. For example, an agent can be conjugated by covalent or ionic linkage, by use of a chelate or other linker moiety. As used herein, conjugation of an agent to a nanoparticle does not disrupt the desired activity of the agent.

The agent can comprise any material or compound or composition or agent for in vivo or in vitro use for imaging, diagnostic or therapeutic treatment that can be enclosed in the inside the nanoparticle or can be conjugated with the nanoparticle without appreciably disturbing the physical integrity of the nanoparticle. A nanoparticle can comprise one or more agents of one or more types. For example, a nanoparticle can comprise a therapeutic agent, and the targeting of the agent can be followed by further conjugation with an imaging agent. Similarly, cocktails of therapeutic agents are typically used in the treatment of cancer. A nanoparticle can comprise more than one type of therapeutic agent.

Examples of agents include inhibitory nucleic acids, including but not limited to siRNAs, RNA or DNA aptamers, fluorescent dyes, small molecules, RNA-DNA hybrids with split functionalities, split lipase, split GFP, proteins, therapeutic agents and imaging agents (for example gadolinium, manganese, chromium, or iron).

In certain embodiments, the NP molecules described herein operate by forming inhibitory nucleic acid molecules once in target cells. Such inhibitory nucleic acids include single and double stranded nucleic acid molecules (e.g., DNA, RNA, and analogs thereof) that bind a nucleic acid molecule that encodes target RNA (e.g., antisense oligonucleotide molecules, siRNA, shRNA) as well as nucleic acid molecules that bind directly to a target polypeptide to modulate its biological activity (e.g., aptamers).

Catalytic RNA molecules or ribozymes that include an antisense target RNA sequence of the present disclosure can be used to inhibit expression of target RNAs in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

The disclosure also features a catalytic RNA molecule that includes, in the binding arm, an antisense RNA having between eight and nineteen consecutive nucleobases. In preferred embodiments of this disclosure, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the disclosure and those skilled in the art will recognize that all that is important in an enzymatic nucleic acid molecule of this disclosure is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

By "siRNA" is meant a double stranded RNA. Optimally, an siRNA is 18, 19, 20, 21, 22, 23, 24 or more nucleotides in length and has a 2 base overhang at its 3' end. It is understood that the term "siRNA" includes both diceable and non-diceable siRNAs. These dsRNAs can be introduced to an individual cell or to a whole animal; for example, they may be introduced systemically via the bloodstream. Such siRNAs are used to downregulate mRNA levels or promoter activity. Functional siRNAs can be released by Dicer nuclease. Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39, 2002).

Given the sequence of a target gene, siRNAs may be designed to inactivate that gene. Such siRNAs, for example, could be administered directly to an affected tissue, or administered systemically. The nucleic acid sequence of an Parl gene can be used to design small interfering RNAs (siRNAs). The 21 to 25 nucleotide siRNAs may be used, for example, as therapeutics to inhibit disease related genes.

The inhibitory nucleic acid molecules of the present disclosure may be employed as double-stranded RNAs for RNA interference (RNAi)-mediated knock-down of target RNA expression. In therapeutic embodiments, the target RNA is a disease related gene. For example, in a non-limiting embodiment, the target RNA is a gene that is involved in HIV. IN another embodiment, the target RNA gene is a gene that is involved in cancer development or progression. In another embodiment, target RNA expression is reduced in a virus infected cell. In another embodiment, the target RNA encodes apoptosis inhibitor proteins and the cells are infected with HIV. RNAi is a method for decreasing the cellular expression of specific proteins of interest (reviewed in Tuschl, ChemBioChem 2:239-245, 2001; Sharp, Gene Dev 15:485-490, 2000; Hutvagner and Zamore, Curr Opin Genet Devel 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the disclosure, a double-stranded RNA (dsRNA) molecule is made that includes between eight and nineteen consecutive nucleobases of a nucleobase oligomer of the disclosure. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Gene Dev 16:948-958, 2002. Paul et al. Nat Biotechnol 20:505-508, 2002; Sui et al. Proc Natl Acad Sci USA 99:5515-5520, 2002; Yu et al. Proc Natl Acad Sci USA 99:6047-6052, 2002; Miyagishi et al. Nat Biotechnol 20:497-500, 2002; and Lee et al. Nat Biotechnol 20:500-505, 2002, each of which is hereby incorporated by reference. In certain embodiments, the sense strand of the double stranded siRNA is split into two smaller oligonucleotides, also referred to as three stranded siRNA.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above. The invention encompasses stabilized R/DNA NPs having modifications that protect against 3' and 5' exonucleases as well as endonucleases. Such modifications desirably maintain target affinity while increasing stability in vivo. In various embodiments, R/DNA NPs of the invention include chemical substitutions at the ribose and/or phosphate and/or base positions of a given nucleobase sequence. For example, R/DNA NPs of the invention include chemical modifications at the 2' position of the ribose moiety, circularization of the aptamer, 3' capping and 'spiegelmer' technology. R/DNA NPs having A and G nucleotides sequentially replaced with their 2'-OCH3 modified counterparts are particularly useful in the methods of the invention. Such modifications are typically well tolerated in terms of retaining affinity and specificity. In various embodiments, R/DNA NPs include at least 10%, 25%, 50%, or 75% modified nucleotides. In other embodiments, as many as 80-90% of the R/DNA NPs' nucleotides contain stabilizing substitutions. In other embodiments, 2'-OMe containing R/DNA NPs are synthesized. Such R/DNA NPs are desirable because they are inexpensive to synthesize and natural polymerases do not accept 2'-OMe nucleotide triphosphates as substrates so that 2'-OMe nucleotides cannot be recycled into host DNA. Using methods described herein, R/DNA NPs will be selected for increased in vivo stability. In one embodiment, R/DNA NPs having 2'-F and 2'-OCH3 modifications are used to generate nuclease resistant aptamers. In other embodiments, the nucleic acids of the invention have one or more locked nucleic acids (LNA). LNA refers to a modified RNA nucleotide. The ribose of the LNA is modified with an extra bridge connecting the 2' oxygen and the 4' carbon which locks the ribose into the North or 3'-endo conformation. See e.g., Kaur, H. et al., Biochemistry, vol. 45, pages 7347-55; and Koshkin, A. A., et al., Tetrahedron, vol. 54, pages 3607-3630. In other embodiments, one or more nucleic acids of the invention incorporate a morpholino structure where the nucleic acid bases are bound to morpholine rings instead of deoxyribose rings and are linked through phosphorodiamidate groups instead of phosphates. See eg., Summerton, J. and Weller, D., Antisense & Nucleic Acid Drug Development, vol. 7, pages 187-195. Yet other modifications, include (PS)-phosphate sulfur modifications wherein the phosphate backbone of the nucleic acid is modified by the substitution of one or more sulfur groups for oxygen groups in the phosphate backbone. Other modifications that stabilize nucleic acids are known in the art and are described, for example, in U.S. Pat. No. 5,580,737; and in U.S. Patent Application Publication Nos. 20050037394, 20040253679, 20040197804, and 20040180360.

The agent may be a RNA or DNA aptamer. An aptamer is a stable DNA, RNA, or peptide that binds with high affinity and specificity to targets such as small organics, peptides, proteins, cells, and tissues. Unlike antibodies, some aptamers exhibit stereoselectivity. The present invention is not limited to any particular aptamer, but rather can be any aptamer known in the art to be useful in treating a disease or condition. For example, the Aptamer Database is a comprehensive, annotated repository for information about aptamers and in vitro selection. This resource is provided to collect, organize and distribute all the known information regarding aptamer selection, and is publicly available at http://aptamer.icmb.utexas.edu/.

The agent may be RNA-DNA hybrids with split functionalities, as described infra.

The agent may also be a targeting agent that directs the nanoparticle to a delivery site. For example, the targeting agent may be a ligand, e.g. a peptide ligand that has specific cell surface binding partners, e.g., ligand receptors, that are preferentially exhibited on the surface of a target cell. As used herein, "receptor" and "ligand" refer to two members of a specific binding pair that are binding partners. A receptor is that member of the pair that is found localized on the surface of the target; the ligand is the member of the pair that is found on the surface of the nanoparticle. Accordingly, the in certain embodiments, the invention features a nanoparticle comprising a member of a binding pair, or a fragment thereof that retains the capacity to specifically bind the other member of the binding pair, on its surface and the other member of that binding pair, or a fragment thereof that retains the capacity to specifically bind its partner, is present on the surface of a target. In certain embodiments, the targeting agent may be an antibody, for example a single-chain antibody, for which a binding partner would include an antigen thereof, or a fragment, derivative or variant thereof that retains the capacity to bind to the single-chain antibody.

A therapeutic agent may be a molecule, atom, ion, receptor and/or other entity which is capable of detecting, identifying, inhibiting, treating, catalyzing, controlling, killing, enhancing or modifying a target such as a protein, glycoprotein, lipoprotein, lipid, a targeted cell, a targeted organ, or a targeted tissue.

In certain cases, the therapeutic agent is a radiotherapeutic agent, and can be selected from, but is not limited to radioactive gadolinium, radioactive boron, and radioactive iodine.

In certain examples, the agent can be, but is not limited to: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, carboplatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, temozolamide, trimethoprim, cisplatin, oxaliplatin, mechlorethamine, cyclophosphamide, chlorambucil, azathioprine, mercaptopurine, vinca alkaloids, taxanes, vincristine, vinblastine vinorelbine, vindesine, etoposide, teniposide, paclitaxel, irinotecan, topotecan, amsacrine, etoposide, etoposide phosphate, teniposide, and dactinomycin and valban; diphtheria toxin, gelonin, exotoxin A, abrin, modeccin, ricin, radioactive gadolinium, radioactive boron, and radioactive iodine; or toxic fragments thereof; metal ions, such as the alkali and alkaline-earth metals; radionuclides, such as those generated from actinides or lanthanides or other similar transition elements or from other elements, such as 51Cr, 47 Sc, 67 Cu, 67 Ga, 82 Rb, 89 Sr, 88 Y, 90 Y, 99m Tc, 105 Rh, 109 Pd, 111 In, 115m In, 125 I, 131 I, 140 Ba, 140 La, 149 Pm, 153 Sm, 159 Gd, 166 Ho, 175 Yb, 177 Lu, 186 Re, 188 Re, 194 Ir, and 199 Au; signal generators, which includes anything that results in a detectable and measurable perturbation of the system due to its presence, such as fluorescing entities, phosphorescence entities and radiation; signal reflectors, such as paramagnetic entities, for example, Fe, Gd, Cr, or Mn; chelated metal, such as any of the metals given above, whether or not they are radioactive, when associated with a chelant; signal absorbers, such as contrast agents and electron beam opacifiers, for example, Fe, Gd, Cr, or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Other pharmaceutical materials include scavenging agents such as chelants, antigens, antibodies or any moieties capable of selectively scavenging therapeutic or diagnostic agents.

Other examples of therapeutic agents include antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Nanoparticles may be directed to target sites. Preferred target sites comprise cancer cells, solid tumors, sites of inflammation and damaged bone or tissue.

For example, nanoparticle may further comprise an antibody or a peptide that acts as a targeting moiety to enable specific binding to a target cell bearing a target molecule, e.g., a cell surface marker to which the antibody or peptide is directed or a disease-specific marker to which the antibody or peptide is directed. The nanoparticle may further comprise a nucleotide, e.g. an oligonucleotide, that acts as a targeting moiety to enable specific binding to a target cell bearing a target molecule. For example, the oligonucleotide may be an aptamer that binds a specific target molecule.

Further exemplary potential applications of the multifunctional nanoparticles of the invention include use of the nanoparticles as riboswitch aptamers, ribozymes, or beacons.

Riboswitches are a type of control element that use untranslated sequence in an mRNA to form a binding pocket for a metabolite that regulates expression of that gene. Riboswitches are dual function molecules that undergo conformational changes and that communicate metabolite binding typically as either increased transcription termination or reduced translation efficiency via an expression platform.

Ribozymes catalyze fundamental biological processes, such as RNA cleavage by transesterification. The polyvalent RNA nanoparticles of the invention can be incorporated in to ribozymes using methods described in, for example, U.S. Pat. No. 6,916,653, incorporated by reference in its entirety herein.

A number of "molecular beacons" (often fluorescence compounds) can be attached to RNA nanoparticles of the invention to provide a means for signaling the presence of, and quantifying, a target analyte. Molecular beacons, for example, employ fluorescence resonance energy transfer-based methods to provide fluorescence signals in the presence of a particular analyte/biomarker of interest. In preferred embodiments, the term "molecular beacon" refers to a molecule or group of molecules (i.e., a nucleic acid molecule hybridized to an energy transfer complex or chromophore(s)) that can become detectable and can be attached to a nanoparticle under preselected conditions. Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission. Molecular beacons and AFPs, including their methods for preparation, that can be used in the present invention are described in numerous patents and publications, including U.S. Pat. No. 6,261,783.

Any protein can be coupled to nanoparticles. For instance, glycoproteins are most easily coupled, as they can be oxidized to generate an active aldehyde group. Other proteins can be coupled via their —COOH group(s) but with lower efficiency. However, other means known in the art, such as di-imide reagents, e.g. carbodiimide can be used to couple proteins lacking sugars to the nanoparticles.

Polyethylene Glycol (PEG) chains can be conjugated to the nanoparticles. PEG chains render the nanotubes highly water-soluble. PEG-phospholipids (PEG-PL) have been used in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464).

Functional groups can be coupled to the nanoparticle, for instance the functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality or a complementary group. In addition, RNA functional groups can be attached, as for example ribozymes or riboswitch aptamers.

The nanoparticle can be used for attachment of small molecules for specific interactions with nucleic acids, carbohydrates, lipids, proteins, antibodies, or other ligands.

The nanoparticle can have dyes attached. The dye is can be a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, OliGreen, and combinations thereof. Other dyes include, thiazole orange, oxazole yellow, or non-intercalating dyes such as fluorescein, rhodamine, cyanine or coumarin based dyes, and combinations thereof. Other suitable dyes include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcoulaurin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalocyanine. Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes. According to the invention, one or more therapeutic, diagnostic, or delivery agents are directly included in the building block sequences. In certain embodiments, the delivery agent can be a targeting agent. Targeting agents are used to direct the nanoparticle to a tissue or cell target. An exemplary embodiment of a targeting agent is an antibody. For example, antibodies suitable for use as targeting agents in the present invention include antibodies directed to cell surface antigens which cause the antibody-nanoparticle complex to be internalized, either directly or indirectly. For example, in the treatment of cancer, suitable antibodies include antibodies to CD33 and CD22. CD33 and CD22 that are over-expressed and dimerized on lymphomas.

In certain preferred embodiments of the invention biotin is conjugated to the nanoparticle. For example, the nanoparticles of the invention can be further functionalized using biotin-streptavidin interactions to immobilize molecules inside or outside the polyhedra, e.g. polyhedral cages. For example, streptavidin can be conjugated to guanosine monophosphothioate (GMPS)-modified tectoRNAs by means of a biotin linker. In certain preferred embodiments, the biotin linker is incorporated to a mono-phosphothioate at the 5' position of tectoRNAs.

A wide variety of particle sizes are suitable for the present invention. In certain aspects, the particle has a diameter of about 10 nanometers to about 10 microns. Preferably the particle diameter is about 10 to 700 nanometers, and more preferably, the diameter of about 10 nanometers to about 100 nanometers.

The polyvalent RNA nanoparticle or the polyvalent RNA nanotube as described herein has a number of uses. For example, the polyvalent RNA nanoparticle or the polyvalent RNA nanotube can be used in drug delivery, imaging, nanocircuits, cell growth surfaces, medical implants, medical testing, or gene therapy.

In one particular embodiment, the polyvalent RNA nanoparticle or the polyvalent RNA polyhedra, e.g. cages, as described can be used in biological meshes. In one exemplary embodiment, the invention as described herein may find use as a biosensor in, for example, pathogen detection. In one particular embodiment, self-assembling nano-meshes are used to attach biosensors for pathogen detection or for x-ray crystallography by placing multiple copies of a protein or functional RNAs, for example, on the mesh. Biosensors for pathogen detection are advantageously employed in bioterrorism capacities.

In another exemplary embodiment, the polyvalent nanoparticles of the invention, as described herein, are employed as skeletons or scaffolds for tissue growth.

These uses are exemplary, and not considered to be limiting.

Compositions

The invention, in part, pertains to a drug delivery composition comprising the NP as described herein. The drug delivery composition of the invention can gain entry into a cell or tissue.

Advantageously, the drug delivery composition of the invention provides for a more controlled delivery of an active agent, especially a therapeutic agent, to a site of action at an optimum rate and therapeutic dose. Thus, improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

It is understood by one of skill in the art that changing the base composition of RNA changes the half-life of RNA and thus the release of RNA from the composition. For instance, the composition can be modified to consist of fast release, slow release or a staged release of polyvalent RNA nanoparticle.

In certain preferred embodiments, the drug delivery composition can comprise a second therapeutic agent. In some embodiments, the composition comprising nanoparticles and the second therapeutic agent are administered simultaneously, either in the same composition or in separate compositions. In some embodiments, the nanoparticle composition and the second therapeutic agent are administered sequentially, i.e., the nanoparticle composition is administered either prior to or after the administration of the second therapeutic agent. The term "sequential administration" as used herein means that the drug in the nanoparticle composition and the second agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages. In some embodiments, the administration of the nanoparticle composition and the second therapeutic agent are concurrent, i.e., the administration period of the nanoparticle composition and that of the second therapeutic agent overlap with each other. In some embodiments, the administration of the nanoparticle composition and the second therapeutic agent are non-concurrent. For example, in some embodiments, the administration of the nanoparticle composition is terminated before the second therapeutic agent is administered. In some embodiments, the administration of the second therapeutic agent is terminated before the nanoparticle composition is administered. Administration may also be controlled by designing the RNA nanoparticle or nano-tube to have different half lives. Thus, particle dissolution would be controlled by a timed release based upon variations in designed RNA stability.

The second therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent is selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine;

romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The invention also relates to pharmaceutical or diagnostic compositions comprising the nanoparticles of the invention and a pharmaceutically acceptable carrier. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

Methods of Treatment

The methods of the invention encompass method of treating or preventing diseases or disorders by administering to subjects in need thereof an effective amount of a polyvalent RNA nanoparticle comprising one or more functionalities as described herein. Accordingly, a number of diseases or disorders are suitable for treatment according to the methods of the invention. Examples include, but are not limited to, Adenoma, Ageing, AIDS/HIV, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, Sepsis, Sickle-cell disease, Teratoma, Ulcerative colitis, and Uveitis.

The methods of the invention further encompass diagnostics.

The methods may be practiced in an adjuvant setting. "Adjuvant setting" refers to a clinical setting in which, for example, an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. Thus, in some embodiments, the individual has previously been treated. In other embodiments, the individual has not previously been treated. In some embodiments, the treatment is a first line therapy.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Methods of Delivery

The nanoparticle compositions described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the therapy and the particular disease being treated. For example, dosing frequency may include, but is not limited to, once daily, twice daily, weekly without break; weekly, three out of four weeks; once every three weeks; once every two weeks; weekly, two out of three weeks.

The administration of nanoparticles may be carried out at a single dose or at a dose repeated once or several times after a certain time interval. The appropriate dosage varies according to various parameters, for example the individual treated or the mode of administration.

The dosing frequency of the nanoparticle composition or the nanoparticle composition and the second therapeutic agent may be adjusted over the course of the treatment, based on the judgment of the administering physician.

When administered separately, the nanoparticle composition and the second therapeutic agent can be administered at different dosing frequency or intervals. For example, the nanoparticle composition can be administered weekly, while a second agent can be administered more or less frequently. In some embodiments, sustained continuous release formulation of the nanoparticle and/or second agent may be used. Various formulations and devices for achieving sustained release are known in the art. The doses required for the nanoparticle composition and/or the second agent may (but not necessarily) be lower than what is normally required when each agent is administered alone. Thus, in some embodiments, a subtherapeutic amount of the drug in the nanoparticle composition and/or the second agent are administered. "Subtherapeutic amount" or "subtherapeutic level" refer to an amount that is less than the therapeutic amount, that is, less than the amount normally used when the drug in the nanoparticle composition and/or the second agent are administered alone. The reduction may be reflected in terms of the amount administered at a given administration and/or the amount administered over a given period of time (reduced frequency).

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the disease to be treated may receive treatments to inhibit and/or delay the development of the disease. The dose of nanoparticle composition will vary with the nature of the therapy and the particular disease being treated. The dose should be sufficient to effect a desirable response, such as a therapeutic or prophylactic response against a particular disease.

Appropriate doses will be established by persons skilled in the art of pharmaceutical dosing such as physicians.

In certain embodiments, the siRNAs can be administered as bolaamphiphiles. Bolaamphiphiles have relatively low toxicities, long persistence in the blood stream, and most importantly, in aqueous conditions can form poly-cationic micelles thus, becoming amenable to association with siRNAs. Depending on the application, the extent of siRNA chemical protection, delivery efficiency, and further intracellular release can be varied by simply changing the type of bolaamphiphile used (see, e.g. Kim et al. Mol Ther Nucleic Acids. 2: e80, 2013, incorporated by reference in its entirety herein).

Kits

The disclosure provides kits for the treatment or prevention of disease. In one embodiment, the kit includes a therapeutic or prophylactic composition containing an effective amount of an agent of the invention (e.g., NPs) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., neoplasia or viral infection). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Recombinant Polypeptide Expression

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The promise of RNA interference based therapeutics is made evident by the recent surge of biotechnological drug companies that pursue such therapies and their progression into human clinical trials. Recent achievements in RNA nanotechnology introduced nanoscaffolds (nanorings) with the potential for a broad use in biomedical applications (PCT/US10/38818, incorporated by reference in its entirety herein). As presented herein, besides functionalization with multiple short interfering RNAs for combinatorial RNA interference, these nanoscaffolds also allow simultaneous embedment of assorted RNA aptamers, fluorescent dyes, proteins, as well as recently developed auto-recognizing RNA-DNA hybrids used to conditionally activate multiple split functionalities. These new constructs were extensively characterized and visualized in vitro, in cell culture and in vivo by various experimental techniques. The results revealed a higher detection sensitivity of diseased cells and significant increases in silencing efficiencies of targeted genes compared to the silencing caused by equal amounts of conventional siRNAs. Due to the combinatorial nature and relative engineering simplicity, these RNA nanoparticles are expected to be useful for various nanotechnological applications.

Example 1. Functional Nanorings Assembly and Characterization

Figure 1A:
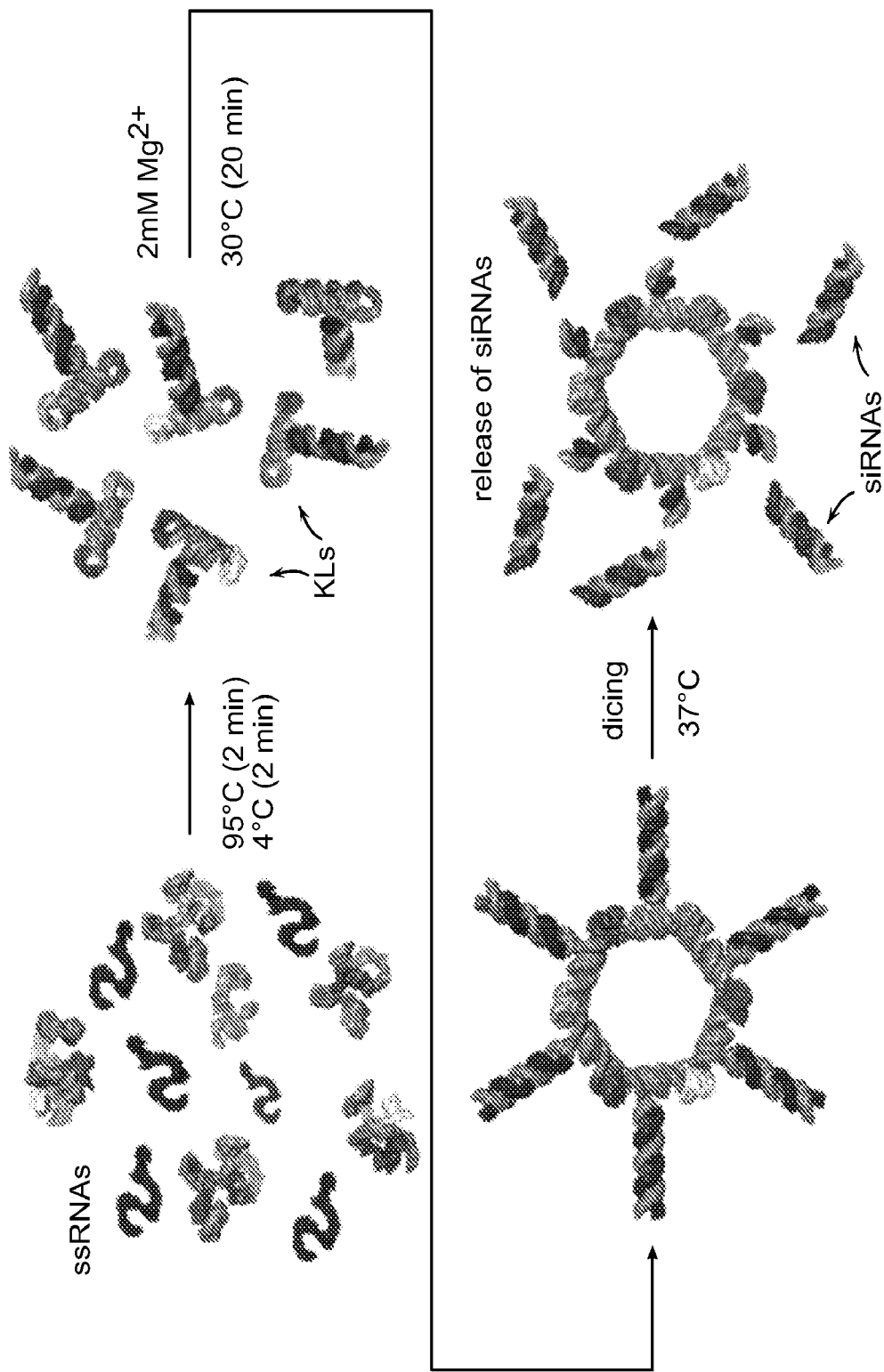
FIGS. 1a-h show assemblies of RNA nanorings functionalized with six different siRNAs and/or other functionalities. (a) Schematic representation of assemblies leading to the formation of RNA nanorings functionalized with six siRNAs. Functional siRNAs can be released by Dicer nuclease. (b) Native-PAGE results representing assemblies leading to the formations of RNA nanorings functionalized with different numbers of DS RNAs (0-6). Dynamic light scattering (DLS) also shows assembly result and denotes nanorings radius. (c) In vitro dicing experiments. RNA nanorings functionalized with six siRNAs were incubated with human recombinant Dicer enzyme (Methods). The dicing results were analyzed using native-PAGE (left) and denaturing 8M urea PAGE (right) and show successful siRNA cleavage. Non-functionalized RNA nanoring was used as a control. (d) Assemblies of RNA nanorings functionalized with different numbers (0-6) of Malachite Green (MG) aptamers demonstrate the sequential increase in the fluorescence of MG dye. (e) Schematic representation of MG aptamers for in vitro visualization. (f) J18 aptamers for cell targeting and phycoerythrin for visualization in vivo. (g) Dicer substrate RNAs introduced via the toehold interactions, and (h) RNA-DNA hybrids with split functionalities (RNAi and FRET). Functional siRNAs can be released by Dicer nuclease.
Figure 1C:
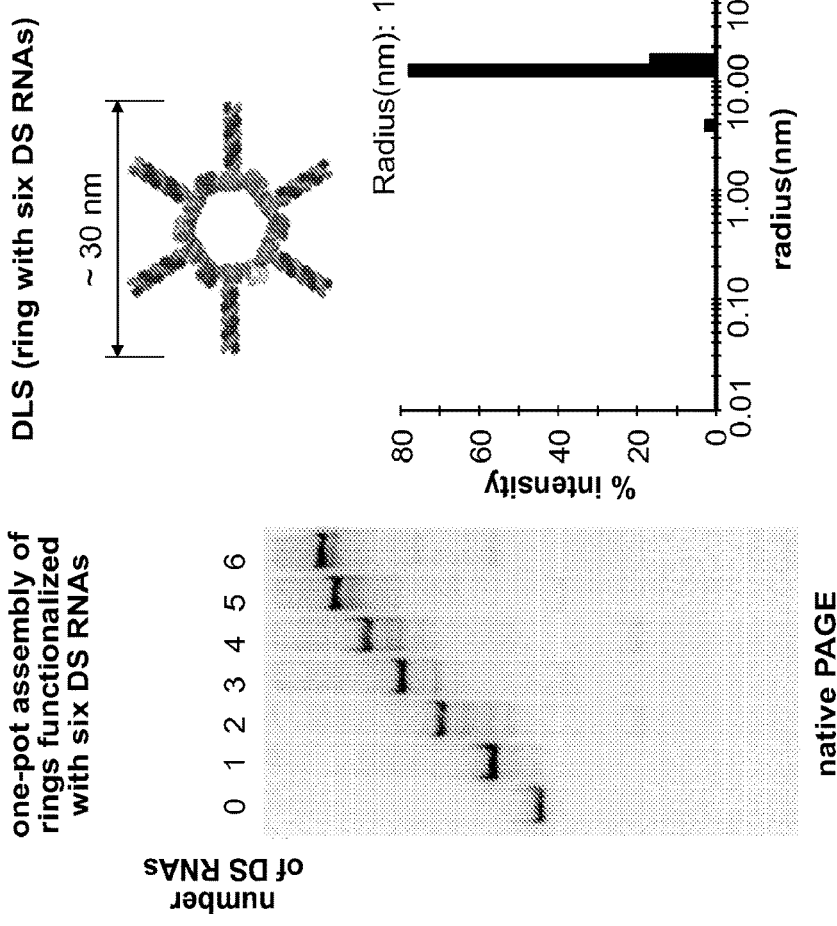
Figure 1B:
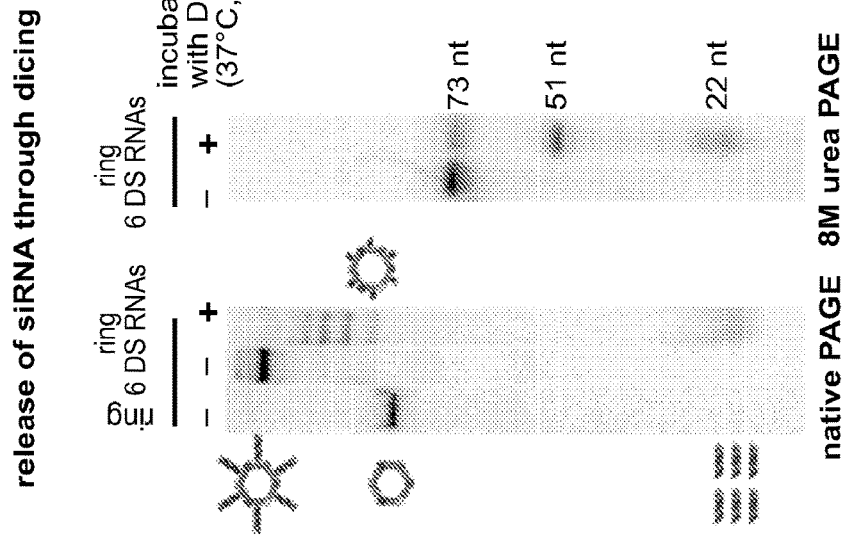
Figure 1D:
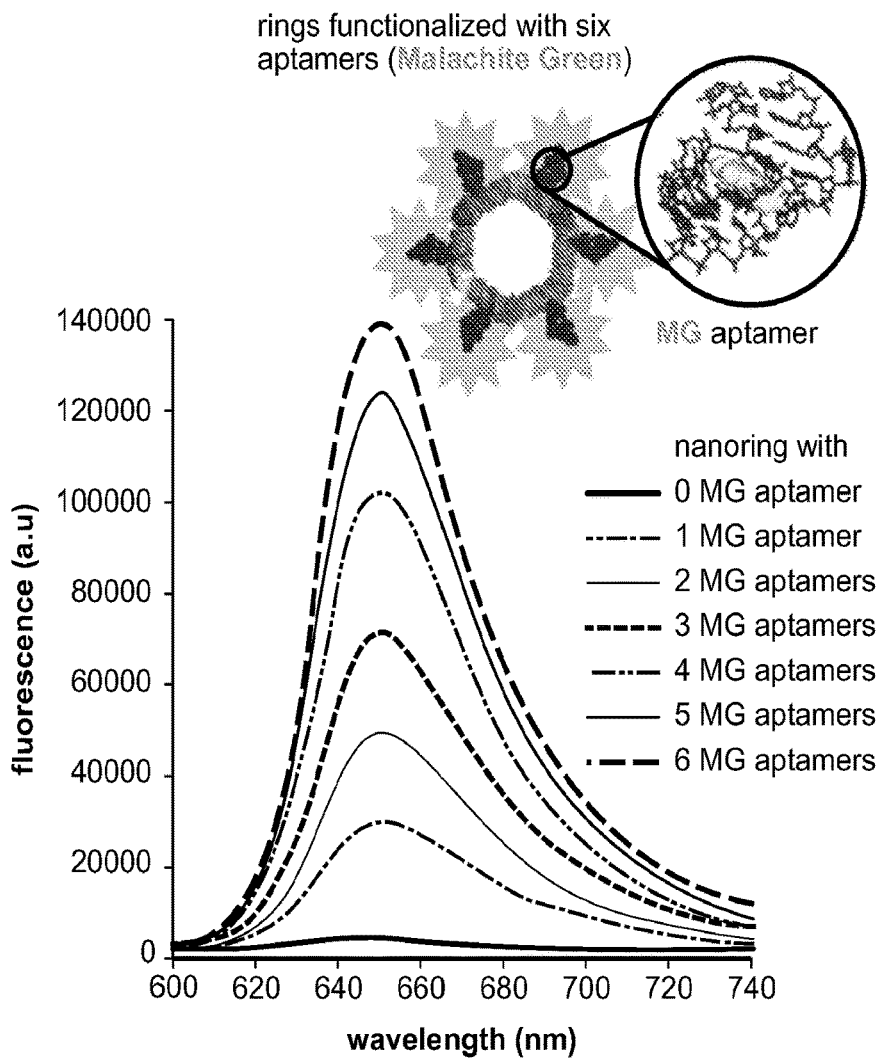
Figure 1E:
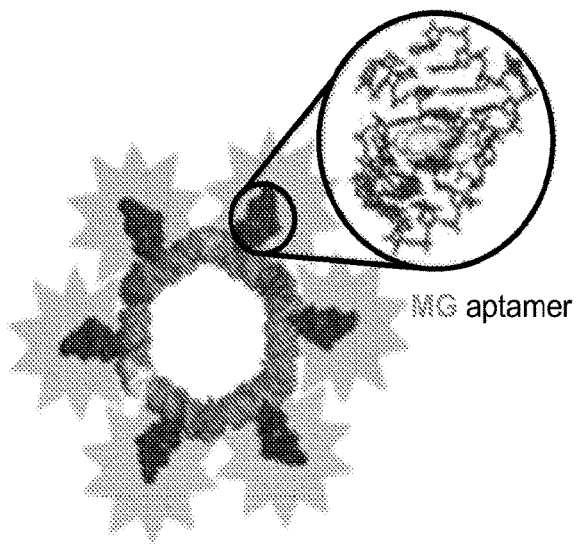
Figure 1F:
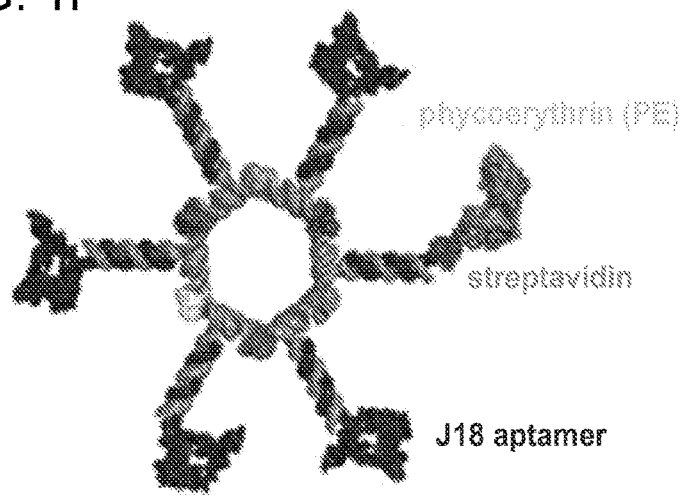
Figure 1G:
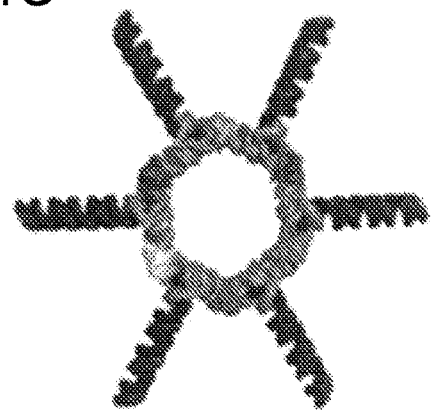
Figure 1H:
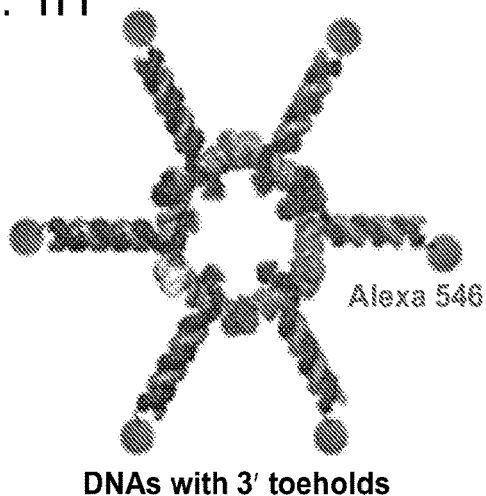

The assembly process depicted in FIG. 1a requires several incubation steps and certain buffer conditions detailed elsewhere[4, 5]. In vitro assembled nanorings functionalized with different numbers of elongated DS RNAs[6] were characterized structurally by native PAGE and dynamic light scattering (FIG. 1b). Release of functional moieties (siRNAs) through the process of dicing was confirmed by in vitro assays with human recombinant Dicer (FIG. 1c). The scaffold and siRNA products were identified by comparison to the appropriate controls using native and denaturing PAGE and results were consistent with previous studies[5].

To demonstrate the combinatorial nature of the scaffolds, nanorings were functionalized with up to six RNA aptamers (FIG. 1d and FIG. 9c) selected to bind the malachite green (MG) dye and significantly increase its emission which is otherwise undetectable in aqueous solutions[7-9]. This aptamer was previously used for the laser-mediated inactivation of RNA transcripts[8], bio-sensing of native RNAs[7], DNAs[9], and small molecules[10], real-time visualization of co-transcriptional assemblies[11], RNA-DNA hybrid re-association[12], as well as formation of RNA nanoparticles[13]. Current fluorescence studies indicate that the sequential increase in fluorescence of MG is directly proportional to the number of aptamers introduced to nanoring scaffolds. Moreover, the functional scaffolds can be produced co-transcriptionally and the assembly of nanorings carrying six aptamers can be tracked in real time through the fluorescent and native-PAGE experiments (FIG. 9d).

Figure 2A:
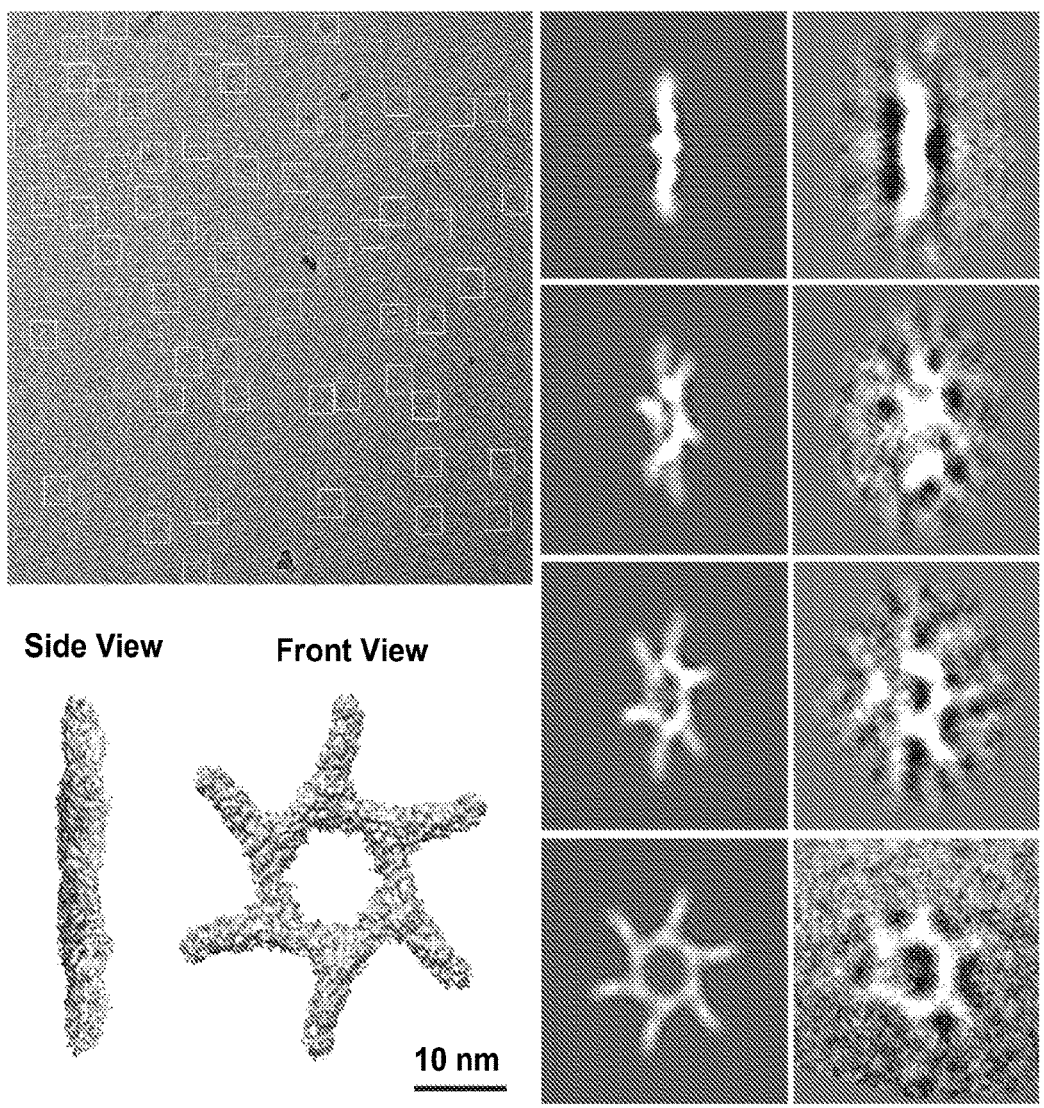
FIGS. 2a and b show structural characterization of siRNA nanorings by cryo-EM. (a) Top left panel: A typical cryo-EM image of the siRNA nanoring particles. Right panel: Class averages for each siRNA nanoring as observed by cryo-EM, with corresponding projections of the reconstructed three-dimensional structure. Bottom left panel: Single particle reconstruction of the siRNA nanoring. Side and front views of the model are shown. (b) Additional single particle reconstruction of functionalized RNA nanorings. Different views of the model fit with the electron density volume are shown. The volume map was thresholded at the minimum level at which all the atoms of the model could be fit inside the volume. The resolution is 16 Å.
Figure 2B:
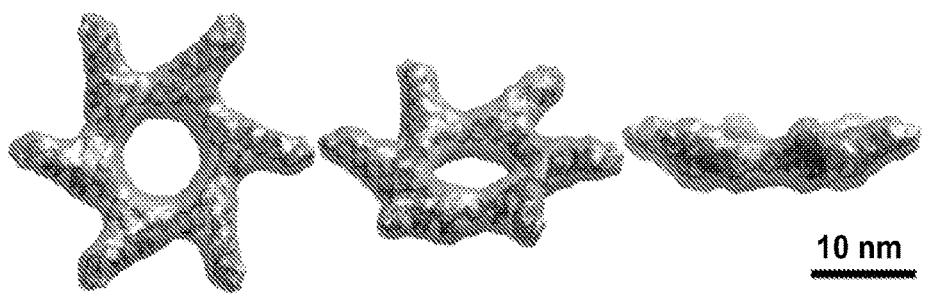

The formation of DS RNA containing nanorings was also visualized using cryogenic electron microscopy (cryo-EM) imaging and further single-particle reconstruction. The cryo-EM images show that RNA particles have the expected size and uniform distribution throughout the imaging field (FIG. 2). Three-dimensional structures of DS RNA containing nanorings were obtained using EMAN2 reconstruction. The cryo-EM images showed that the RNA particles have the expected size and uniform distribution throughout the imaging field (FIG. 2a). The computed projections from these three-dimensional reconstructions matched well with the class averages of observed particles with similar views (FIG. 2a). Reconstructed models of the nanoring have structural features in good agreement with the predicted three-dimensional nanoring model displayed in FIG. 2b. Specifically, the final 16 A Cryo-EM map with imposed six-fold symmetry showed that the arms in the siRNA ring do not point straight out. (FIGS. 2b and 17). Looking from the side, siRNA arms point about 25 degrees upward thus creating a crown shape in the hexagonal molecule. Also, looking from the top, the DS RNA arms are positioned in a pinwheel fashion around the ring. The six DS RNA arms point about 53 degrees clockwise compared to the arms in the FIG. 1 model. Computational modeling of the DS RNA ring generated a cluster of crown-shaped models, as well as alternatives varying the up or down orientation of the DS arms, and most suggested the top-view pinwheel positioning. The model yielding the best fit into the cryo-EM density map is illustrated in FIG. 2b.

Atomic force microscopy (AFM) characterization can also be used to assess the formation of the nanorings (see, e.g. Grabow et al., Nano Lett. 2011 Feb. 9; 11(2): 878-887).

Example 2. Transfection, Gene Silencing and Targeting Experiments In Vitro

Figure 3A:
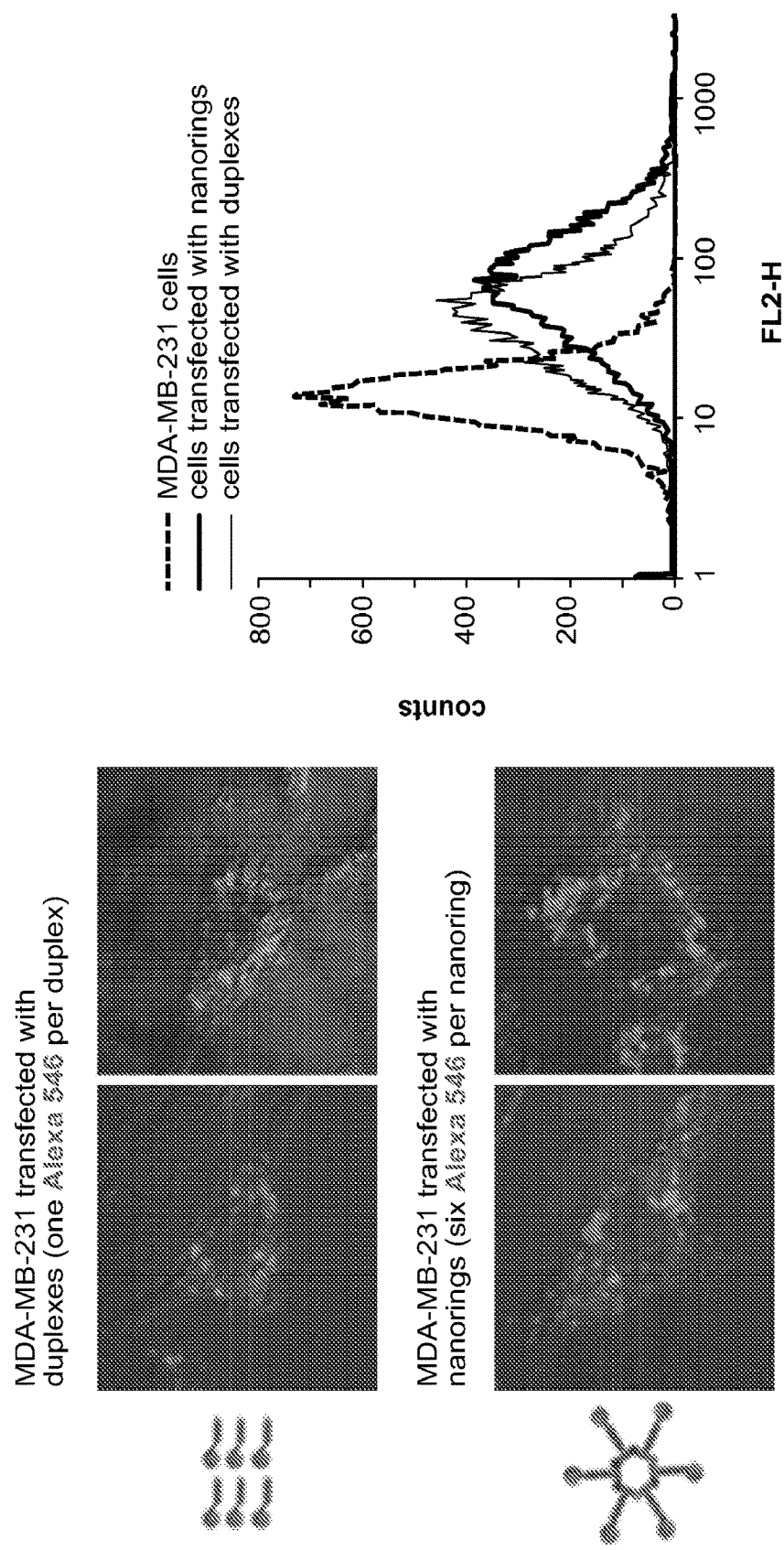
FIG. 3 shows relative transfection/cell uptake, endosomal co-localization, silencing and RNA aptamer-mediated binding efficiencies of functional nanorings. (a) Transfection efficiencies of human breast cancer cells (MDA-MB-231). DS RNAs (60 nM final) covalently labeled with one Alexa 546 per duplex were compared to the functionalized nanorings (10 nM final) labeled with six Alexa 546 dyes. One day after the transfection, the efficiencies were analyzed by confocal fluorescence microscopy and flow cytometry experiments. (b) Studying the localization of nanorings with commonly used markers for endosomal compartments Early Endosome Antigen 1 (EEA1) and Rab7. (c) GFP knockdown assays in human breast cancer cells (MDA-MB-231/GFP) which stably express enhanced GFP (eGFP). Fluorescence microscopy (left panel) and statistical analysis (30000 cells per sample) of flow cytometry experiments (right panel) of eGFP expression three days after the transfection of cells with siRNA duplexes and nanorings functionalized with six DS RNAs against eGFP. The ratio of siRNA duplexes to DS RNA nanorings was six to one. (d) Nanorings labeled with phycoerythrin (PE) and containing different number of J18 aptamers selected to specifically bind EGFR expressed on A431 cells were tested for relative binding efficiencies in flow cytometry experiments. Image numbers in (b) correspond to: differential interference contrast (DIC) images (1), Alexa546 emission (2), EEA1 antibody staining (3), and Rab7 antibody staining (4). Images (1+2+3) and (1+2+4) are superpositions of three different images.

To study the potential use of nanorings as scaffolds for simultaneous delivery of multiple siRNAs, nanorings functionalized with six fluorescently tagged DS RNAs were transfected into human breast cancer cells (FIG. 3a, FIG. 10). The next day, transfection efficiencies were visualized by confocal fluorescence microscopy and statistically analyzed by fluorescence-activated cell sorting (FACS). The results presented in FIG. 3a revealed a significantly higher intracellular uptake through endocytosis (endocytic uptake was confirmed by the co-localization experiments shown in FIG. 3b) for functionalized nanorings compared to the uptake of fluorescently labeled individual siRNAs transfected at six times higher concentration. This can be attributed to the tighter binding of the RNA NPs (due to their size and total charge) to the polycationic carriers (Lipofectamine2000 or L2K) compared to the free siRNA duplexes[14].

Figure 3B:
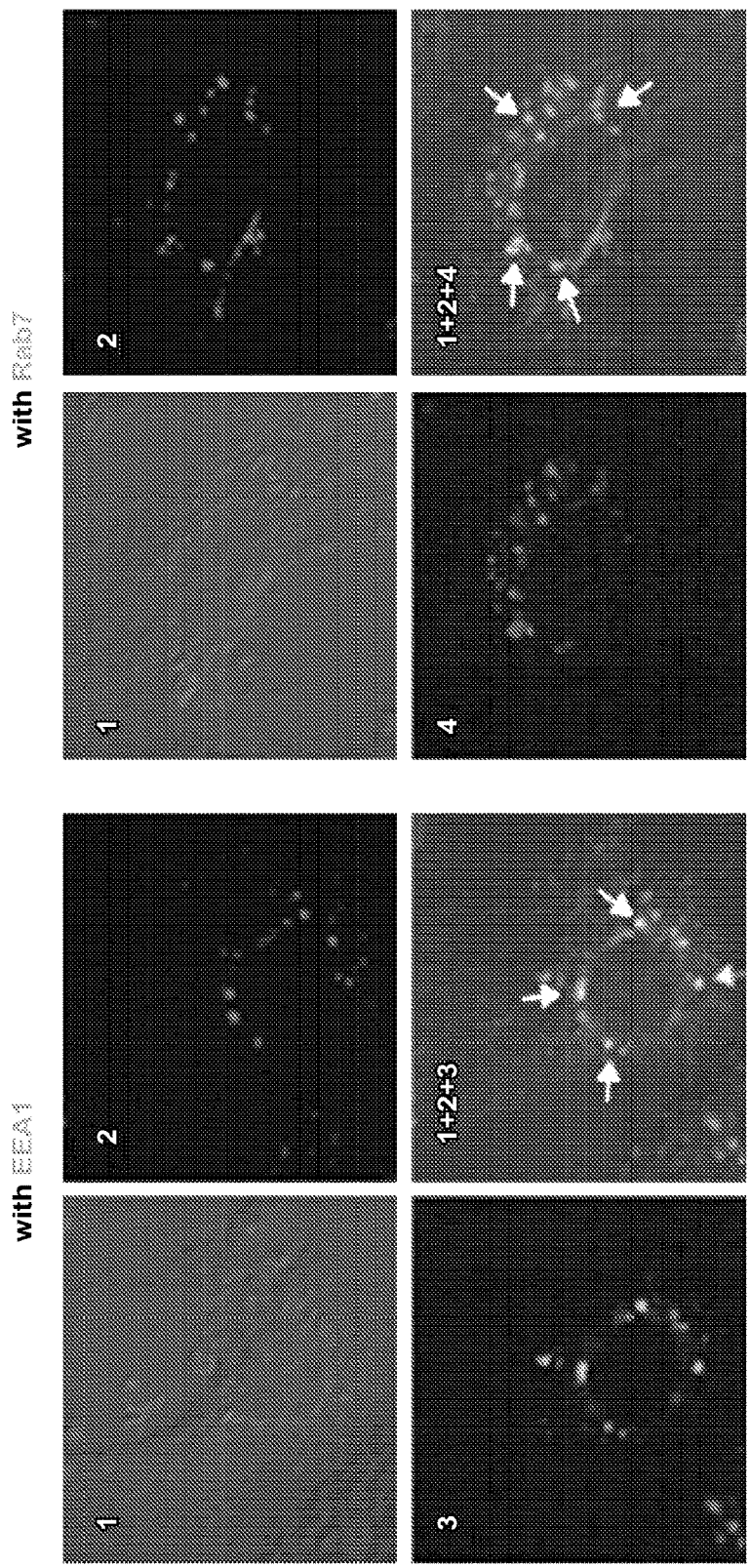
Figure 3C:
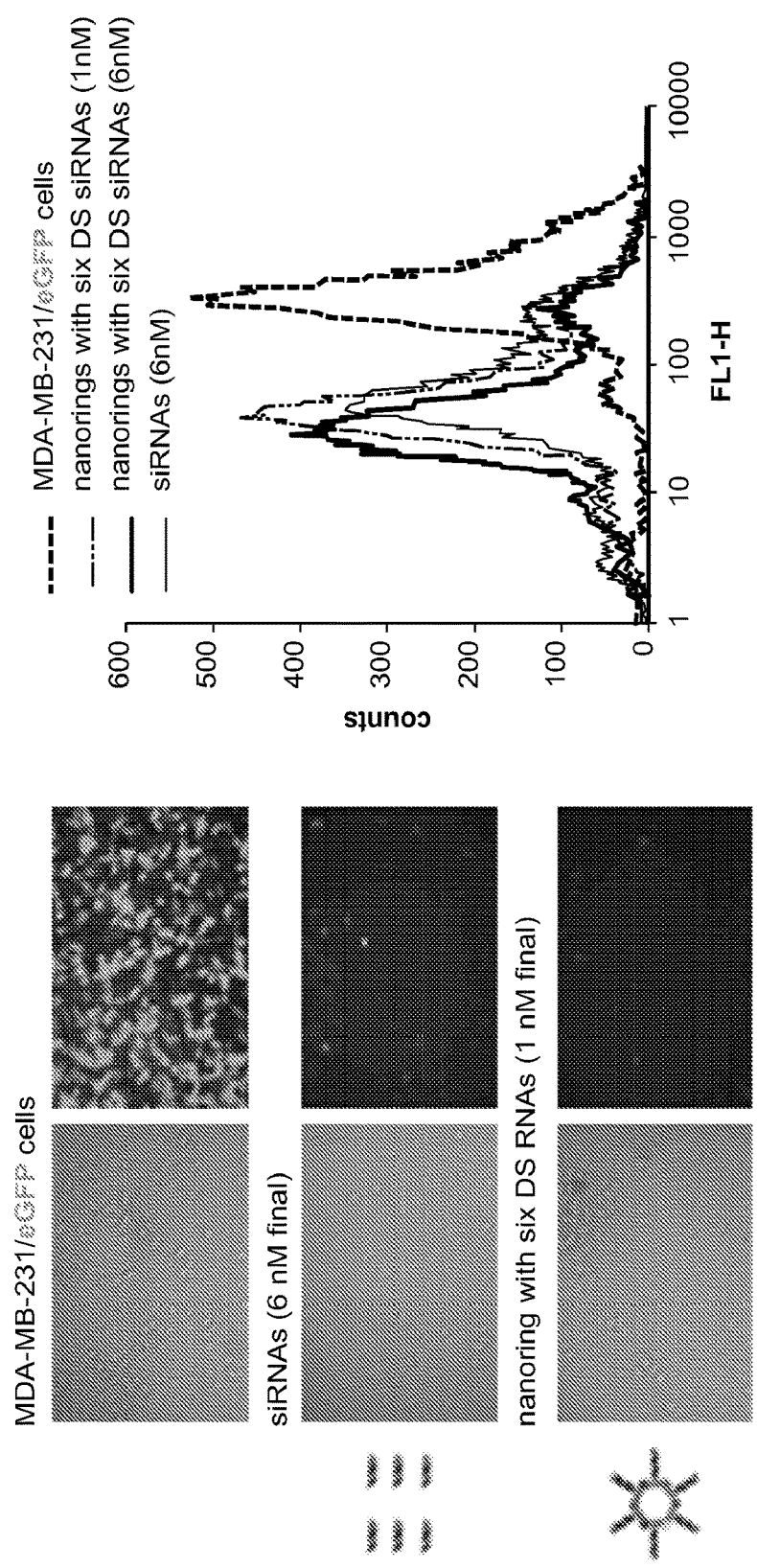
Figure 13A:
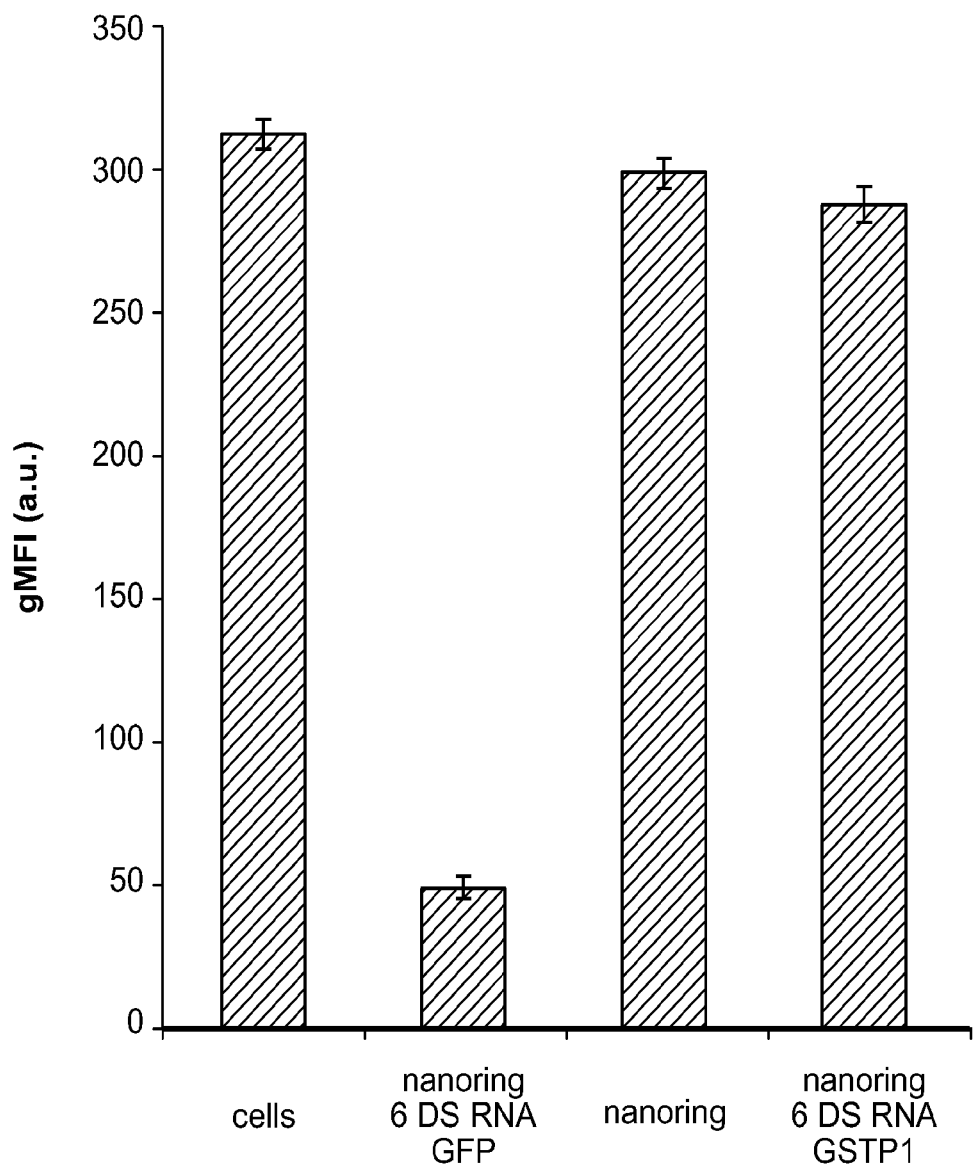
Figure 13C:
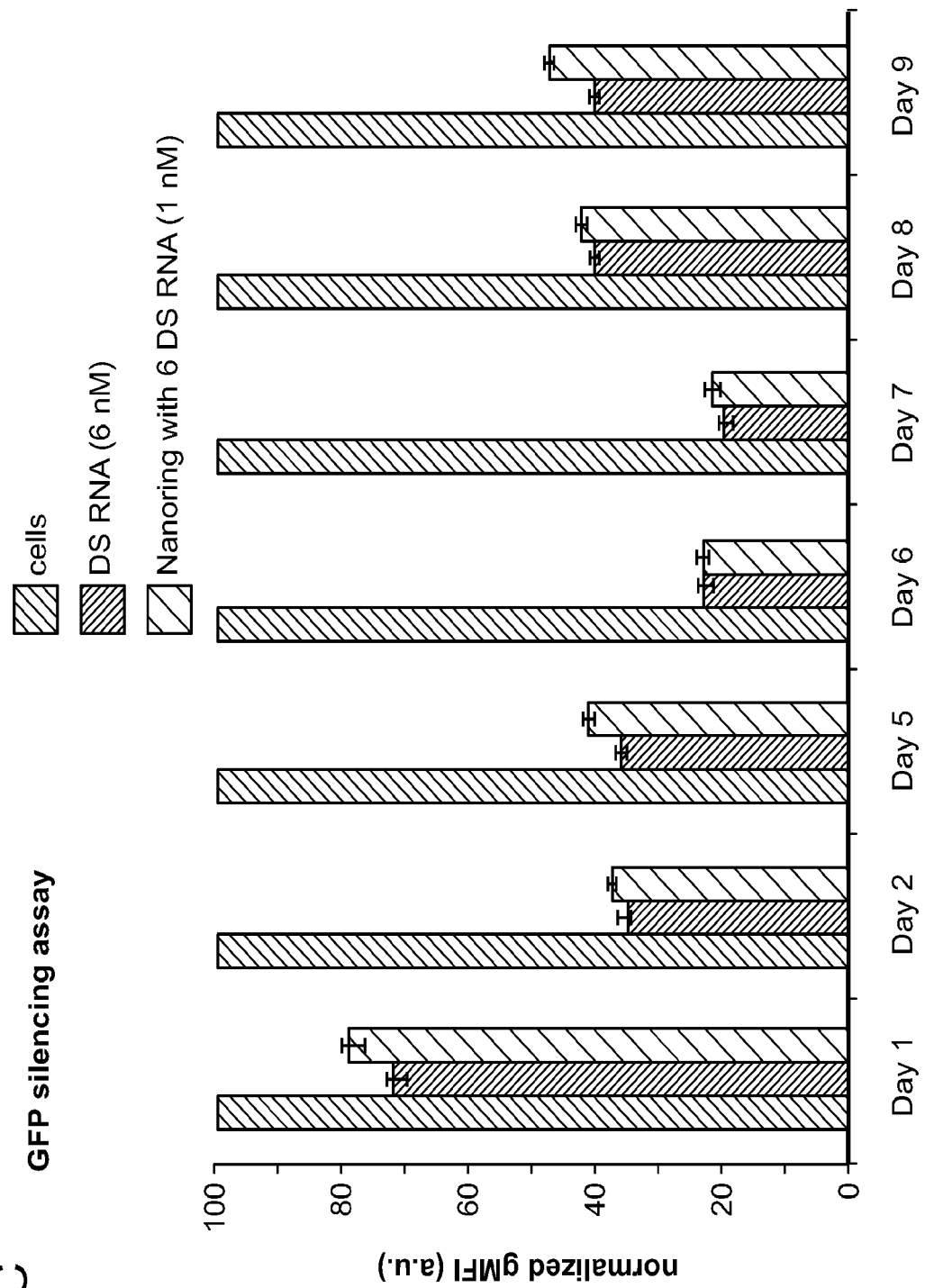
Figure 13D:
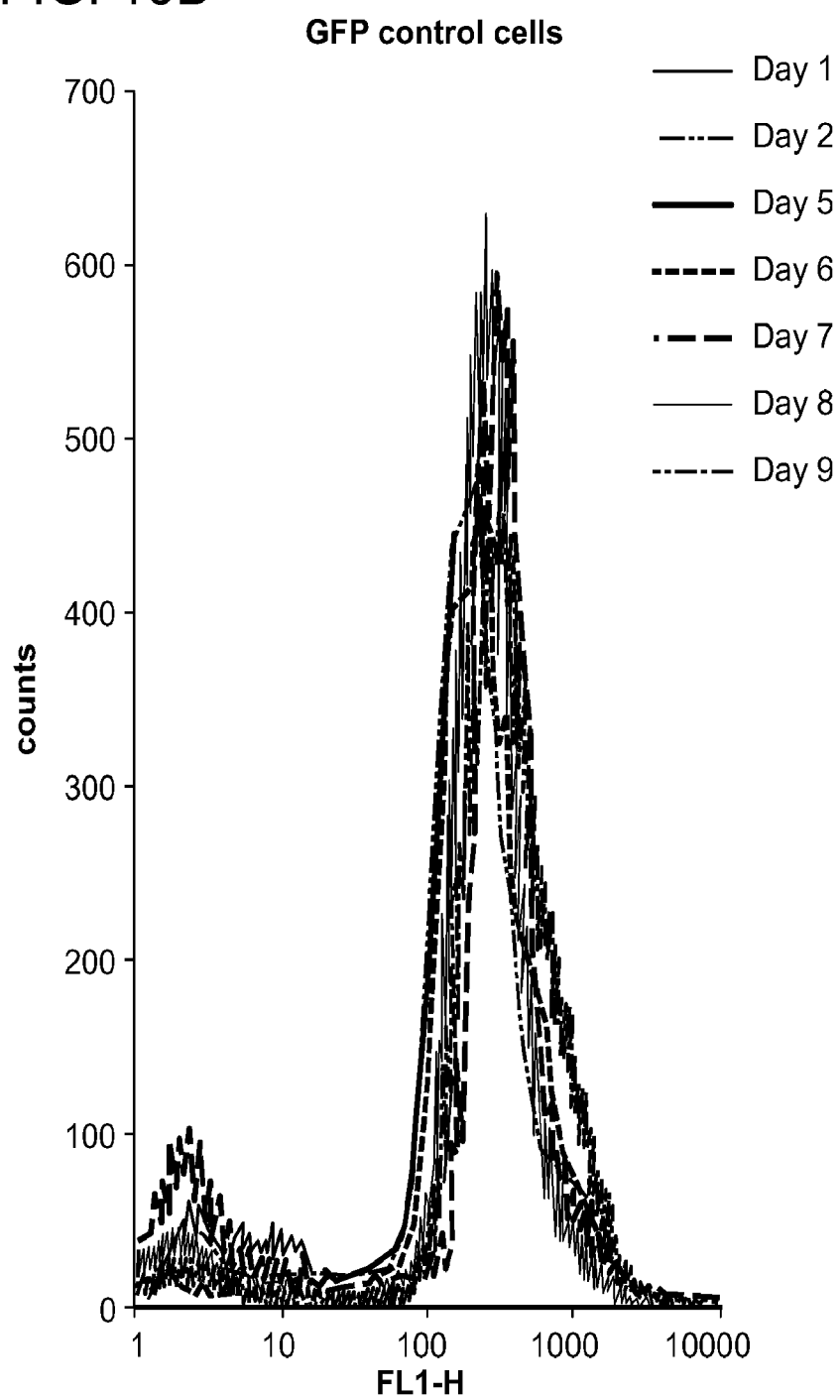

Without wishing to be bound by theory, the use of nanoparticles functionalized with siRNAs provided a precise control over the formulation and higher local concentration of siRNAs, which in turn likely improved the loading of RISC, when presented only in specific cytoplasmic locations (Lee et al. *Nat Cell Biol* 2009, 11, (9), 1150-6; Sen and Blau. *Nat Cell Biol* 2005, 7, (6), 633-6). To assess the release of siRNAs from the functionalized nanorings upon dicing inside the cells, experiments with human breast cancer cells stably expressing enhanced green fluorescent protein (eGFP) were carried out (FIG. 3b and FIGS. 11-12). First, cells were transfected with different concentrations of nanorings carrying six DS RNAs against eGFP and the individual DS RNAs. Due to the use of one-type of siRNA against eGFP, free DS RNAs (or siRNA) are always compared at six-fold higher concentrations than the corresponding functionalized nanorings. After three days, the amounts of eGFP production were examined (FIG. 10). The visual analysis revealed the significant and comparable silencing efficiencies for both DS RNA decorated nanorings and DS RNA duplexes at concentrations as low as 0.75 nM and 4 nM respectively (FIG. 11). In order to statistically compare the extents of silencing, cells transfected with small amounts of functionalized nanorings (1 nM final) and siRNA or DS RNA duplexes (6 nM final) were analyzed with FACS (FIG. 3c and supporting FIG. 12). The results demonstrated significant levels of silencing of GFP at low concentrations of functional RNA nanoparticles (1 nM). As a negative control, the nanorings without DS RNAs and nanorings functionalized with DS RNAs designed against a different gene were used (FIG. 13a). The specific gene silencing was observed only in the case of nanorings designed to target GFP. The functional nanorings had less effect on cell viability compared to DS RNA (supporting FIG. 13b). The effect of gene silencing persisted over a nine day period (supporting FIG. 13c) and was comparable for the functional nanorings and DS RNAs introduced at six times higher concentration. Thus, the results showed that the functionalized nanorings of the present invention were more effective than individual siRNAs. This can be explained by the fact that the use of nanorings locally provides a higher concentration of DS RNAs which in turns improves the loading of RISC, presented only in specific cytoplasmic locations[15, 16]. Interestingly, for cells transfected with nanorings with six DS RNAs, the effect of silencing persisted over a longer period of time (FIG. 12) compared to free DS RNAs. This phenomenon is consistent with previously published results for RNAi activation by the branched RNA nanostructures[17].

Figure 3D:
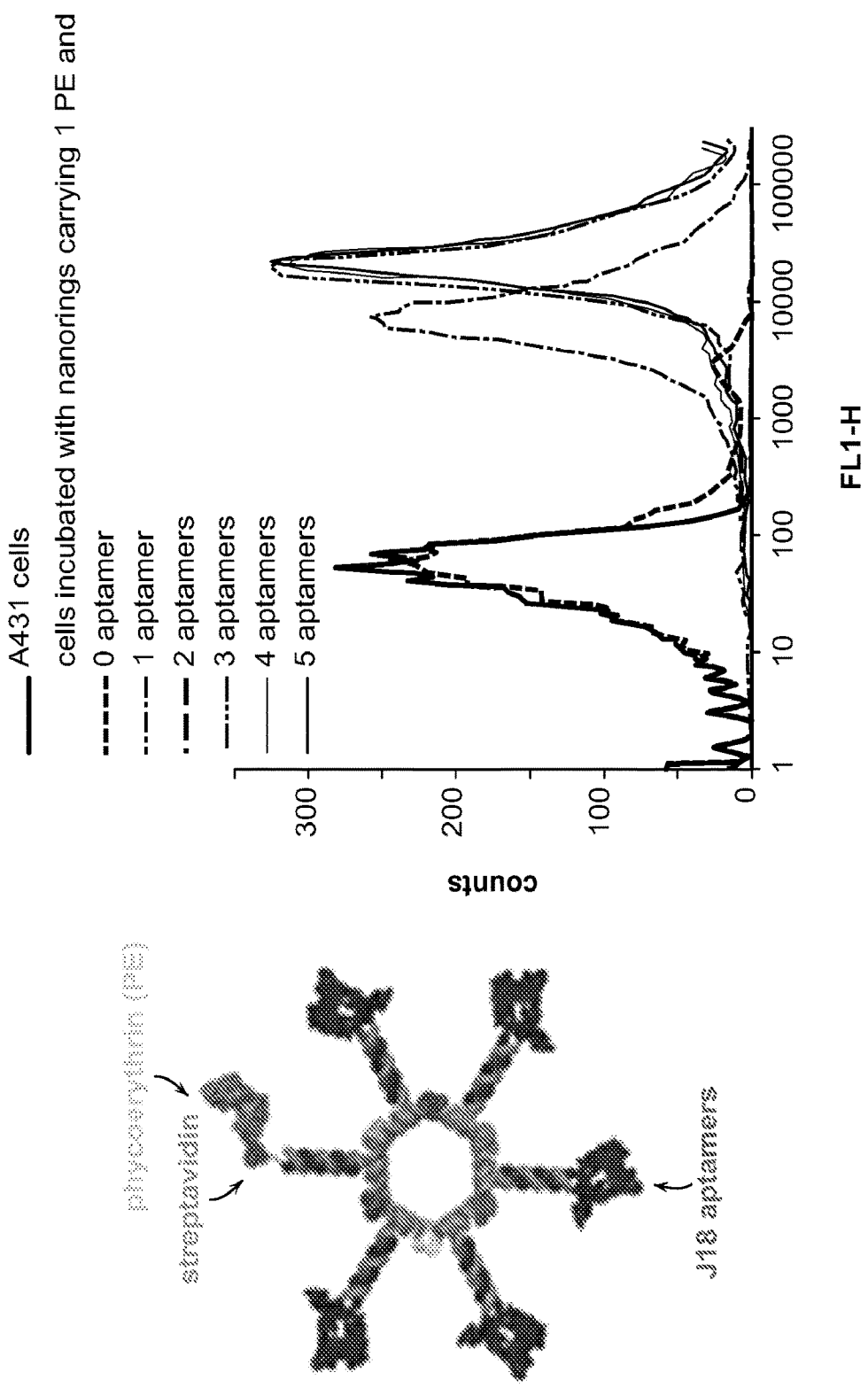
Figure 14A:
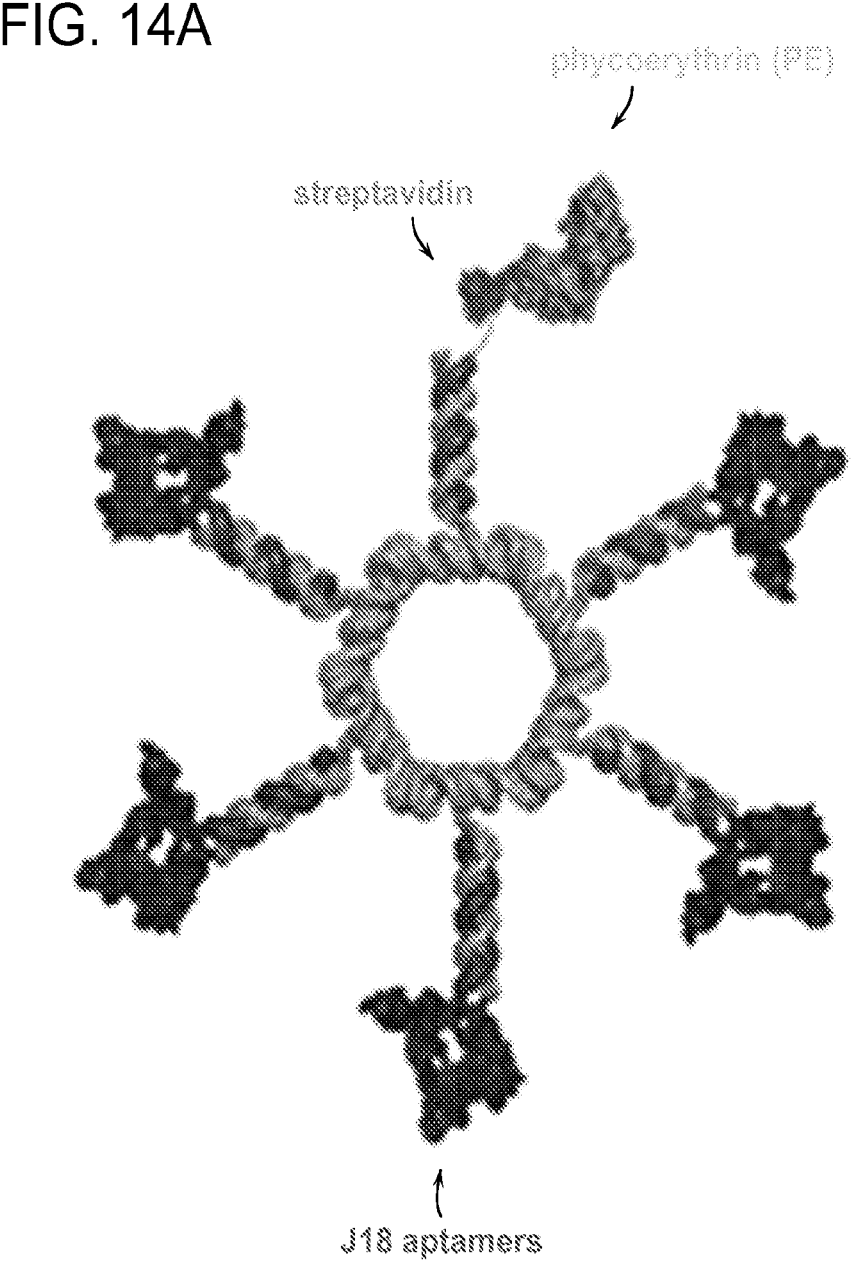
Figure 14B:
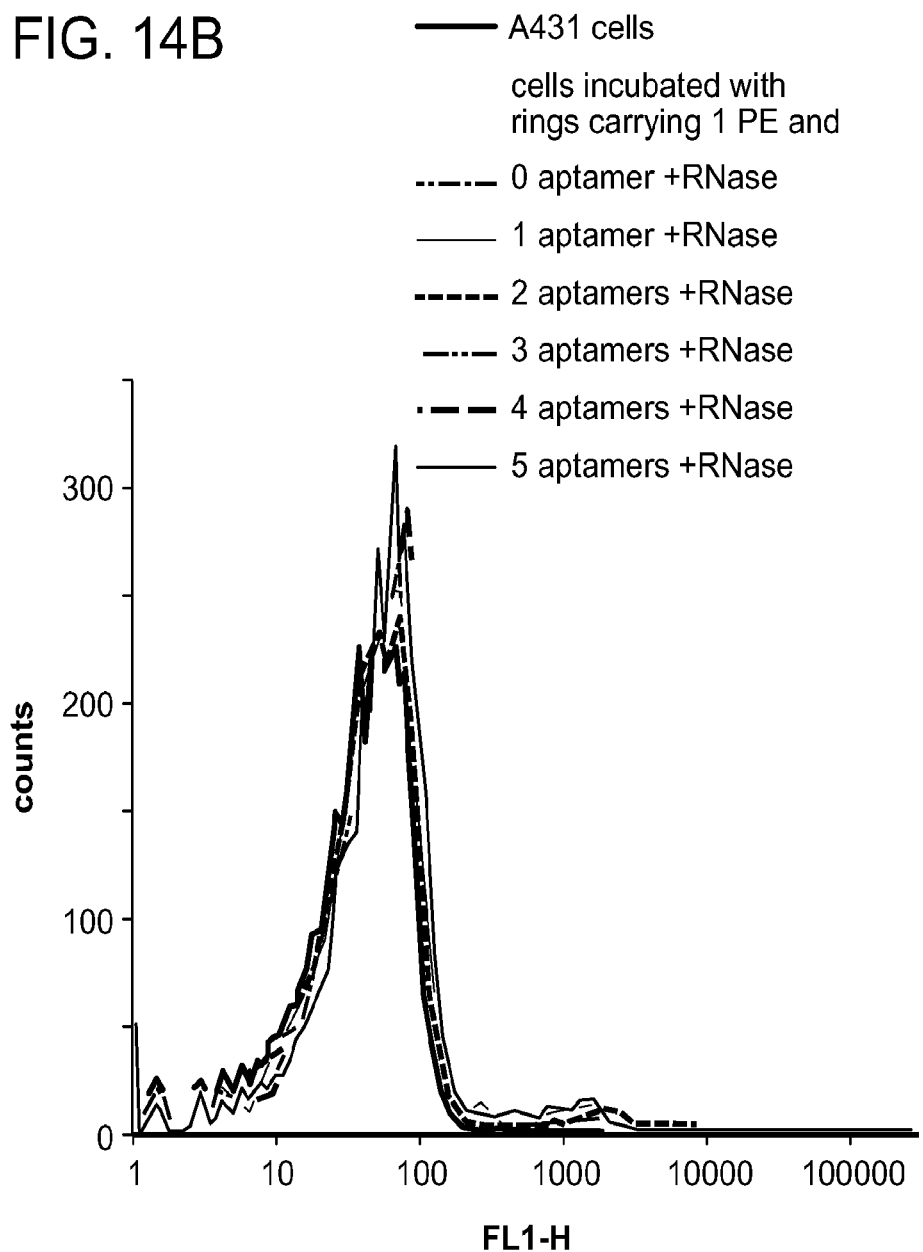
Figure 14C:
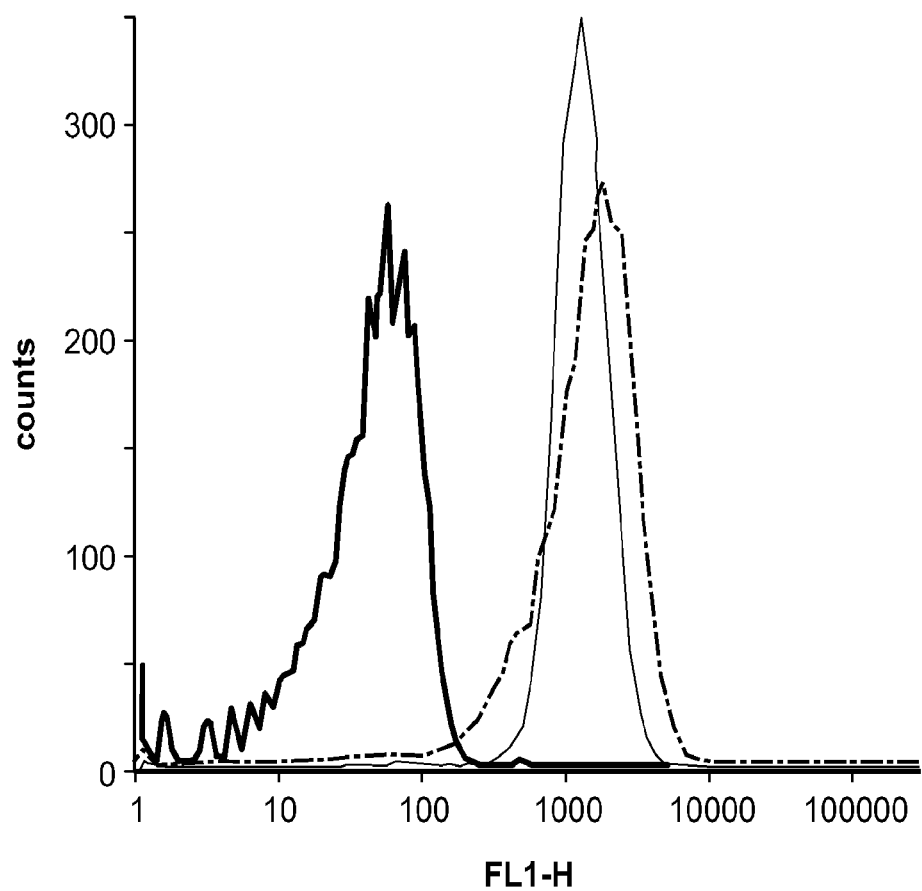
Figure 15A:
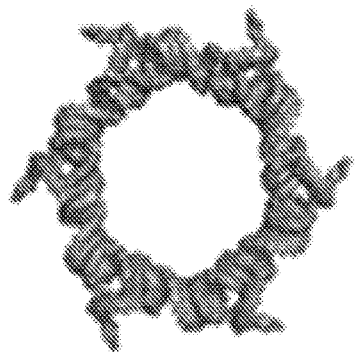
Figure 15A:
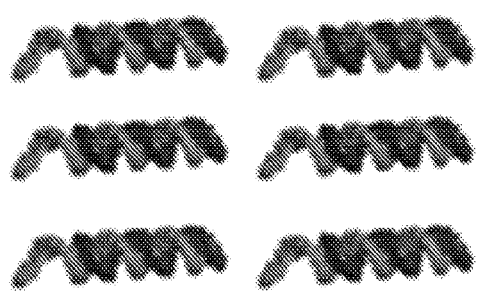
Figure 15A:
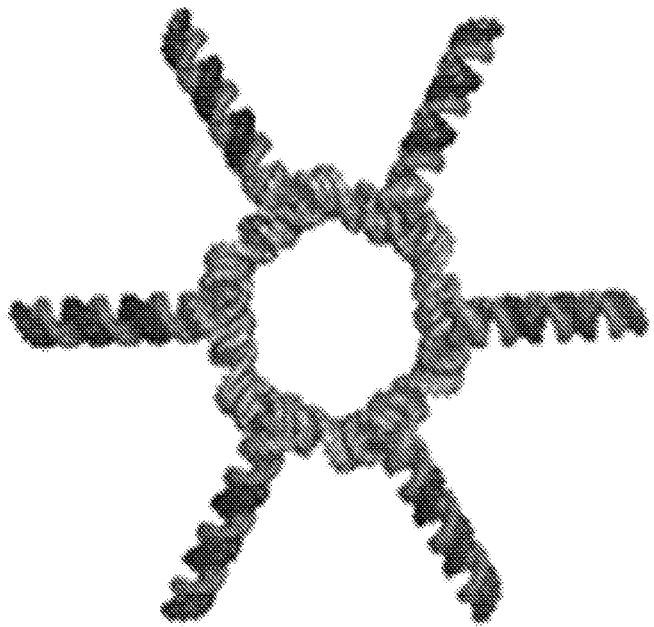
Figure 15B:
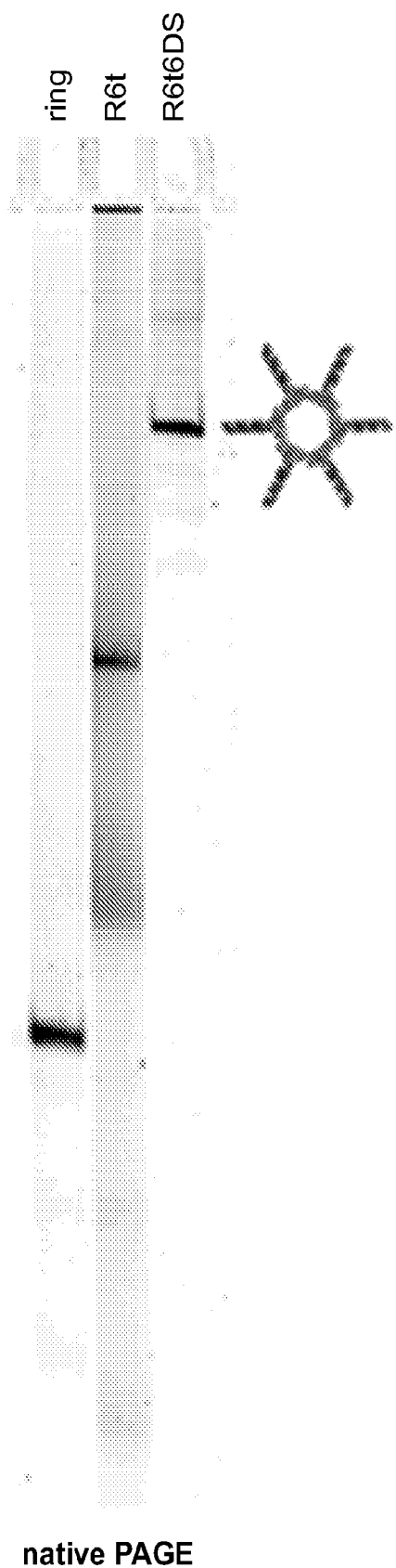
Figure 15C:
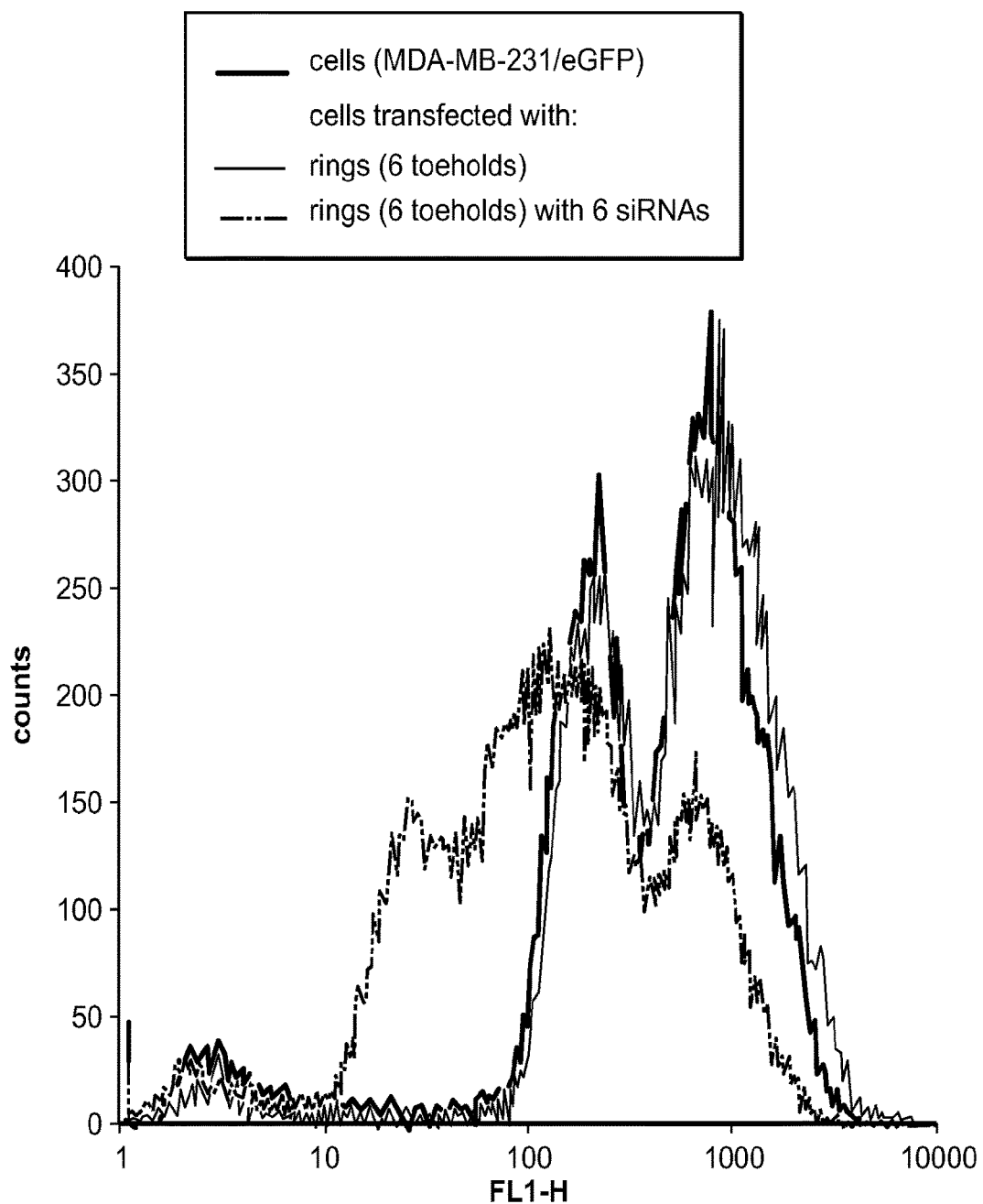

Targeting of nanorings using receptor-specific aptamers was also assessed. Specific targeting of NPs to cells of interest poses important challenges for bio-sensing and potential in vivo application. To demonstrate that NPs can be targeted to specific cells, NPs containing up to five copies of the J18 RNA aptamer that is specific for the human Epidermal Growth Factor Receptor (EGFR) were generated[1]. For visualization, a biotinylated oligonucleotide was coupled to phycoerythrin (PE) through a streptavidin linkage and used in the assembly of nanorings (FIG. 3d and FIG. 14). This coupling system illustrates how protein moieties can be incorporated into the nanoscaffolds. Nanorings were observed to bind to target epidermoid carcinoma cells (A431) that expressed high levels of EGFR. NP with four and five aptamers revealed the strongest signal compared to the rings bearing fewer copies of the aptamers. For example, the fluorescence signal of cells treated with nanorings bearing one aptamer was more than threefold weaker compared to nanorings with four aptamers. This suggested that higher numbers of aptamers per NP provide higher binding affinity to target cells. These results indicated that binding of NPs to cells was mediated by the RNA aptamer molecule since co-treatment of cells with RNases led to a complete loss of fluorescence (FIG. 14b). Loss of signal was due to the enzymatic degradation of RNA molecules and not their target, since monoclonal antibodies against EGFR detect EGFR in presence of RNases (FIG. 14). Furthermore, addition of recombinant Epidermal Growth Factor (rEGF), a ligand for EGFR, led to a decrease of the fluorescent signal (FIG. 12c), suggesting that rEGF competed with the J18 aptamer in binding to the cellular EGFR. The decrease of the signal was not caused by nonspecific degradation of the aptamer by rEGF, since the presence of an unrelated recombinant protein (rIgG) had no negative effect on NP binding. A similar effect was also seen for cells treated using PE labeled J18 aptamers (data not shown).

Example 3. Functionalization of Nanorings Through Toehold Interactions

In addition to synthesizing the nanoring scaffold monomers concatenated with the DS RNA strands, it is possible alternatively to functionalize the nanoring scaffolds through toehold interactions. This system of attachment allows for the multi-functional use of a single nanoscaffold since different nucleic acid functionalities can be joined as long as they bear the cognate toehold complementary to the one found in the nanoscaffold. To demonstrate this, the six scaffold monomers were engineered to carry 10 nt single-stranded RNA (ssRNA) toeholds on the 3' end, which were designed to anneal to a complementary toehold sequence in the antisense component of the GFP DS RNAs (FIG. 14). With this method of assembly, the same nanoring scaffold can be packaged with several different functionalities based upon toehold recognition. Additionally, the length of the scaffold strands can be reduced with this bipartite assembly process as the siRNA components are no longer concatenated, which increases efficiency of synthesis. To confirm the formation of the nanoring construct with six GFP DS RNAs annealed at the 3' ends, native-PAGE was performed using nanorings with and without toeholds as the controls. The release of siRNAs upon dicing of the annealed DS RNAs was confirmed by GFP knockdown assays. FIG. 15 shows functionalization of nanorings through toeholds interaction.

Figure 4A:
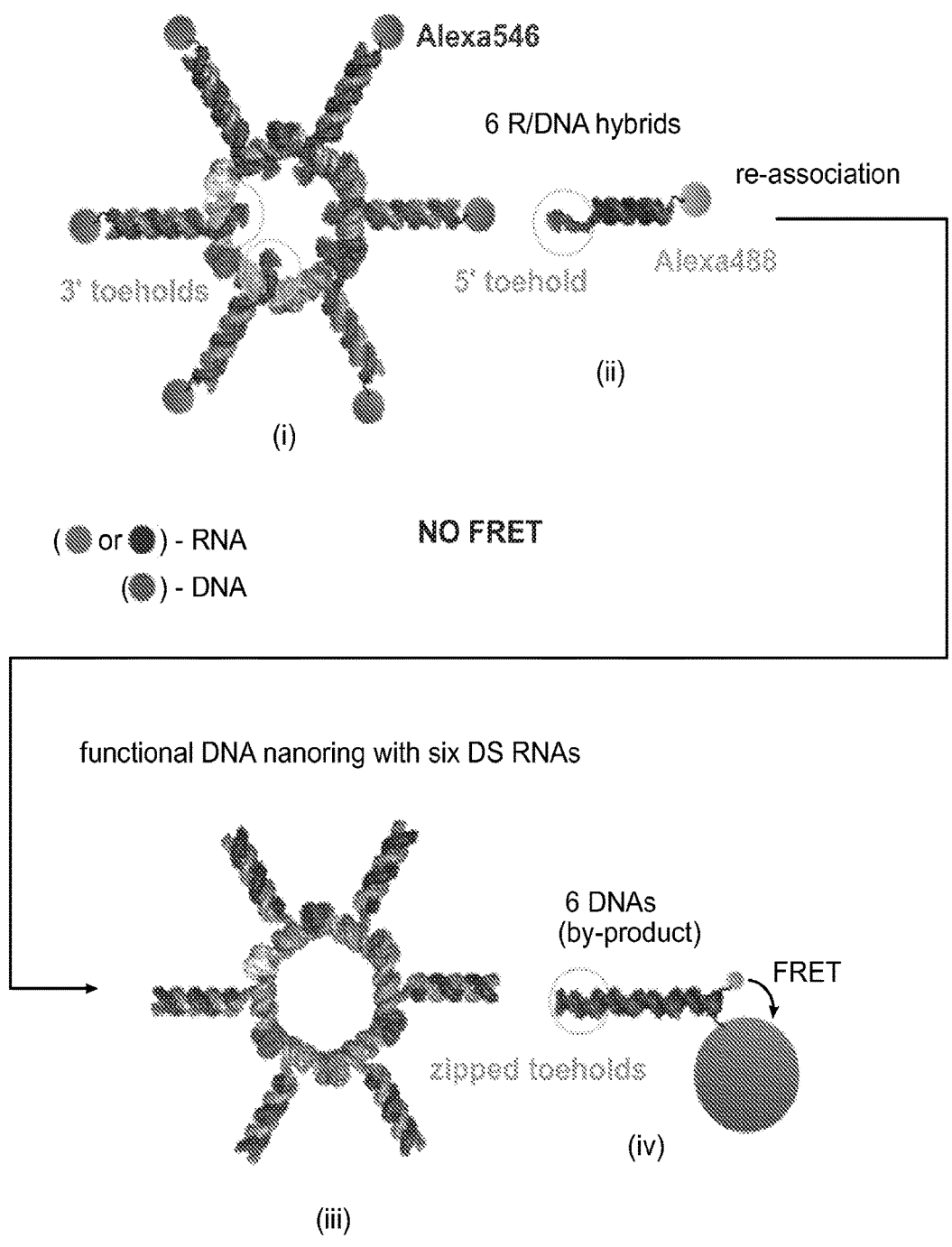
FIG. 4 shows activation of different functionalities by R/DNA hybrids. (a) Scheme showing an activation of multiple functionalities (RNAi, FRET) upon re-association of non-functional nanorings decorated with RNA-DNA (R/DNA) hybrids and six non-functional R/DNA hybrids. (b) FRET time traces during re-association of auto-recognizing R/DNA nanoring and six R/DNA hybrids labeled with Alexa546 and Alexa488. (c) FRET experiments: cells were co-transfected with auto-recognizing R/DNA nanoring and six R/DNA hybrids labeled with Alexa546 and Alexa488 and images were taken on the next day. (d) GFP knockdown assays for human breast cancer cells (MDA-MB-231/GFP) which stably express enhanced GFP (eGFP). Three days after the transfection of cells with auto-recognizing R/DNA nanoring and R/DNA hybrids programmed to release DS RNAs against eGFP, eGFP expression was statistically analyzed with flow cytometry experiments. As the control, DS RNA duplexes against eGFP were used. Please note that the individual R/DNA nanoring and R/DNA hybrids cause no decrease in eGFP production. Image numbers in (c) correspond to: differential interference contrast (DIC) images (1), Alexa488 emission (2), Alexa546 emission (3), bleed-through corrected FRET image (4), 3D chart representation of zoomed fragment indicated by a white box of bleed-through corrected FRET image with the yellow star indicating the correspondence (5).

Example 4. Controlled, Conditional Activation of Intracellular FRET and RNAi by Nanorings with RNA-DNA Hybrids Additional control over activation of different functionalities can be achieved by using the recently developed technique based on RNA-DNA hybrids[12]. In this scheme, multiple functionalities have been split-DS RNAs and a Förster resonance energy transfer (FRET) pair between an RNA-DNA nanoring and hybrid, thus deactivating the functionalities (FIG. 4a). Dicer is an RNaseIII-like enzyme, which is incapable of processing the RNA-DNA hybrids[12, 18] to make them loadable into the RISC. The strands of DS RNAs concatenated to the 3'-end of the nanoring monomers, are annealed to the complementary DNAs thus, preventing Dicer from processing these duplexes and making the nanorings nonfunctional. These DNAs contain single-stranded 3'-end toeholds complementary to the toeholds situated at 5'-ends of the DNAs forming hybrids with the senses of the DS RNAs. In addition to splitting the DS RNA, a FRET pair (Alexa488 and Alexa546) has been separated between the non-functional RNA-DNA rings and hybrids through the conjugation of dyes to DNA components. The ssDNA complementary toeholds when in close proximity can recognize each other and trigger re-association. This results in the simultaneous formation of DS RNAs functionalized nanorings together with a FRET induction.

Figure 4B:
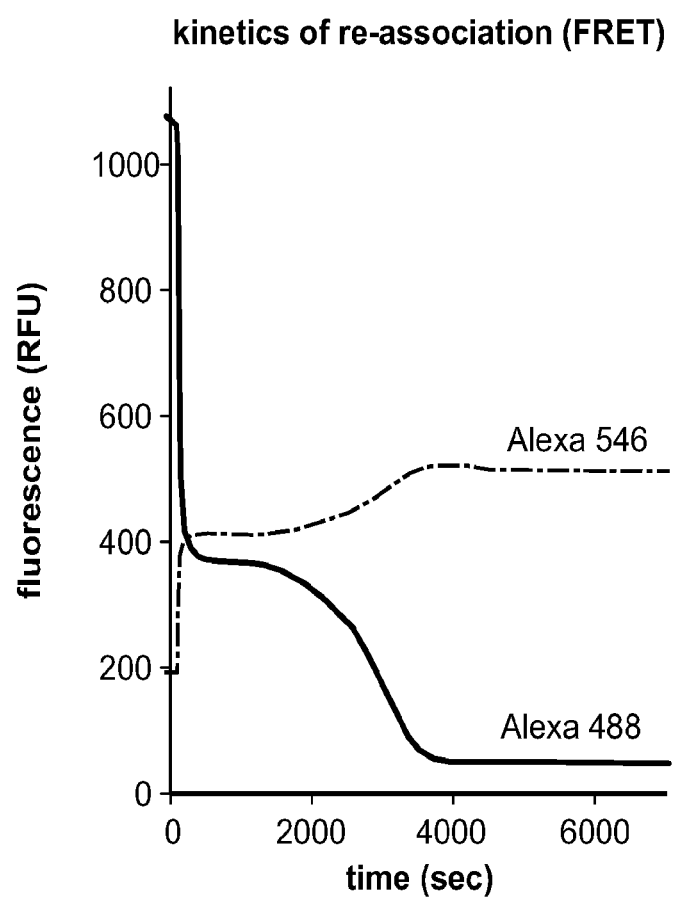
Figure 4C:
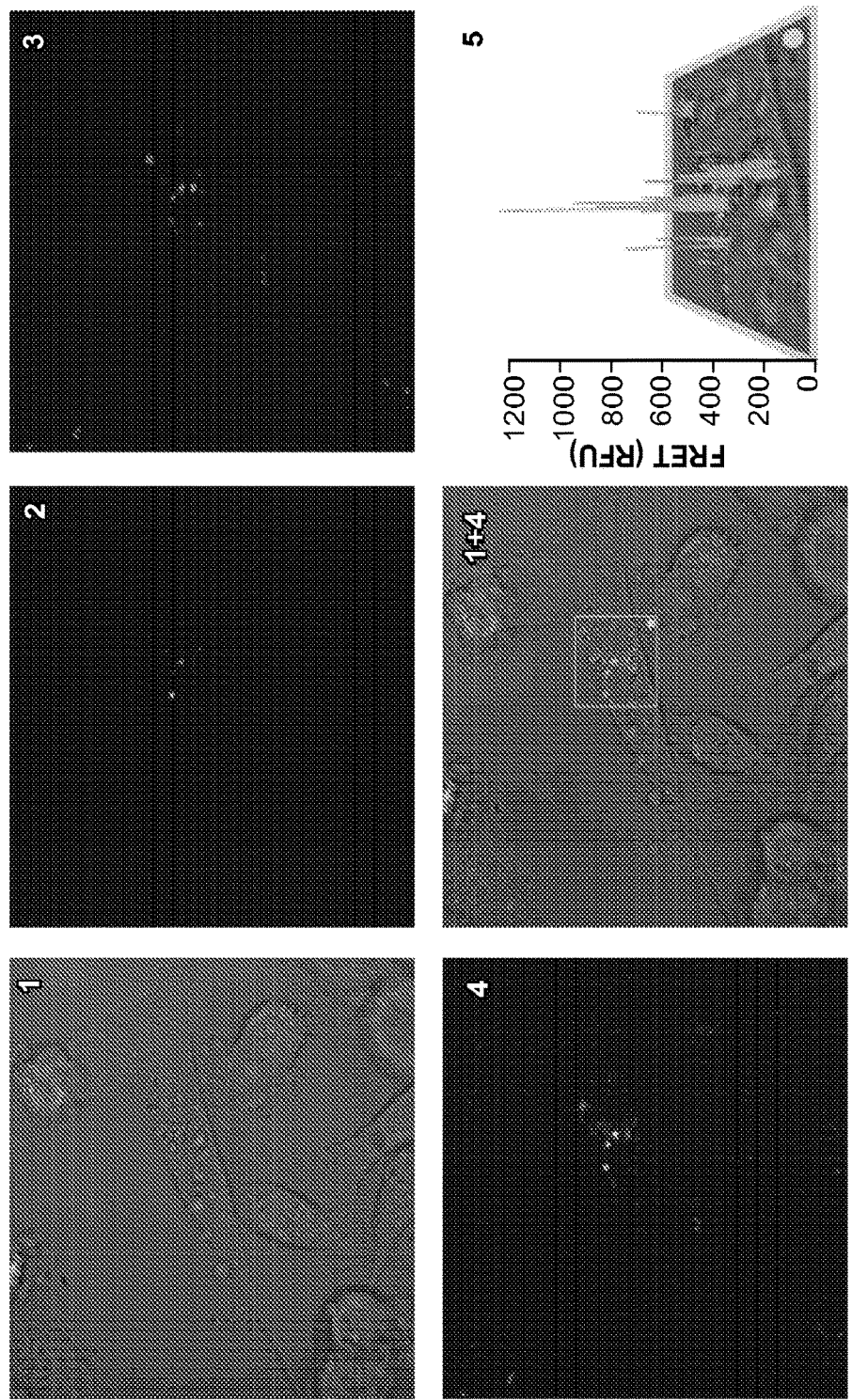

To follow the re-association in real time, FRET time-traces were performed. The 5'-end of the antisense-binding and the 3'-end of sense-binding DNA strands were fluorescently tagged with Alexa546 and Alexa488, respectively. When the nonfunctional RNA-DNA ring was mixed with six RNA-DNA hybrids, the dsDNA formation brought Alexa488 within the Förster distance ($R_0$=6.31 nm) of Alexa546. As a result, the emission of Alexa546 increased while the signal of Alexa488 dropped (FIG. 4b). The results of FRET time-traces revealed a quick burst phase of partial re-association followed by a more complete pairing of fluorescent tags. To visualize intracellular re-association, non-functional RNA-DNA rings and hybrids labeled with Alexa546 and Alexa488 (FIG. 4c) were co-transfected into MDA-MB-231 cells and examined by confocal microscopy the next day. The FRET signal after bleed through correction was calculated as detailed previously and is presented in FIG. 4c (1+4 and 5).

Figure 4D:
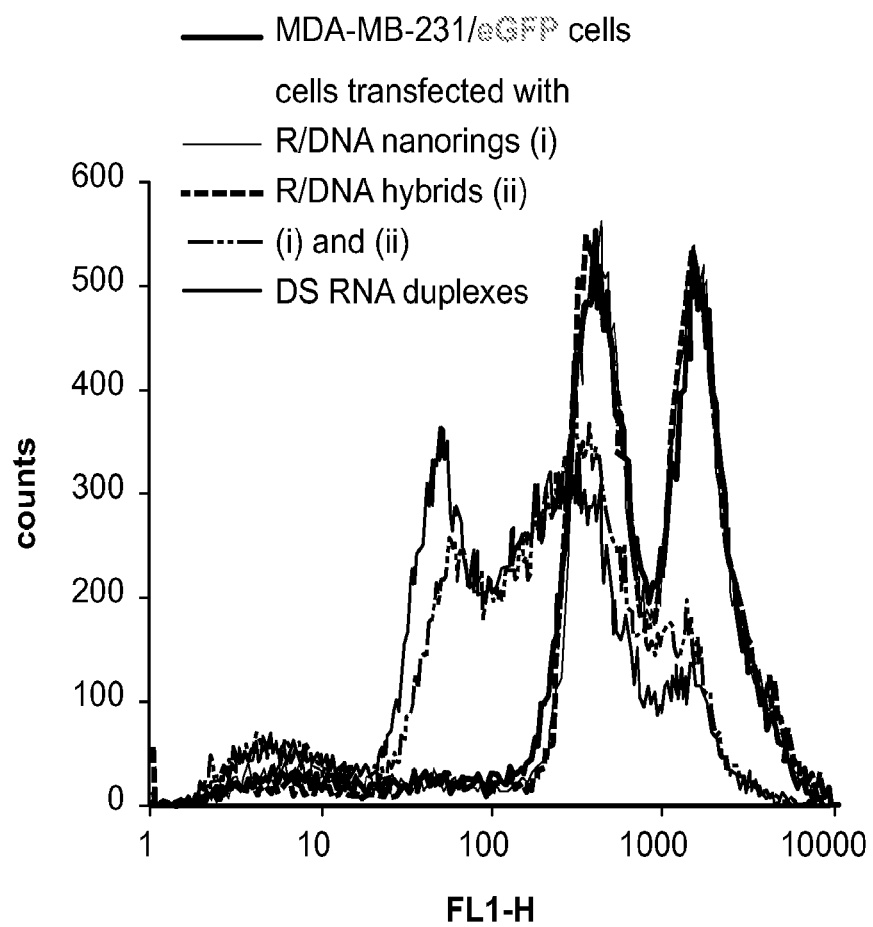

To gauge whether the cognate hybrid rings and duplexes can intracellularly recombine to form functional DS RNA nanorings, human breast cancer cells stably expressing eGFP were co-transfected with the non-functional components (FIG. 4d). Cells were also separately treated with the hybrids ring or hybrid to determine whether the individual components could induce knockdown of eGFP expression. Three days after transfection, the level of eGFP expression was measured with flow cytometry. The results demonstrate no silencing of eGFP production caused by the individual components. However, when cells were co-transfected with separately prepared complexes of L2K/hybrid rings and L2K/hybrids, the level of silencing measured after three days was comparable to the silencing resulting from the transfections with control, pre-formed GFP siRNAs.

Example 5. Implementation of Functional Nanorings In Vivo

Figure 5:
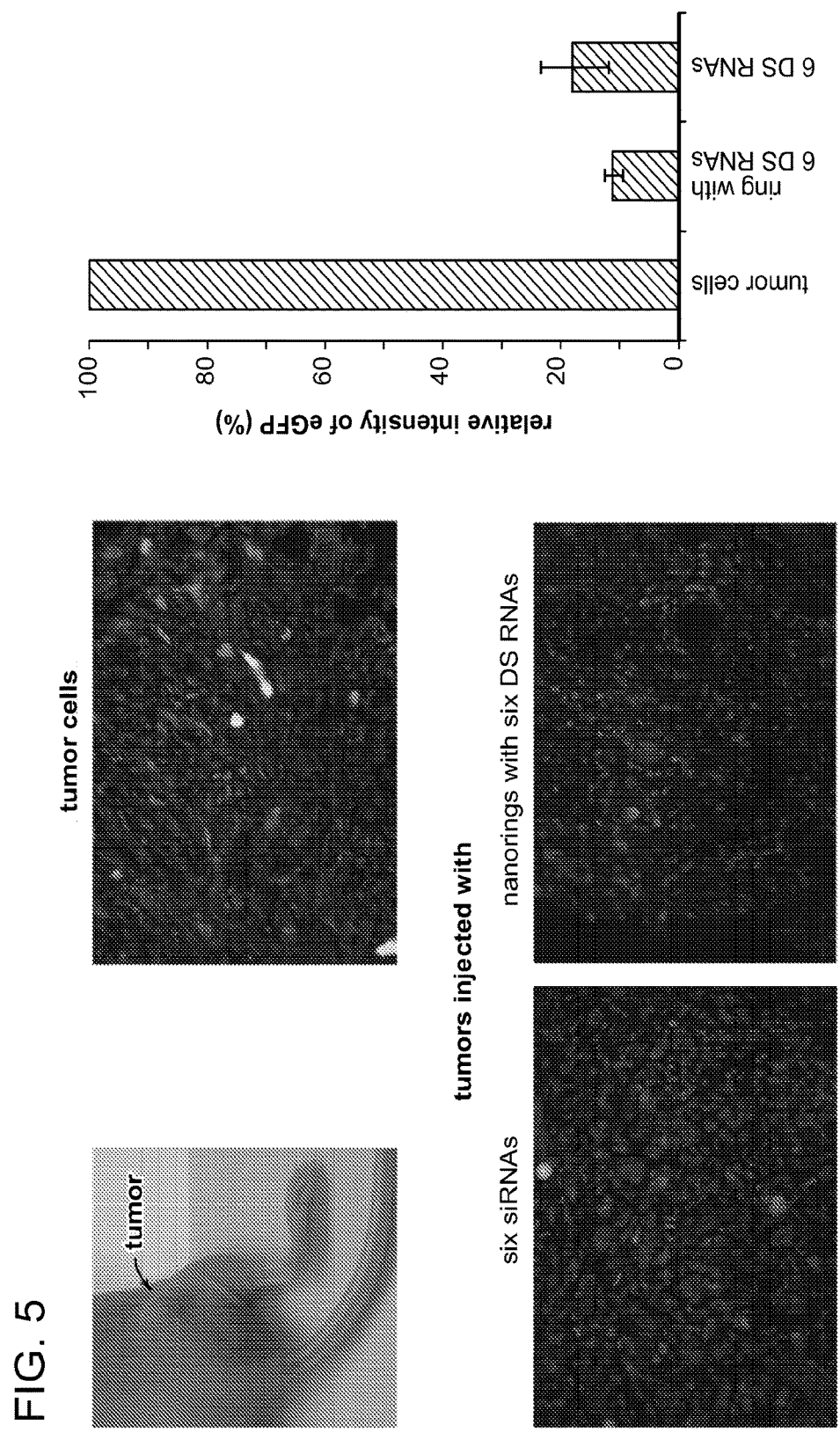
FIG. 5 shows in vivo studies of nanorings functionalized with six siRNAs in tumor xenograft mouse model. Fluorescent imaging of tumors and corresponding quantification after five days post-injections in vivo demonstrate higher levels of eGFP silencing caused by nanorings functionalized with six siRNAs compared to free siRNAs. Please note that the free siRNA duplexes are at six times higher concentrations than corresponding nanorings with six siRNAs.
Figure 6:
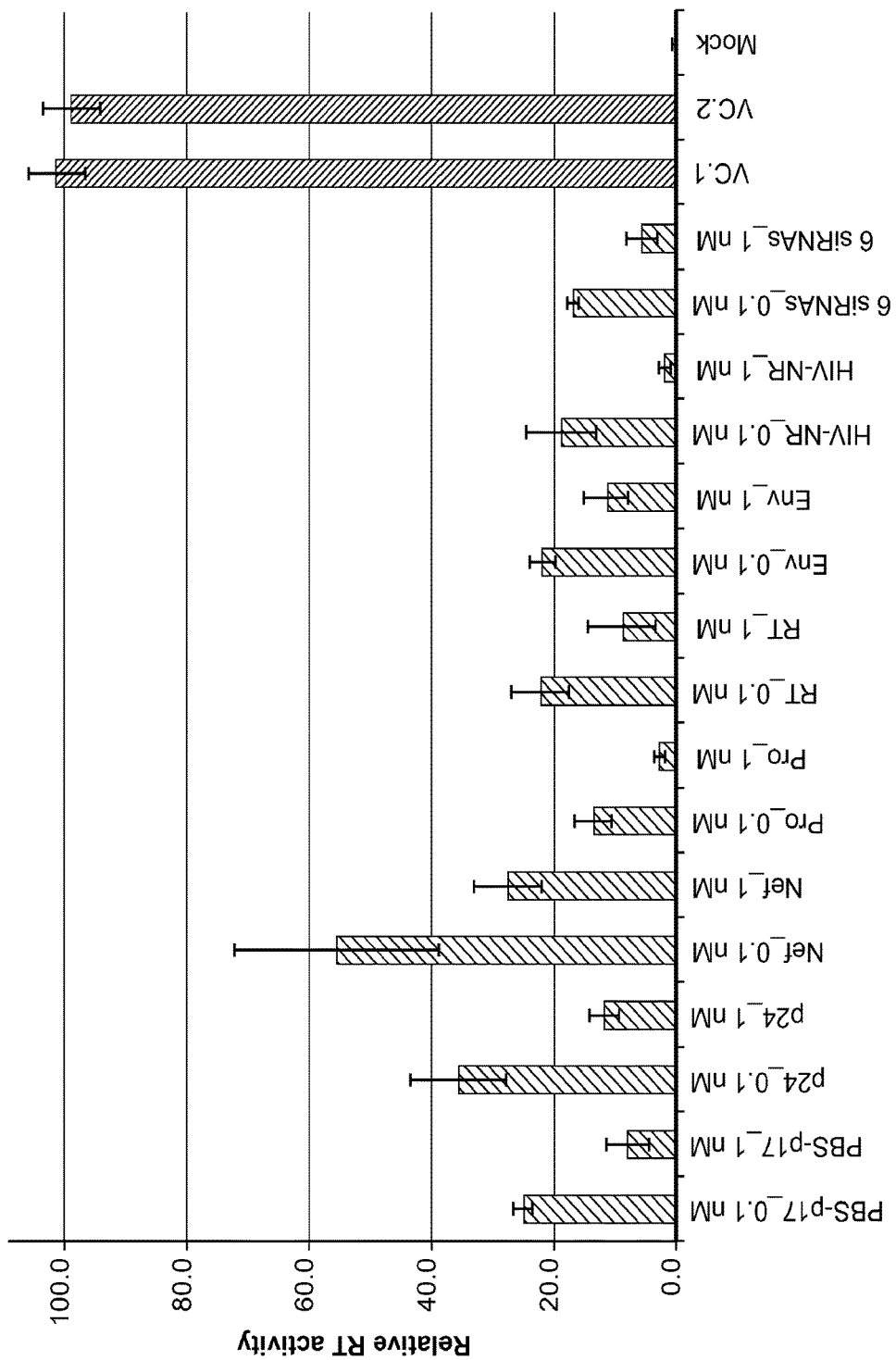
FIG. 6 shows HIV-1 expression and production is inhibited by individual duplex siRNAs and anti-HIV-1 Nanorings (NR-HIV). Different sites were targeted in the Gag and Pol mRNA. Nef and Env mRNAs were also used as targets. Nanorings contain all 6 siRNAs. HeLa cells were transfected with pNL4-3, with and without siRNAs. Virus supernatant was harvested and RT activity was measured; data are shown normalized to virus controls (VC.1 and VC.2) without siRNAs. (PBS—primer bind site; p17-Matrix; p24-Capsid; Pro-Protease; RT-Reverse Transcriptase; Env-gp120 and concentrations used 0.1 and 1 nM).
Figure 7:
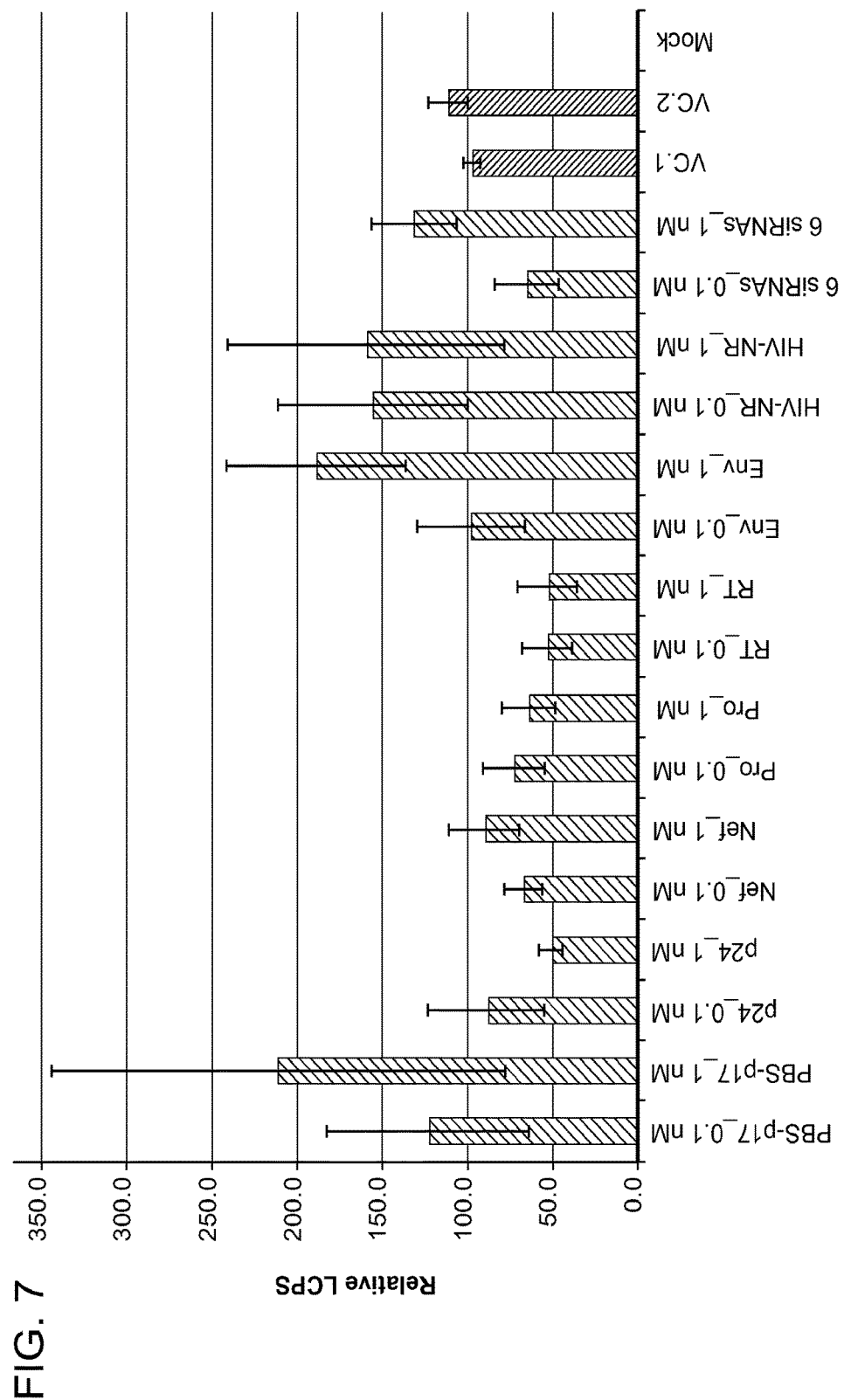
FIG. 7 shows cytotoxicity of individual duplex siRNAs and anti-HIV-1 Nanorings. LCPS (luciferase counts per second) in HIV-1-expressing HeLa cells co-transfected with pNL4-3 and psiCHECK™-1 (Promega), with and without siRNAs. At 48 h post transfection, cells were lysed and Renilla luciferase was measured. (PBS— primer bind site; p17-Matrix; p24-Capsid; Pro-Protease; RT-Reverse Transcriptase; Env-gp120; HIV-NR-Nanorings; 6 siRNAs—Mix of 6 different siRNAs and concentrations used 0.1 and 1 nM).

Additionally, in vivo gene silencing was performed in athymic nude mice bearing xenograft tumors expressing GFP (FIG. 5). Functionalized nanorings and control siRNAs were administered by intra-tumor injections into different mice. Five days after, the silencing efficiencies were analyzed ex vivo by measuring the fluorescent intensities of native eGFP in treated tumors compared to the tumor of a control animal. Both injections resulted in a significant decrease in GFP fluorescence intensities of ~90% for functionalized nanorings and ~80% for control siRNAs. These results were in a good agreement with the multiple experiments with cell cultures, confirming an efficient delivery and further silencing of target genes by functionalized nanorings.

Example 6. Functional Nanorings Against HIV-1

Figure 8A:
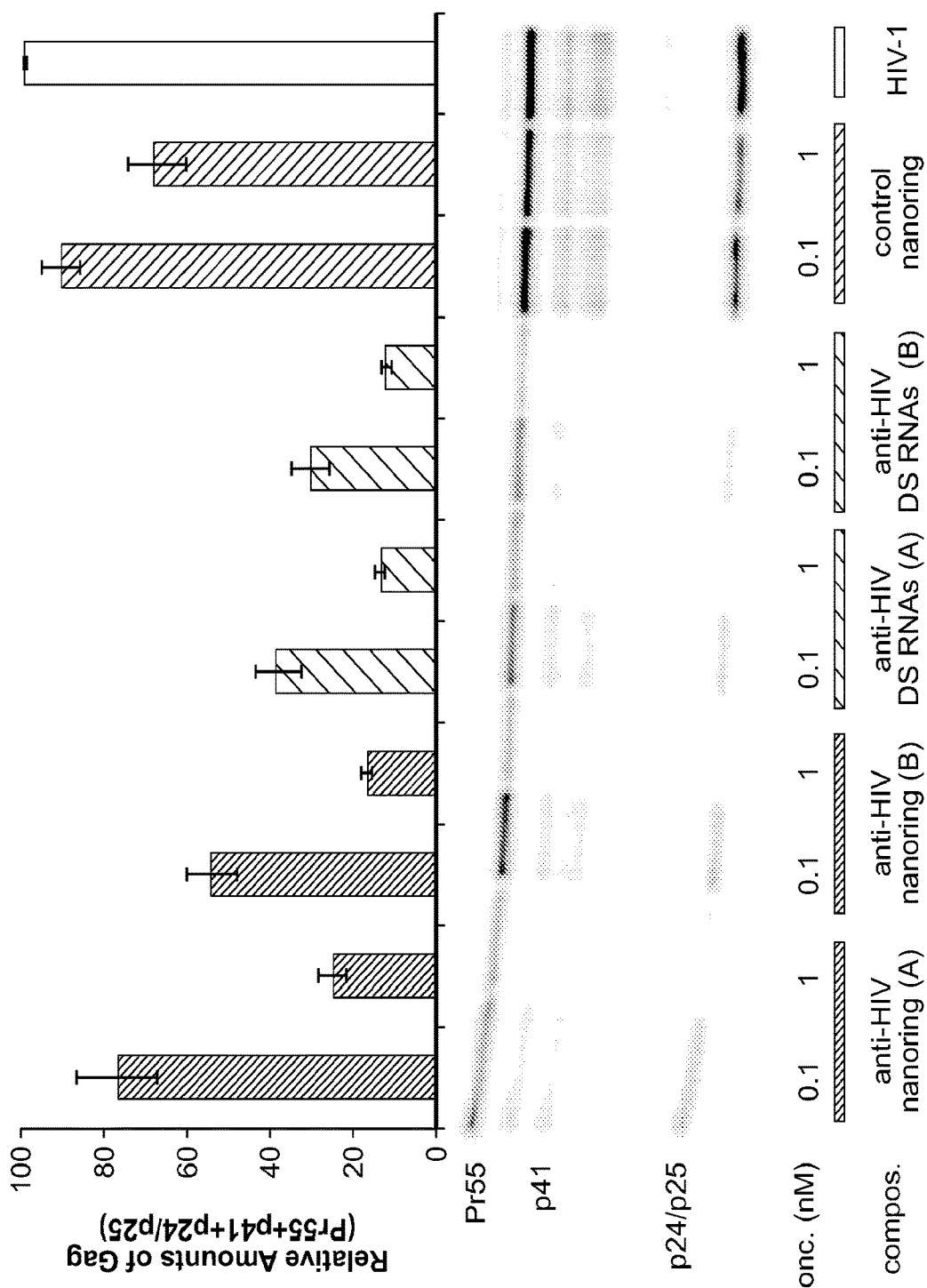
FIG. 8 presents additional histograms showing that HIV-1 expression and production was inhibited by functional nanorings (a) HIV-1 expression inside the cell was measured at 48 h post-transfection. HeLa cells were lysed and probed by western blotting for HIV-1 proteins. Positions of Pr55Gag (Pr55), matrix-capsid (p41) and capsid/capsid-SP1 (p24/ p25) are indicated. Quantification of total cell-associated Gag: Pr55+p41+p25+p24. Total Gag in virus control (HIV-1) without nanorings or dicer substrate (DS) RNAs set at 100. Error bars denote +/−SEM; N=4. (b) HeLa cells were transfected with pNL4-3 (full-length HIV-1 molecular clone), with and without nanorings or DS RNAs. Virus supernatant was harvested 48 h post-transfection and the reverse transcriptase (RT) production was measured (this assay quantifies the amounts of virus produced by the cells); data are shown normalized to virus controls (HIV-1) without functional nanorings or DS RNAs. Mock represents untransfected HeLa cells. Corresponding mixtures of six different anti-HIV DS RNAs (A and B) were used as positive controls. Nanoring control without any anti-HIV DS RNAs was used as a negative control. Error bars denote +/−SEM; N=4.

To show the feasibility of the nanorings, a set of two nanoring constructs (designated as nanorings A and B) were developed and functionalized with a different composition of DS RNAs as specified in the below Methods section. Each nanoring targeted six different regions of HIV-1: PBS-Matrix, Capsid, Protease, Reverse Transcriptase, Envelope, Nef and Rev-Tat. The experiments performed with these nanorings demonstrated a 74-83% decrease in virus protein expression inside transfected cells, for both nanorings A and B at 1 nM concentrations (FIG. 8a). The levels of HIV-1 structural proteins (Gag) were quantified (55 kDa Gag precursor+matrix/capsid p41+capsid, capsid/SP1 p24/p25) to evaluate the efficiency of protein knockdown. Both nanorings were able to inhibit HIV-1 production in the supernatant. Virus inhibition reached levels of ~100% at 1 nM concentrations of nanorings. Values were comparable to background levels detected by the assay (FIG. 8b). These results were equivalent to the levels of inhibition achieved by the controls, a mixture of six corresponding DS RNAs. Under lower concentrations of the nanorings (0.1 nM), virus production was inhibited 71-75%. Cytotoxicity was minimal for nanoring B at 1 nM concentration, highlighting the specificity of the knockdown (FIG. 18).

Methods

The foregoing experiments were carried out with, but not limited to, the following methods and materials.

RNA Nanoring Sequence Design Assemblies and Native PAGE.

The detailed design and production of RNA strands entering the composition of nanorings functionalized with six siRNAs is comprehensively described elsewhere[4]. The full list of RNA sequences used is available, and is shown below.

Bold letter sequences indicate kissing loop regions.

3' Antisense Dicer Substrate RNA (EGFPS1)[24, 25] Modifications of RNA Rings

```
(((((((......))))))) (((((((.......)))))))..........................
DS A_GFP (siA)
                                                                (SEQ ID NO: 1)
5'-GGGAACCGUCCACUGGUUCCCGCUACGAGAGCCUGCCUCGUAGCUUCGGUGGUGCAGAUGAACUUCAGGGUCA

DS B_GFP (siB)
                                                                (SEQ ID NO: 2)
5'-GGGAACCGCAGGCUGGUUCCCGCUACGAGAGAACGCCUCGUAGCUUCGGUGGUGCAGAUGAACUUCAGGGUCA

DS C_GFP (siC)
                                                                (SEQ ID NO: 3)
5'-GGGAACCGCGUUCUGGUUCCCGCUACGAGACGUCUCCUCGUAGCUUCGGUGGUGCAGAUGAACUUCAGGGUCA

DS D_GFP (siD)
                                                                (SEQ ID NO: 4)
5'-GGGAACCGAGACGUGGUUCCCGCUACGAGUCGUGGUCUCGUAGCUUCGGUGGUGCAGAUGAACUUCAGGGUCA

DS E_GFP (siE)
                                                                (SEQ ID NO: 5)
5'-GGGAACCACCACGAGGUUCCCGCUACGAGAACCAUCCUCGUAGCUUCGGUGGUGCAGAUGAACUUCAGGGUCA

DS F_GFP (siF)
                                                                (SEQ ID NO: 6)
5'-GGGAACCGAUGGUUGGUUCCCGCUACGAGAGUGGACCUCGUAGCUUCGGUGGUGCAGAUGAACUUCAGGGUCA

Dicer substrate sense
                                                                (SEQ ID NO: 7)
5'-ACCCUGAAGUUCAUCUGCACCACCG
```

3' Malachite Green (MG) Aptamer[26, 27]
Modifications of RNA Rings

```
         (((((((......))))))) ((((((((.......))))))))..(((((..........((((....)))))...))))))
A-MG
                                                                                (SEQ ID NO: 8)
5'-GGGAACCGUCCACUGGUUCCCGCUACGAGAGCCUGCCUCGUAGCUUGACAUGGUAACGAAUGACAGUUCGCUGUCCGACAUGUC

B-MG
                                                                                (SEQ ID NO: 9)
5'-GGGAACCGCAGGCUGGUUCCCGCUACGAGAGAACGCCUCGUAGCUUGACAUGGUAACGAAUGACAGUUCGCUGUCCGACAUGUC

C -MG
                                                                               (SEQ ID NO: 10)
5'-GGGAACCGCGUUCUGGUUCCCGCUACGAGACGUCUCCUCGUAGCUUGACAUGGUAACGAAUGACAGUUCGCUGUCCGACAUGUC

D-MG
                                                                               (SEQ ID NO: 11)
5'-GGGAACCGAGACGUGGUUCCCGCUACGAGUCGUGGUCUCGUAGCUUGACAUGGUAACGAAUGACAGUUCGCUGUCCGACAUGUC

E-MG
                                                                               (SEQ ID NO: 12)
5'-GGGAACCACCACGAGGUUCCCGCUACGAGAACCAUCCUCGUAGCUUGACAUGGUAACGAAUGACAGUUCGCUGUCCGACAUGUC

F-MG
                                                                               (SEQ ID NO: 13)
5'-GGGAACCGAUGGUUGGUUCCCGCUACGAGAGUGGACCUCGUAGCUUGACAUGGUAACGAAUGACAGUUCGCUGUCCGACAUGUC
```

RNA Rings with Six Identical 3' Toeholds (3'
Side-Modified with Six Identical ssRNA Toeholds)

```
         (((((((((......))))))))) (((((((.......))))))))............
A_toehold (siA-t)
                                                              (SEQ ID NO: 14)
5'-GGGAAUCCGUCCACUGGAUUCCCGUCACAGAGCCUGCCUGUGACuucggugguqca B_toehold (siB-t)
                                                              (SEQ ID NO: 15)
5'-GGGAAUCCGCAGGCUGGAUUCCCGUCACAGAGAACGCCUGUGACuucggugguqca C_toehold (siC-t)
                                                              (SEQ ID NO: 16)
5'-GGGAAUCCGCGUUCUGGAUUCCCGUCACAGACGUCUCCUGUGACuucggugguqca D_toehold (siD-t)
                                                              (SEQ ID NO: 17)
5'-GGGAAUCCGAGACGUGGAUUCCCGUCACAGUCGUGGUCUGUGACuucggugguqca E_toehold (siE-t)
                                                              (SEQ ID NO: 18)
5'-GGGAAUCCACCACGAGGAUUCCCGUCACAGAACCAUCCUGUGACuucggugguqca F_toehold (siF-t)
                                                              (SEQ ID NO: 19)
5'-GGGAAUCCGAUGGUUGGAUUCCCGUCACAGAGUGGACCUGUGACuucggugguqca Dicer substrat sense for rings (DS sense) with toeholds
                                                              (SEQ ID NO: 20)
5'-ACCCUGAAGUUCAUCUGCACCACCGUGCACCACCG Dicer substrate antisense for rings with toeholds (DS antisense)
                                                              (SEQ ID NO: 21)
5'-CGGUGGUGCAGAUGAACUUCAGGGUCA
Toe-holds are underlined.
```

RNA Nanoring 3'-Side Functionalized with DS
Antisenses Against Six Different HIV-1[5]

The names of corresponding dicer substrates (DS) RNAs are indicated for each concatenated ring strand. Nanorings constructs contain a combination of six different DS RNAs that target the HIV-1 genome. Nanoring construct A targets: PBS-Matrix (PBS-MA), Envelope (gp120), Capsid (CA), Reverse Transcriptase (RT), Protease (PR) and Nef. Nanoring construct B targets: PBS-Matrix (PBS-MA), Capsid (CA), Reverse Transcriptase (RT), Protease (PR), Nef and Rev-Tat. Abbreviations: PBS, Primer Binding Site region; gp120, surface glycoprotein of 120KDa; Rev, Regulator of Expression Virion Proteins; Tat, Trans-Activator of Transcription; Nef, Negative Factor.

```
(((((((.......))))))) (((((((.......)))))))..........................
```
For nanoring A
DS A_PBS-Matrix
(SEQ ID NO: 22)
5'-GGGAAUCCGUCCACUGGAUUCCCGUCACAGAGCCUGCCUGUGACuugacggacucgcacccaucucucuccuu DS B_Envelope/gp120
(SEQ ID NO: 23)
5'-GGGAAUCCGCAGGCUGGAUUCCCGUCACAGAGAACGCCUGUGACuuggacaauuggagaagugaauuauauu DS C_Capsid
(SEQ ID NO: 24)
5'-GGGAAUCCGCGUUCUGGAUUCCCGUCACAGACGUCUCCUGUGACuuccuggaaugcugucaucauuucuucuu DS D_Reverse Transcriptase (SEQ ID NO: 25)
5'-GGGAAUCCGAGACGUGGAUUCCCGUCACAGUCGUGGUCUGUGACuuauuuaucuacuuguucauuuccucca DS E_Protease (SEQ ID NO: 26)
5'-GGGAAUCCACCACGAGGAUUCCCGUCACAGAACCAUCCUGUGACuuucuucuaauacuguaucaucugcuccu DS F_Nef (SEQ ID NO: 27)
5'-GGGAAUCCGAUGGUUGGAUUCCCGUCACAGAGUGGACCUGUGACuuggaggaaauuagocuuccagucccuu For nanoring B DS B_Rev-Tat (SEQ ID NO: 28)
5'-GGGAAUCCGCAGGCUGGAUUCCCGUCACAGAGAACGCCUGUGACuucgcugacuccgcuucuuccugccauuu Corresponding DS Senses(HIV-1)[5]

For nanoring A

DS PBS-Matrix (SEQ ID NO: 29)
5'-pGGAGAGAGAUGGGUGCGAGUUCGUC

DS Envelope/gp120

(SEQ ID NO: 30)
5'-pUAUAAUUCACUUCUCCAAUUGUCC

DS Capsid (SEQ ID NO: 31)
5'-pGA7GAA7UGAUGACAGCAUUUCAGG

DS Reverse Transcriptase (SEQ ID NO: 32)
5'-pGAGGAAAUGAACAAGUAGAUAAAU

-continued

DS Protease (SEQ ID NO: 33)
5'-pGAGCAGAUGAUACAGUAUUAGAAGA

DS Nef (SEQ ID NO: 34)
5'-pGGGACUGGAAGGGCUAAUUUUCUCC

For nanoring B

DS Rev-Tat (SEQ ID NO: 35)
5'-pAUGGCAGGAAGAAGCGGAGUUAGUG

RNA Nanorings 3'-Side Functionalized with DS Antisenses Against GSTP1-1

(These constructs were used as negative controls in HIV-1[29] experiments)

The names of corresponding siRNAs are indicated for each concatenated ring strand.

((((((((.......))))))))(((((((.......))))))).............................

DS A_GSTP1-1 (siA_ldr)

(SEQ ID NO: 36)
5'-GGGAAUCCGUCCACUGGAUUCCCGUCACAGAGCCUGCCUGUGACuugcagugccuucacauagucauccuugc DS B_GSTP1-1 (siB_r/t)

(SEQ ID NO: 37)
5'-GGGAAUCCGCAGGCUGGAUUCCCGUCACAGAGAACGCCUGUGACuugcagugccuucacauagucauccuugc DS C_GSTP1-1 (siC_gag)

(SEQ ID NO: 38)
5'-GGGAAUCCGCGUUCUGGAUUCCCGUCACAGACGUCUCCUGUGACuugcagugccuucacauagucauccuugc DS D_GSTP1-1 (siD_pol47)

(SEQ ID NO: 39)
5'-GGGAAUCCGAGACGUGGAUUCCCGUCACAGUCGUGGUCUGUGACuugcagugccuucacauagucauccuugc DS E_GSTP1-1 (siE_pol)

(SEQ ID NO: 40)
5'-GGGAAUCCACCACGAGGAUUCCCGUCACAGAACCAUCCUGUGACuugcagugccuucacauagucauccuugc

```
DS F_GSTP1-1 (siF_nef)
                                                  (SEQ ID NO: 41)
5'-GGGAAUCCGAUGGUUGGAUUCCCGUCACAGAGUGGACCUGUGACuugcagugccuucacauagucauccuugc DS sense
                                                  (SEQ ID NO: 42)
5'-pAAGGAUGACUAUGUGAAGGCACUGC
```

Corresponding Dicer Substrate RNA (HIV-1)[29] Sense Strands

```
1dr
                                                  (SEQ ID NO: 43)
5'-ggagagagaugggugcgaguucguc nef
                                                  (SEQ ID NO: 44)
5'-gggacuggaagggcuaauuuucucc pol
                                                  (SEQ ID NO: 45)
5'-acaggagcagaugauacaguuuuag r/t
                                                  (SEQ ID NO: 46)
5'-auggcaggaagaagcggaguuagug gag
                                                  (SEQ ID NO: 47)
5'-gaagaaaugaugacagcauuucagg pol47
                                                  (SEQ ID NO: 48)
5'-gugaaggggcaguaguaauuuaaga
```

DNA Sequences Designed for Auto-Recognizing RNA-DNA Hybrids Against eGFP[30]

```
DNA for sense_12
                                                  (SEQ ID NO: 49)
5'-GGAGACCGTGACCGGTGGTGCAGATGAACTTCAGGGTCA DNA for antisense_12
                                                  (SEQ ID NO: 50)
5'-TGACCCTGAAGTTCATCTGCACCACCGGTCACGGTCTCC
Auto-recognizing toe-holds are underlined.
```

Sense Strand (Underlined) Concatenated with J18 Aptamer Selected to Bind Epithelial Growth Factor Receptor (EGFR)[28]

Starting sequence (in lower case) required for high yields transcription with T7 RNA polymerase was removed post-transcriptionally using RNaseH.

```
J18_sense
                                                  (SEQ ID NO: 51)
5'gggaaaggaagagcGGCGCUCCGACCUUAGUCUCUGCAAGAUAAACC

GUGCUAUUGACCACCCUCAACACACUUAUUUAAUGUAUUGAACGGACCU

ACGAACCGUGUAGCACAGCAGAUUUGACCCUGAAGUUCAUCUGCACCAC

CG

DNA used for RNase H mediated degradation of
J18_sense starting sequence
                                                  (SEQ ID NO: 52)
5'-gctcttcctttccc
```

Fluorescently Labeled RNA Sequences

All fluorescently labeled RNA and DNA sequences were purchased from IDT.

Sense Strand of siRNA (DS RNA) Duplex Designed Against eGFP[25]

```
RNA sense Alexa 546 (for in vitro uptake studies)
                                                  (SEQ ID NO: 53)
5'-/5AlexF546N/ACCCUGAAGUUCAUCUGCACCACCG RNA sense_IRDye700 (for in vivo studies)
                                                  (SEQ ID NO: 54)
5'-/5IRD700/ACCCUGAAGUUCAUCUGCACCACCG
```

Fluorescently Labeled DNA Sequences Designed for Auto-Recognizing R/DNA Hybrid Experiments

```
DNA for sense Alexa488
                                                  (SEQ ID NO: 55)
5'-GGAGACCGTGACCGGTGGTGCAGATGAACTTCAGGGTCAtt/
3AlexF488N/

DNA for antisense Alexa546
                                                  (SEQ ID NO: 56)
5'-/5AlexF546N/aaTGACCCTGAAGTTCATCTGCACCACCGGTCAC
GGTCTCC
```

Fluorescently Labeled DNAs Designed for Visualization

```
DNA-sense-Alexa546 (for in vitro transfection
experiments)
                                                  (SEQ ID NO: 57)
5'-/5AlexF546N/aaTGACCCTGAAGTTCATCTGCACCACCG DNA-sense-IRDye700 (for in vivo experiments)
                                                  (SEQ ID NO: 58)
5'-/5IRD700/ACCCTGAAGTTCATCTGCACCACCG
```

Biotinilated DNAs

```
DNA-sense-Biotin
                                                  (SEQ ID NO: 59)
5'/5Biosg/aaTGACCCTGAAGTTCATCTGCACCACCG
```

DNA Sequences Designed for Auto-Recognizing RNA-DNA Hybrids Against eGFP[7]

```
DNA for sense (12 nts toehold)
                                                  (SEQ ID NO: 49)
5'-GGAGACCGTGACCGGTGGTGCAGATGAACTTCAGGGTCA
```

```
                                    -continued
       DNA for antisense (12 nts toehold)
                                                 (SEQ ID NO: 50)
       5'-TGACCCTGAAGTTCATCTGCACCACCGGTCACGGTCTCC
       Auto-recognizing toe-holds are underlined.
```

RNA molecules were purchased (from Integrated DNA Technologies, Inc., for short RNAs, e.g., siRNAs and/or DsiRNAs) or prepared by transcription of PCR amplified DNA templates; synthetic DNA molecules coding for the sequence of the designed RNA were purchased already amplified by PCR using primers containing the T7 RNA polymerase promoter (see PCT/US2013/058492, filed Sep. 6, 2013, incorporated by reference in its entirety herein). PCR products were purified using the QiaQuick PCR purification kit and RNA molecules were prepared enzymatically by in vitro transcription using T7 RNA polymerase. For the visualization of assembled RNA NPs quality control experiments, [$^{32}$P]Cp labeled RNA molecules were used (T4 RNA ligase is used to label the 3'-ends of RNA molecules by attaching [$^{32}$P]Cp[19]). In the case of the initial radiolabel native-PAGE assays, radiolabeled RNA scaffold strand was mixed with concatenated strands individually followed by the assembly protocol[4]. For dicing functional control experiments, RNA molecules were co-transcriptionally α[P$^{32}$]-ATP body-labeled. Native PAGE experiments were performed as described[20]. Typically, assembly experiments reported were analyzed at 10° C. on 7% (29:1) native polyacrylamide gels in the presence of 89 mM Tris-borate, pH 8.3, 2 mM Mg(OAc)$_2$. A Hitachi FMBIO II Multi-View Imager was used to visualize SYBR Gold stained R/DNA hybrids.

Dynamic Light Scattering (DLS) Experiments.

For DLS, 10 μl of sample solution containing preassembled nanorings with six DS RNAs were measured by DynaPro99 (Protein Solution/Wyatt) with a laser wavelength of 824 nm at 24° C.[11]. The theoretical hydrodynamic radii ($R_h$) were calculated by measuring three-dimensional CPK models.

Recombinant Human Dicer Assay.

Nanorings with six DS RNAs were prepared as described above to a final concentration of 3 μM. For dicing experiments, samples were incubated for 4 hours at 37° C. with recombinant human turbo dicer enzyme kit (Genlantis), containing an ultra-active form of human recombinant dicer enzyme, according to the manufacturer's suggested protocol[5]. Dicing reactions were quenched by adding dicer stop solution (provided by the manufacturer) prior to analysis on 2 mM Mg(OAc)$_2$ native 7% PAGE (described above).

Malachite Green (MG) Aptamers Fluorescent Experiments.

All fluorescent studies of MG aptamer functionalized nanorings (at 1 μM final) were carried out in assembly buffer during the incubation at 37° C. For all samples, the excitation was set at 425 nm. For co-transcriptional assemblies of RNA nanorings functionalized with up to six MG aptamers, aliquots of transcription mixture were taken, MG was added (10 μM final) to each aliquot, and the emission was measured promptly. Some bleaching of MG by transcription mixture was observed over time.

Cryogenic Electron Microscopy (Cryo-EM) Experiments.

Quantifoil Copper 200 mesh R 3.5/1 grids were washed overnight with acetone. To prepare a frozen, hydrated grid, 2.5 μL of sample was applied to the grid, blotted, and plunged into liquid ethane using Vitrobot III (FEI, Hillsboro, Oreg.). Images were collected at liquid nitrogen temperature (~100 K) on a JEM-2200FS (JEOL Inc., Tokyo, Japan) transmission electron cryo-microscope equipped with a field emission gun (FEG) and an energy filter and JEM-2010F equipped with an FEG (incolumn energy filter). JEM-2200FS and JEM-2010F were operating at 200 kV and were equipped with a Gatan cryo-holder (model 626) (Gatan Inc., Pleasanton, Calif.). Images were recorded on a 4 k by 4 k CCD camera (Gatan Inc., Pleasanton, Calif.). Samples were imaged at 83555× effective magnification targeted at 2-5 μm underfocus. A total specimen exposure for each image of 33 e$^-$/Å$^2$ sec was used.

Cryogenic Electron Microscopy (Cryo-EM) Reconstruction.

RNA particles were boxed using EMAN2 boxer. 3D reconstruction was carried out with the EMAN2 software[21], employing the e2refine2d.py iterative reference free alignment[22] algorithm based on multivariate statistical analysis implemented in EMAN2. Six-fold symmetry was imposed for structure determination. The resolution of the map was assessed to be 16 A using the goldstandard criterion of Fourier Shell Correlation (FSC) cutoff at 0.143 from two independent halfsets of data (Scheres and Chen. *Nat Methods* 2012, 9, 853-4). The map was deposited to EMDB.

Hexameric Nanoring Models.

Models of hexameric nanorings with six DS siRNA arms were created by merging the model of the hexameric ring scaffold, built with the aid of our program NanoTiler (http://www-lecb.ncifcrf.gov/~bshapiro/software.html; Bindewald et al. *J Mol Graph Model* 2008, 27, 299-308) with several alternative models of one monomer with the siRNA arm. Monomer models were built with the aid of programs RNA2D3D (http://www-lecb.ncifcrf.gov/~bshapiro/software.html; Martinez et al. *J Biomol Struct Dyn* 2008, 25, 669-83), MCSym (http://www.major.iric.ca/MC-Pipeline/; Parisien and Major. *Nature* 2008, 452, (7183), 51-5) and RNAComposer (http://euterpe.man.poznan.pl/Home; Popenda et al. *Nucleic Acids Res* 2012, 40, e112). All three programs take sequence and secondary structure descriptors as input and output 3D structures (PDB format files). From among multiple models generated by the programs, several representatives were selected based on the combination of the best (lowest) free energy, best structural fit of the 3D structures to the hexameric ring, performed with the aid of the PyMOL Molecular Graphics System (using custom scripts) (Schrodinger, LLC., http://www.pymol.org/). Models were also selected to represent potential alternative orientations of the siRNA arms relative to the plain of the nanoring. All models were subjected to GBSA-based energy minimization (implicit solvent method) in Amber12 with the RNA force field ff10 (Case et al. AMBER12. In University of California: San Francisco, 2012; Essmann et al. *J Chem Phys* 1995, 103, 8577-93; Wang et al. *J Comput Chem* 2000, 21, 1049-74) and thus structurally refined.

Fitting Hexameric Nanoring Models to the Cryo-EM Density Map.

Finally, given the cryo-EM reconstruction, the UCSF Chimera package (http://www.cgl.ucsf.edu/chimera; Pettersen et al. J Comput Chem 2004, 25, 1605-12) was used to best fit models in the density volume. The fit shown in FIG. 2*b* had the volume map thresholded at the minimum level at which all the atoms of the model can be fit inside the volume (or maximum density level accommodating all the atoms of the model).

Transfection Experiments.

For assaying the delivery of functionalized nanorings, human breast cancer cell line MDA-MB-231 (with or without eGFP) was grown in D-MEM media (Gibco BRL) supplemented with 10% FBS and penicillin-streptomycin in a 5% CO2 incubator. All in vitro transfections in this project were performed using Lipofectamine 2000 (L2K) purchased from Invitrogen. 10× or 50× solutions of R/DNA hybrids were preincubated at 30° C. with L2K. For all transfections (unless indicated otherwise), the concentration of DS RNAs was six times higher compared to nanorings functionalized with six DS RNAs. Prior to each transfection, the cell media was swapped with OPTI-MEM and prepared 10× or 50×RNA/L2K complex was added to the final concentration of 1×. The cells were incubated for 4 hours followed by the media change (D-MEM, 10% FCS, 1% pen-strep).

For targeting experiments, A431 cells were washed three times in DPBS/5 mM $MgCl_2$ and $2\times10^5$ cells were incubated in the presence of ~170 nM (final concentration) of nanoring RNA particles in the dark for 30 min at room temperature. Subsequently, cells were washed three times with DPBS 5 mM $MgCl_2$ and 10 000 cells were analyzed using a BD FACSCanto™ II (BD Bioscience) flow cytometer. Data were analyzed using FlowJo_V10 software. RiboShredder™ RNAse blend (Epicentre, Madison, Wis.) was added at a final concentration~0.03 U/μL and cells were kept on ice to prevent endosomal uptake of bound NPs. The final concentration of the rEGF (GenScript, Piscataway, N.J.) and rIgG proteins (ACRObiosystems, Bethesda, Md.) were 500 nM and 150 nM, respectively.

Microscopy.

To assess the delivery of functionalized nanorings in cells, measurements were performed using a LSM 710 confocal microscope (Carl Zeiss) with a 63×, 1.4 NA magnification lens. MDA-MB-231 cells were plated in glass bottom petri dishes (Ibidi, Germany) and subjected to transfection with nanorings as described above. Images of the cells were then taken to assess the appearance of FRET within the sample. For Alexa546 imaging, a DPSS 561 laser was used for excitation and emission was collected between 566 and 680 nm. All images were taken with a pinhole adjusted to 1 airy unit.

Endosomal Co-Localization Studies.

To confirm the endosomal location of endocytosed fluorescently labeled functional RNA nanorings in cells, co-staining experiments with endosomal markers (EEA1 and Rab7) were performed (Afonin et al. *Nat Nanotechnol* 2013, 8, (4), 296-304). Cells were transfected with RNA NPs labeled with six Alexa546 dyes. On the next day, transfected cells were fixed with 4% paraformaldehyde for 20 minutes at room temperature and handled at this temperature thereafter. Samples were washed three times with PBS and then permeabilized with 0.2% Triton X-100 for 20 minutes. Upon washing three times with PBS, samples were blocked for one hour with 1% BSA and then exposed to primary antibodies against the early endosome associated protein EEA1 (Cell signaling) or against the late endosome marker Rab7 (Cell signaling). Upon washing three times with PBS, the samples were stained with a secondary Alexa 488 antibody (Molecular Probes). As the comparison, fluorescently labeled DS RNAs were used at six fold higher concentrations.

Re-Association of RNA-DNA Hybrids in Cells Assessed Through FRET (Afonin et al. *Nat Nanotechnol* 2013, 8, (4), 296-304). All measurements were performed using a LSM 710 confocal microscope (Carl Zeiss) with a 63×, 1.4 NA magnification lens. All images were taken with a pinhole adjusted to 1 airy unit. Fluorescently labeled hybrid NPs and cognate hybrids were individually preincubated with L2K and cotransfected into cells. On the next day, the samples were fixed by incubation in 4% paraformaldehyde for 20 minutes at room temperature. Images of the cells were then taken to assess the appearance of FRET within the sample. For Alexa 488 imaging, the 488 nm line of an Argon laser was used as excitation and the emission was collected between 493 and 557 nm. For Alexa 546 imaging, a DPSS 561 laser was used for excitation and emission was collected between 566 and 680 nm. In order to evaluate the sensitized emission through FRET, images were taken exciting the sample with the 488 nm line and collecting emission between 566 and 680 nm. Because of spectral overlap, the FRET signal is contaminated by donor emission into the acceptor channel and by the excitation of acceptor molecules by the donor excitation wavelength. This bleed through was assessed through measurements performed with samples transfected with individual dyes and mathematically removed from the images of FRET.

Flow Cytometry Experiments.

For statistical analysis with flow cytometry experiments, the MDA-MB-231 231 (with or without eGFP) cells grown in 12-well plates ($10\times10^4$ cells per well) were lifted with cell dissociation buffer, washed twice with PBS and the level of expression of eGFP was determined by fluorescence-activated cell sorting (FACS) analysis on a FACScalibur flow cytometer (BD Bioscience). At least 30,000 events were collected and analyzed using the Cell quest software.

In Vivo Experiments.

Animal studies were performed according to the Frederick National Laboratory for Cancer Research (Frederick, Md.) Animal Care and Use Committee guidelines. Imaging studies were performed on MDA-MB-231 tumor bearing athymic nude mice (Charles River Laboratories, Frederick, Md.). For tumor induction, a single cancer cell suspension of MDA-MB-231/GFP human breast cancer cell line expressing GFP was prepared in Hanks Balanced Salt Solution (HBSS). 7-9 week old female athymic nude mice were subcutaneously implanted with $1\times10^7$ cancer cells in 100 μL HBSS in the mouse flank. For in vivo delivery, DS RNAs and functional nanorings were associated with bolaamphiphilic (bolas) cationic carriers as described in Kim et al. *Mol Ther Nucleic Acids* 2013, 2, e80. After sufficient growth of soft tumors (~1 week), two mice were injected intra-tumorally with DS RNAs (300 nM RNA and 10 μg/ml bola in 100 μl of the PBS injection mixture), and two mice were injected with nanorings functionalized with six DS RNAs (50 nM RNA and 10 μg/ml bola in 100 μl of the PBS injection mixture). One control mouse was injected with 100 μl 1×PBS buffer. After five days (120 hours), mice were sacrificed. Tumors were removed from mice, fixed overnight at 4° C. in 4% PFA, then transferred to 20% sucrose overnight at 4° C. Excess sucrose was blotted from the tumor, and the tumor was embedded in OCT Compound (Tissue-Tek). 10 μm cryosections were mounted on slides and stained with DAPI (Invitrogen) then coverslipped with Prolong Gold a/Fade reagent (Invitrogen). Images were captured using Nikon's Eclipse 80i microscope, with a QImaging Retiga-2000R camera and Nikon's NIS-Elements AR Imaging Software. The data was quantified and presented based on the total GFP signal normalized to the total number of cells in the given field. For bio-distribution experiments: after sufficient growth of injected MDA-MB-231 (no eGFP) tumors (~2 weeks), two mice were injected in the tail vein with siRNA_IRDye700 and nanorings_IRDye700 associated with bolaamphiphilic cationic carriers (described elsewhere[23]) and one control mouse was injected with 1×PBS buffer. Fluorescence imaging (Maestro GNIR-FLEX, Cambridge Research & Instrumentation, Inc. Woburn, Mass.) was performed at baseline (pre-injection for determining auto-fluorescence), and 10 min, 20 min, 30 min, 45 min, 1 hr and 2 hrs and 3 hrs post injection while the animal was anesthetized (1-2% isoflurane in $O_2$ at 1 L/min flow). The animal's internal temperature was maintained prior, during the scan (heated imaging table), and post imaging while the animal recovered from anesthesia. Image analysis (image library for auto-fluorescence and contrast agent) was performed according to manufacturer's protocol (Maestro software 2.10.0, CRi, Woburn, Mass.). Due to the IR wavelength parameters of the contrast agent, image acquisition utilized an excitation filter (590±15 nm), emission filter (645 nm long pass) and a multispectral acquisition of 650-850 nm with 10 nm steps. Regions of interests were drawn around different organs and the total signal (counts/s) recovered for the different time points. The signal was then normalized by the weight of the different organs. After the 3 hrs post injection time-point, mice were euthanized ($CO_2$ asphyxiation as per ACUC guideline) to measure pertinent organ (spleen, lung, brain, liver, kidney, intestines, heart, tumor, and bladder) weights and uptake implementing the in vivo imaging acquisition parameters. For silencing experiments: after sufficient growth of injected MDA-MB-231/eGFP tumors (~1 week), two mice were injected intratumorally with siRNA and nanorings with six siRNAs associated with bolaamphiphilic cationic carriers (described elsewhere) and one control mouse was injected with 1×PBS buffer. After five days (120 hours), mice were sacrificed. Tumors were removed from mice, fixed overnight at 4° C. in 4% PFA, then transferred to 20% sucrose overnight at 4° C. Excess sucrose was blotted from the tumor, and the tumor was embedded in OCT Compound (Tissue-Tek). 10 μm cryosections were mounted on slides and stained with DAPI (Invitrogen) then coverslipped with Prolong Gold a/Fade reagent (Invitrogen). Images were captured using Nikon's Eclipse 80i microscope, with a QImaging Retiga-2000R camera and Nikon's NIS-Elements AR Imaging Software.

Cell Viability Assay.

Cells were seeded in 96 well plates at a density of 10,000 cells/well in serum containing media 24 hours prior to experiments. Samples were added to the cells in triplicate in serum free media and incubated for 4 hours at 37° C. After incubation the serum free media was replaced with serum containing media. At different time points, according to the manufacturer's protocol, cell titer blue reagent was added to each well and the cells were further incubated for 3 hours at 37° C. The fluorescence of the resofurin (converted from resazurin by viable cells) was measured at $\lambda$ex 560 nm and $\lambda$em 590 nm with an auto cut-off in a fluorescent ELISA plate reader (SpectraMAX, Molecular Devices, Sunnyvale, Calif.).

HIV-1 Inhibition by Functional Nanorings.

To test inhibition of HIV-1 gene expression mediated by nanorings functionalized with six dicer substrates (DS) RNAs were selected against multiple regions of the HIV-1 genome. After cleavage by dicer inside cells, these siRNAs were able to knock down HIV-1 gene expression and virus particle production. Nanoring A targeted the HIV-1 genome at: primer-binding site (PBS)-Matrix (PBS-MA), Capsid (CA), Protease (PR), Reverse Transcriptase (RT), surface envelope glycoprotein (gp120), and Nef. Nanoring construct B targeted the HIV-1 genome at: PBS-Matrix (PBS-MA), Capsid (CA), Protease (PR), Reverse Transcriptase (RT), Nef and Rev-Tat. Rev stands for Regulator of Expression Virion Proteins. Tat stands for Trans-Activator of Transcription and Nef stands for Negative Factor. To validate the knockdown of the nanorings constructs A and B, a corresponding mixture of individual DS RNAs was used. As a negative control, a nanoring containing six copies of DS RNAs against the cellular protein GSTP1 was used (Afonin et al. *Nat Nanotechnol* 2013, 8, (4), 296-304; Afonin et al. *Acc Chem Res* 2014). Hela cells were co-transfected with the WT HIV-1 molecular clone, pNL4-3, psiCHECK™-1 (*Renilla* Luciferase expression vector, Promega), and the functional nanorings or DS mixtures using Lipofectamine 2000 (Invitrogen). At 48 hours post-transfection, the supernatants were harvested and the reverse transcriptase (RT) activity was measured in an in vitro reaction (Freed and Martin. *J Virol* 1994, 68, (4), 2503-12). Levels of RT activity were directly proportional to the amount of released virus. Viral protein expression was analyzed by western blotting. Cells were lysed using 1× *Renilla* Lysis Buffer (Promega) according to manufacture's protocol. Protein samples were separated by SDS-PAGE and transferred to a polyvinylidene fluoride (PVDF) membrane (Immobilon, Millipore) by semi-dry electroblotting. Membranes were probed with primary antibody (pooled immunoglobulin from HIV-1-infected patients, HIV-Ig; NIH AIDS Research and Reference Reagent Program) overnight at 4° C., washed, then incubated for 1 h with human specific horseradish peroxidase-conjugated secondary antibody. Membranes were then incubated with SuperSignal West Pico Chemiluminescent Substrate (Thermo Scientific). After incubation at room temperature, membranes were exposed to a charge-coupled device in a Universal Hood II (Biorad). Quantification was performed using ImageLab software (Biorad). Total HIV-1 Gag protein was measured (55 kDa Gag precursor+matrix/capsid p41+capsid, capsid/SP1 p24/p25) and values were normalized to virus control (no siRNA co-transfected with pNL4-3). No signal was detected in untransfected cells lysates (data not shown). N=4.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

The following specific references, also incorporated by reference, are indicated above by corresponding reference number.

1. Li, N. et al. Technical and biological issues relevant to cell typing with aptamers. J Proteome Res 8, 2438-2448 (2009).
2. Li, N., Larson, T., Nguyen, H. H., Sokolov, K. V. & Ellington, A. D. Directed evolution of gold nanoparticle delivery to cells. Chemical communications (Cambridge, England) 46, 392-394 (2010).
3. Li, N., Nguyen, H. H., Byrom, M. & Ellington, A. D. Inhibition of cell proliferation by an anti-EGFR aptamer. PloS one 6, e20299 (2011).
4. Afonin, K. A. et al. Design and self-assembly of siRNA-functionalized RNA nanoparticles for use in automated nanomedicine. Nat Protoc 6, 2022-2034 (2011).
5. Grabow, W. W. et al. Self-assembling RNA nanorings based on RNAI/II inverse kissing complexes. Nano Lett 11, 878-887 (2011).
6. Rose, S. D. et al. Functional polarity is introduced by Dicer processing of short substrate RNAs. Nucleic Acids Res 33, 4140-4156 (2005).
7. Afonin, K. A., Danilov, E. O., Novikova, I. V. & Leontis, N. B. TokenRNA: a new type of sequence-specific, label-free fluorescent biosensor for folded RNA molecules. Chembiochem 9, 1902-1905 (2008).
8. Grate, D. & Wilson, C. Laser-mediated, site-specific inactivation of RNA transcripts. Proc Natl Acad Sci USA 96, 6131-6136 (1999).
9. Kolpashchikov, D. M. Binary malachite green aptamer for fluorescent detection of nucleic acids. J Am Chem Soc 127, 12442-12443 (2005).
10. Stojanovic, M. N. & Kolpashchikov, D. M. Modular aptameric sensors. J Am Chem Soc 126, 9266-9270 (2004).
11. Afonin, K. A. et al. In vitro assembly of cubic RNA-based scaffolds designed in silico. Nat Nanotechnol 5, 676-682 (2010).
12. Afonin, K. A. et al. Activation of different split functionalities on re-association of RNA-DNA hybrids. Nat Nanotechnol 8, 296-304 (2013).
13. Shu, D., Shu, Y., Haque, F., Abdelmawla, S. & Guo, P. Thermodynamically stable RNA three-way junction for constructing multifunctional nanoparticles for delivery of therapeutics. Nat Nanotechnol 6, 658-667 (2011).
14. Chang, C. I. et al. Enhanced intracellular delivery and multi-target gene silencing triggered by tripodal RNA structures. J Gene Med 14, 138-146 (2012).
15. Lee, Y. S. et al. Silencing by small RNAs is linked to endosomal trafficking. Nat Cell Biol 11, 1150-1156 (2009).
16. Sen, G. L. & Blau, H. M. Argonaute 2/RISC resides in sites of mammalian mRNA decay known as cytoplasmic bodies. Nat Cell Biol 7, 633-636 (2005).
17. Nakashima, Y., Abe, H., Abe, N., Aikawa, K. & Ito, Y. Branched RNA nanostructures for RNA interference. Chemical communications (Cambridge, England) (2011).
18. Zhang, H., Kolb, F. A., Brondani, V., Billy, E. & Filipowicz, W. Human Dicer preferentially cleaves dsRNAs at their termini without a requirement for ATP. Embo J 21, 5875-5885 (2002).
19. Afonin, K. A., Cieply, D. J. & Leontis, N. B. Specific RNA self-assembly with minimal paranemic motifs. J Am Chem Soc 130, 93-102 (2008).
20. Afonin, K. A. & Leontis, N. B. Generating new specific RNA interaction interfaces using C-loops. J Am Chem Soc 128, 16131-16137 (2006).
21. Tang, G. et al. EMAN2: an extensible image processing suite for electron microscopy. Journal of structural biology 157, 38-46 (2007).
22. Wakabayashi, H., Varfaj, F., Deangelis, J. & Fay, P. J. Generation of enhanced stability factor VIII variants by replacement of charged residues at the A2 domain interface. Blood 112, 2761-2769 (2008).
23. Kim, T. et al. In Silico, In Vitro, and In Vivo Studies Indicate the Potential Use of Bolaamphiphiles for Therapeutic siRNAs Delivery. Mol Ther Nucleic Acids 2, e80 (2013).
24. Afonin, K. A. et al. Design and self-assembly of siRNA-functionalized RNA nanoparticles for use in automated nanomedicine. Nat Protoc 6, 2022-2034 (2011).
25. Rose, S. D. et al. Functional polarity is introduced by Dicer processing of short substrate RNAs. Nucleic acids research 33, 4140-4156 (2005).
26. Afonin, K. A., Danilov, E. O., Novikova, I. V. & Leontis, N. B. TokenRNA: a new type of sequence-specific, label-free fluorescent biosensor for folded RNA molecules. Chembiochem 9, 1902-1905 (2008).
27. Grate, D. & Wilson, C. Laser-mediated, site-specific inactivation of RNA transcripts. Proceedings of the National Academy of Sciences of the United States of America 96, 6131-6136 (1999).
28. Li, N. et al. Technical and biological issues relevant to cell typing with aptamers. Journal of proteome research 8, 2438-2448 (2009).
29. Low, J. T. et al. SHAPE-directed discovery of potent shRNA inhibitors of HIV-1. Mol Ther 20, 820-828 (2012).
30. Afonin, K. A. et al. Activation of different split functionalities on re-association of RNA-DNA hybrids. Nat Nanotechnol 8, 296-304.
31. Shapiro B et al. Protocols for the In silico Design of RNA Nanostructures. In: Nanostructure Design Methods and Protocols. Totowa, N.J.: Humana Press; 2008. p. 93-115 [Book Chapter]
32. Bindewald et al. Computational strategies for the automated design of RNA nanoscale structures from building blocks using NanoTiler. Mol. Graph. Model. 27(3): 299-308, 2008.
33. Shapiro B A et al. Protocols for the in silico design of RNA nanostructures. Methods Mol. Biol. 474: 93-115, 2008.
34. Martinez H M et al. RNA2D3D: A program for Generating, Viewing, and Comparing 3-Dimensional Models of RNA. J. Biomol. Struct. Dyn. 25: 669-83, 2008. [Journal]
35. Bindewald E et al. RNAJunction: a database of RNA junctions and kissing loops for three-dimensional structural analysis and nanodesign. Nucleic Acids Res. 36: D392-7, 2008.
36. Yingling Y G et al. Computational Design of an RNA Hexagonal Nanoring and an RNA Nanotube. Nano Lett. 7(8): 2328-2334, 2007. Full Text Article.
37. Hastings W et al. Structural and dynamical classification of RNA single-base bulges for nanostructure design. J. Comp. Theor. Nanoscience. 3: 63-77, 2006.
38. Paliy M et al. Molecular dynamics study of the RNA ring nanostructure: a phenomenon of self-stabilization. Phys Biol. 6(4): 46003, 2009.

What is claimed is:

1. An RNA nanoparticle (RNA NP) or R/DNA chimeric nanoparticle (R/DNA NP) comprising a nanoring comprising one or more functionalities attached by way of toehold interactions wherein each toehold interaction comprises a single strand nucleation site on the nanoring that hybridizes to a complementary single strand nucleic acid on each of the one or more functionalities and wherein the one or more functionalities are inhibitory nucleic acids, fluorescent dyes, small molecules, RNA-DNA hybrids with split functionalities, split lipase, split GFP, proteins, targeting moieties, therapeutic agents, or imaging agents.

2. The RNA NP or R/DNA NP of claim 1, wherein the one or more functionalities comprise one or more RNA-DNA hybrid arm extensions or one or more double strand RNA arm extensions, or a combination thereof attached to the nanoring by way of the toehold interactions.

3. The RNA NP or R/DNA NP of claim 2, wherein one or more of said RNA-DNA hybrid arm extensions is capable of triggered release, formation and/or activation of a inhibitory nucleic acid.

4. The RNA NP or R/DNA NP nanoparticle of claim 1, wherein the inhibitory nucleic acids are selected from the group consisting of: siRNAs, RNA or DNA aptamers and ribozymes.

5. The RNA NP or R/DNA NP of claim 1, wherein the one or more functionalities are the same.

6. The RNA NP or R/DNA NP of claim 1, wherein the one or more functionalities are different.

7. The RNA NP or R/DNA NP of claim 3, wherein the RNA NP or R/DNA NP is capable of triggered release, formation and/or activation of an inhibitory nucleic acid in the presence of a second and complementary chimeric nanoparticle-s.

8. The RNA NP or R/DNA NP of claim 7, wherein the second chimeric nanoparticle comprises a second RNA-DNA hybrid whose sequences are complementary to the RNA-DNA hybrid arm extension of the nanoring.

9. The RNA NP or R/DNA NP of claim 8, wherein the RNA-DNA hybrid arm extensions of the nanoring and the complementary RNA-DNA hybrid each comprise an additional complementary DNA toehold sequence which facilitates the reassociation and formation of an active siRNA from the complementary RNA sequences.

10. The R/DNA NP of claim 9, wherein the siRNA inhibits a target RNA.

11. The RNA NP or R/DNA NP of claim 10, wherein the target RNA encodes an apoptosis inhibitor protein.

12. The RNA NP or R/DNA NP of claim 10, wherein the target RNA is a pathogenic RNA genome, an RNA transcript derived from the genome of the pathogenic agent, or a portion thereof.

13. The RNA NP or R/DNA NP of claim 12, wherein the pathogenic agent is a virus, a bacteria, a fungus, or a parasite.

14. The RNA NP or R/DNA chimeric polyfunctional nanoparticles of claim 10, wherein the target RNA is a viral RNA genome or a portion thereof.

15. A pharmaceutical composition comprising an RNA NP or R/DNA NP of claim 1.

16. The pharmaceutical composition of claim 15, further comprising a pharmaceutically acceptable excipient, carrier, or diluent.

17. A kit comprising the RNA NP or R/DNA NP of claim 1 and a set of instructions.

18. The RNA NP or R/DNA NP of claim 10, wherein the target RNA is one or more HIV-1 transcripts.

19. The RNA NP or R/DNA NP of claim 18, wherein the one or more HIV-1 transcripts are selected from the group consisting of transcripts encoding: PBS-matrix; capsid; protease; reverse transcriptase; envelope; Nef; and Rev-Tat.

* * * * *

SEQUENCE LISTING

<160> NUMBER OF SEQ ID NOS: 59

<210> SEQ ID NO 1
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide <400> SEQUENCE: 1
gggaaccguc cacugguucc cgcuacgaga gccugccucg uagcuucggu ggugcagaug      60
aacuucaggg uca                                                        73

<210> SEQ ID NO 2
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide <400> SEQUENCE: 2
gggaaccgca ggcugguucc cgcuacgaga gaacgccucg uagcuucggu ggugcagaug      60
aacuucaggg uca                                                        73

<210> SEQ ID NO 3
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide <400> SEQUENCE: 3
gggaaccgcg uucugguucc cgcuacgaga cgucccucg uagcuucggu ggugcagaug       60
aacuucaggg uca                                                        73

<210> SEQ ID NO 4
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide <400> SEQUENCE: 4
gggaaccgag acugguuucc cgcuacgagu cguggucucg uagcuucggu ggugcagaug      60
aacuucaggg uca                                                        73

<210> SEQ ID NO 5
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide <400> SEQUENCE: 5
gggaaccacc acgagguucc cgcuacgaga accauccucg uagcuucggu ggugcagaug      60
aacuucaggg uca                                                        73

```
<210> SEQ ID NO 6
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggaaccgau gguugguucc cgcuacgaga guggaccucg uagcuucggu ggugcagaug    60
aacuucaggg uca                                                      73

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
acccugaagu ucaucugcac caccg                                         25

<210> SEQ ID NO 8
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggaaccguc cacugguucc cgcuacgaga gccugccucg uagcuugaca ugguaacgaa    60
ugacaguucg cuguccgaca uguc                                          84

<210> SEQ ID NO 9
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggaaccgca ggcugguucc cgcuacgaga gaacgccucg uagcuugaca ugguaacgaa    60
ugacaguucg cuguccgaca uguc                                          84

<210> SEQ ID NO 10
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaaccgcg uucugguucc cgcuacgaga cgucccucg uagcuugaca ugguaacgaa     60
ugacaguucg cuguccgaca uguc                                          84

<210> SEQ ID NO 11
<211> LENGTH: 84
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
gggaaccgag acgugguucc cgcuacgagu cguggucucg uagcuugaca ugguaacgaa    60
ugacaguucg cguccgaca uguc                                            84

<210> SEQ ID NO 12
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaaccacc acgagguucc cgcuacgaga accauccucg uagcuugaca ugguaacgaa    60
ugacaguucg cguccgaca uguc                                            84

<210> SEQ ID NO 13
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gggaaccgau gguugguucc cgcuacgaga guggaccucg uagcuugaca ugguaacgaa    60
ugacaguucg cguccgaca uguc                                            84

<210> SEQ ID NO 14
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaauccgu ccacuggauu cccgucacag agccugccug ugacuucggu ggugca         56

<210> SEQ ID NO 15
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gggaauccgc aggcuggauu cccgucacag agaacgccug ugacuucggu ggugca         56

<210> SEQ ID NO 16
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gggaauccgc guucuggauu cccgucacag acgucccug ugacuucggu ggugca          56
```

```
<210> SEQ ID NO 17
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gggaauccga gacguggauu cccgucacag ucguggucug ugacuucggu ggugca        56

<210> SEQ ID NO 18
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggaauccac cacgaggauu cccgucacag aaccauccug ugacuucggu ggugca        56

<210> SEQ ID NO 19
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gggaauccga ugguuggauu cccgucacag aguggaccug ugacuucggu ggugca        56

<210> SEQ ID NO 20
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
acccugaagu ucaucugcac caccgugcac caccg                               35

<210> SEQ ID NO 21
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cgguggugca gaugaacuuc aggguca                                        27

<210> SEQ ID NO 22
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gggaauccgu ccacuggauu cccgucacag agccugccug ugacuugacg gacucgcacc    60
caucucucuc cuu                                                       73
```

```
<210> SEQ ID NO 23
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gggaauccgc aggcuggauu cccgucacag agaacgccug ugacuuggac aauuggagaa    60
gugaauuaua uu                                                        72

<210> SEQ ID NO 24
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gggaauccgc guucuggauu cccgucacag acgucccug ugacuuccug gaaugcuguc     60
aucauuucuu cuu                                                       73

<210> SEQ ID NO 25
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggaauccga gacguggauu cccgucacag ucguggucug ugacuuauuu aucuacuugu    60
ucauuuccuc ca                                                        72

<210> SEQ ID NO 26
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaauccac cacgaggauu cccgucacag aaccauccug ugacuuucuu cuaauacugu    60
aucaucugcu ccu                                                       73

<210> SEQ ID NO 27
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gggaauccga ugguuggauu cccgucacag aguggaccug ugacuuggag gaaauuagcc    60
cuuccagucc cuu                                                       73

<210> SEQ ID NO 28
<211> LENGTH: 73
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 28
gggaauccgc aggcuggauu cccgucacag agaacgccug ugacuucgcu gacuccgcuu    60
cuuccugcca uuu    73

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ggagagagau gggugcgagu ucguc    25

<210> SEQ ID NO 30
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uauaauucac uucuccaauu gucc    24

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gaagaaauga ugacagcauu ucagg    25

<210> SEQ ID NO 32
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gaggaaauga acaaguagau aaau    24

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gagcagauga uacaguauua gaaga    25

```
<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gggacuggaa gggcuaauuu ucucc                                              25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
auggcaggaa gaagcggagu uagug                                              25

<210> SEQ ID NO 36
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gggaauccgu ccacuggauu cccgucacag agccugccug ugacuugcag ugccuucaca        60
uagucauccu ugc                                                           73

<210> SEQ ID NO 37
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gggaauccgc aggcuggauu cccgucacag agaacgccug ugacuugcag ugccuucaca        60
uagucauccu ugc                                                           73

<210> SEQ ID NO 38
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gggaauccgc guucuggauu cccgucacag acgucccug ugacuugcag ugccuucaca         60
uagucauccu ugc                                                           73

<210> SEQ ID NO 39
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 39
gggaauccga gacguggauu cccgucacag ucguggucug ugacuugcag ugccuucaca    60
uagucauccu ugc                                                      73

<210> SEQ ID NO 40
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggaauccac cacgaggauu cccgucacag aaccauccug ugacuugcag ugccuucaca    60
uagucauccu ugc                                                      73

<210> SEQ ID NO 41
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggaauccga ugguuggauu cccgucacag aguggaccug ugacuugcag ugccuucaca    60
uagucauccu ugc                                                      73

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aaggaugacu augugaaggc acugc                                         25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggagagagau gggugcgagu ucguc                                         25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggacuggaa gggcuaauuu ucucc                                         25
```

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 45
acaggagcag augauacagu uuuag                          25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 46
auggcaggaa gaagcggagu uagug                          25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
gaagaaauga ugacagcauu ucagg                          25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 48
gugaaggggc aguaguaauu uaaga                          25

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
ggagaccgtg accggtggtg cagatgaact tcagggtca            39

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
tgaccctgaa gttcatctgc accaccggtc acggtctcc            39

```
<210> SEQ ID NO 51
<211> LENGTH: 147
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 51
gggaaaggaa gagcggcgcu ccgaccuuag ucucugcaag auaaaccgug cuauugacca      60
cccucaacac acuuauuuaa uguauugaac ggaccuacga accguguagc acagcagauu     120
ugacccugaa guucaucugc accaccg                                         147

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gctcttcctt tccc                                                        14

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
acccugaagu ucaucugcac caccg                                            25

<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acccugaagu ucaucugcac caccg                                            25

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggagaccgtg accggtggtg cagatgaact tcagggtcat t                          41

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 56
aatgaccctg aagttcatct gcaccaccgg tcacggtctc c                          41

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aatgaccctg aagttcatct gcaccaccg                                        29

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
accctgaagt tcatctgcac caccg                                            25

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aatgaccctg aagttcatct gcaccaccg                                        29
```